US009890175B2

(12) United States Patent
Zhou et al.

(10) Patent No.: US 9,890,175 B2
(45) Date of Patent: Feb. 13, 2018

(54) TAXANE COMPOUND, AND PREPARATION METHOD AND USE THEREOF

(71) Applicant: JIANGSU TASLY DIYI PHARMACEUTICAL CO., LTD., Huai'an (CN)

(72) Inventors: Wei Zhou, Tianjin (CN); Yunrong Jing, Tianjin (CN); Yongfeng Wang, Tianjin (CN); Guocheng Wang, Tianjin (CN)

(73) Assignee: JIANGSU TASLY DIYI PHARMACEUTICAL CO., LTD., Huai'an (CN)

( * ) Notice: Subject to any disclaimer, the term of this patent is extended or adjusted under 35 U.S.C. 154(b) by 0 days.

(21) Appl. No.: 15/039,271

(22) PCT Filed: Nov. 21, 2014

(86) PCT No.: PCT/CN2014/091911

§ 371 (c)(1), (2) Date: May 25, 2016

(87) PCT Pub. No.: WO2015/074606

PCT Pub. Date: May 28, 2015

(65) Prior Publication Data

US 2016/0340365 A1 Nov. 24, 2016

(30) Foreign Application Priority Data

Nov. 22, 2013 (CN) .......................... 2013 1 0594994

(51) Int. Cl.
*C07D 493/08* (2006.01)

(52) U.S. Cl.
CPC .................................. *C07D 493/08* (2013.01)

(58) Field of Classification Search
CPC .................................................... C07D 493/08
See application file for complete search history.

(56) References Cited

U.S. PATENT DOCUMENTS 5,475,011 A * 12/1995 Ojima .................. C07D 205/08 514/320
5,705,508 A 1/1998 Ojima et al.

FOREIGN PATENT DOCUMENTS

| | | |
|---|---|---|
| CN | 1123547 A | 5/1996 |
| CN | 1359384 | 7/2002 |
| CN | 1478091 A | 2/2004 |
| CN | 1923189 A | 3/2007 |
| EP | 0747372 A1 | 12/1996 |

OTHER PUBLICATIONS

Verma & Hansch, 3(4) CHEMMEDCHEM 642-652 (2008) (CAS Abstract).*

Distefano et al., "Anti-Proliferative Activity of a New Class of Taxanes (14β-Hydroxy-10-DEACETYLBACCATIN III Derivatives) on Multidrug-Resistance-Positive Human Cancer Cells", International Journal of Cancer 72:844-850 (1997).

Ferlini et al., "Cytotoxic Effects Toward Human Hematopoietic Progenitor Cells and Tumor Cell Lines of Paclitaxel, Docetaxel, and Newly Developed Analogues IDN5109, IDN5111, and IDN5127", Oncology Research, 11(10):471-478 (1999). (Abstract).

Islam et al., "Investigation of structural requirements of anticancer activity at the paclitaxel/tubulin binding site using CoMFA and CoMSIA", Journal of Molecular Graphics and Modelling 21:263-272 (2003).

Ojima et al., "Syntheses and Structure—Activity Relationships of Taxoids Derived from 14β-Hydroxy-10-deacetylbaccatin III", Journal of Medicinal Chemistry 40(3):267-278 (1997).

Ojima et al., Syntheses and Biological Activity of C-3'-Difluoromethyl-Taxoids, Bioorganic & Medicinal Chemistry 3:1619-1628 (2000).

Polizzi et al., "A Novel Taxane with Improved Tolerability and Therapeutic Activity in a Panel of Human Tumor Xenografts", Cancer Research 59:1036-1040 (1999).

PUBCHEM, "CHEMBL1096578- Compound Summary for CID 46886800 (C46H60N2016)", (2010). (9 pages).

Taraboletti et al., "Antiangiogenic and Antitumor Activity of IDN 5390, a New Taxane Derivative", Clinical Cancer Research 8:1182-1188 (2002).

Verma et al., "Taxane Analogues against Breast Cancer: A Quantitative Structure-Activity Relationship Study", ChemMedChem 3:642-652 (2008).

Verma et al., "Taxane Analogues against Lung Cancer: A Quantitative Structure-Activity Relationship Study", Chemical Biology & Drug Design 73:627-636 (2009).

Vredenburg et al., "Effects of Orally Active Taxanes on P-Glycoprotein Modulation and Colon and Breast Carcinoma Drug Resistance", Journal of the National Cancer Institute 93(16):1234-1245 (2001).

* cited by examiner

*Primary Examiner* — Timothy R Rozof
(74) *Attorney, Agent, or Firm* — Nixon Peabody LLP

(57) ABSTRACT

Provided are taxanes compounds having the structure of formula I, preparation method thereof, and uses of compositions having the compound, pharmaceutical salts and solvates thereof as active ingredients in the preparation of oral antitumor drugs. In the formula, $R_1$ is —$COR_6$, —$COOR_6$, and —$CONR_{7a}R_{7b}$; $R_2$ is C1-C6 alkyl, C1-C6 alkenyl group, a substituted hydrocarbon group, a heterocyclic group, an aromatic group or a substituted aromatic group; $R_3$ is —$OR_6$, —$OCOOR_6$, —$OCOSR_6$, and —$OCONR_{7a}R_{7b}$; $R_4$ is —$OR_6$, —$OCOOR_6$, —$OCOSR_6$, —$OCONR_{7a}R_{7b}$, H, and OH; $R_6$ is C1-C6 alkyl, C1-C6 alkenyl, C1-C6 alkynyl group, a substituted hydrocarbon group, an aromatic group or a heterocyclic group; and $R_{7a}$ and $R_{7b}$ are respectively hydrogen, a hydrocarbon group, a substituted hydrocarbon group or a heterocyclic group.

I

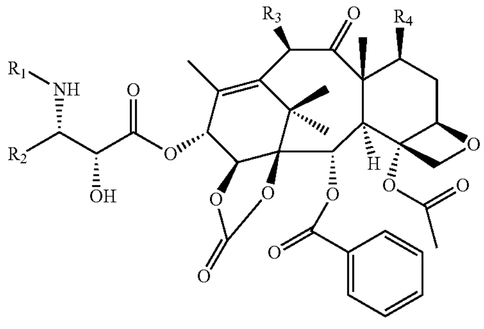

11 Claims, 31 Drawing Sheets

TAXANE COMPOUND, AND PREPARATION METHOD AND USE THEREOF

CROSS-REFERENCE TO RELATED APPLICATIONS

This application is a U.S. national stage of PCT/CN2014/091911, filed on Nov. 21, 2014, which claims priority to Chinese Patent Application No. 201310594994.X, filed on Nov. 22, 2013, the contents of which are each incorporated herein by reference in its entirety.

FIELD OF THE INVENTION

The present invention belongs to the field of pharmaceutical chemistry, and specifically relates to a novel compound, in particular to taxanes compounds. The present invention also relates to the preparation method of the taxanes compounds and use thereof as active ingredients in manufacturing oral antitumor medicaments.

BACKGROUND OF THE INVENTION

Paclitaxel (PTX) has a structure represented by the following formula:

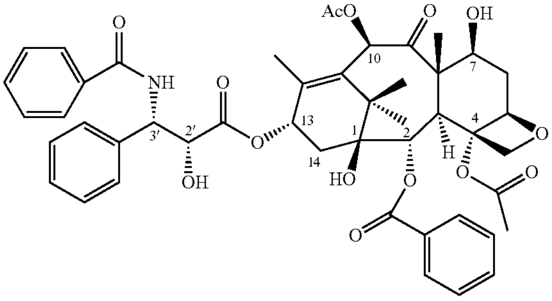

Paclitaxel was extracted from the bark of *Taxus* genus *Taxus brevifolia* in 1971, which is an active antitumor compound with a unique anticancer mechanism and has definite therapeutic effect on a variety of cancers. Currently in clinical practice, paclitaxel is usually administered by intravenous injection. However, due to its poor water solubility, paclitaxel is usually dissolved in a mixed solvent of polyoxyethylated castor oil (Chremophor EL) and ethanol (1:1, v/v), to prepare paclitaxel injections, which is sold under the trade name "Taxol" or "Paxene".

Although a great success has been achieved in clinical application, paclitaxel is also restricted by many factors in the meantime: (1) firstly, paclitaxel itself has toxic and side effects, including dose-limiting toxicity and bone marrow suppression (clinically, it is necessary be used in combination with a growth factor for treatment), on normal tissues and cells, and cannot cross the blood-brain barrier, etc; (2) with the use of Chremophor EL, the ensuing problem is serious allergic reactions, primary hyperlipidemia, central nervous system (CNS) toxicity and pharmacokinetics change of paclitaxel [ten Tije A J, et al, Clin Pharmacokinet 42, 655-685, 2003; H. Gelderblom, et al, Eur. J. Cancer 37 (13), 1590-1598, 2001; van Zuylen L, et al, Invest New Drugs 19, 125-141, 2001; R. B. Weiss, et al, J. Clin. Oncol. 8 (7), 1263-1268, 1990]; (3) multiple drug resistance happens due to long-term medication.

In order to solve the aforesaid problems, many scholars at home and abroad have carried out in-depth studies on the structure-activity relationships of paclitaxel, including changing pharmaceutical dosage form, developing a prodrug of paclitaxel, synthesizing taxane derivatives, medication in combination with P-gp inhibitor, and the like. New ways are continuously explored to improve its water solubility, enhance therapeutic effect as well as reduce toxic and side effects.

It has enormous practical significance to carry out studies on the oral taxanes derivatives, since changing the nature of taxanes compounds themselves can fundamentally solve the problems thereof such as poor water-solubility, high toxicity and the like, so as to improve the oral bioavailability, reduce toxic and side effects and enhance therapeutic effect thereof. Furthermore, it will be able to avoid adverse reactions brought by co-solvents, and help prolong therapeutic effect and enhance tolerance of patients by converting injection administration to oral administration.

The researchers found that in the structural modification of paclitaxel molecule, the variation of substituents at C7, C9 and C10 positions have little effect on activity thereof, but these positions are binding sites with P-gp protein. The affinity of paclitaxel molecule with P-gp protein is affected by the size, electrical, hydrogen bond forming ability of the substituents on the positions. Thus, modification on these groups could overcome the multiple drug resistance caused by P-gp over-expression and solve the problem of low oral bioavailability and the like.

14β-hydroxy baccatin III (14β-OH-DAB) has a structure represented by the following formula:

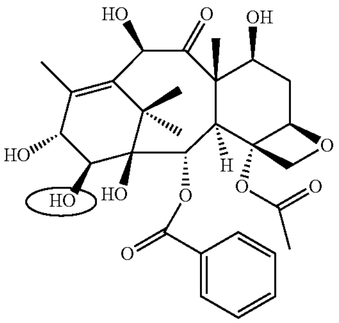

It is a natural taxane derivative extracted from needle leaves of *T. wallichiana* Zucc. It has good water-solubility, mainly because a hydroxy group is introduced at C14 position thereof. For this purpose, such compound derived from 14β-OH-DAB is expected to have improved water-solubility and increased oral bioavailability (Appendino, G. et al, J. Chem. Soc., Perkins Trans, 1, 2925-2929, 1992).

In view of this, the inventors were engaged in research of 14β-OH-DAB derivatives, and eventually found out a series of novel compounds with improved oral bioavailability. As shown in pharmacological experiments, compared with the prior art, these taxanes derivatives containing structure of 1,14-carbonate baccatin III synthesized in the present invention have strong cytotoxicity to a variety of human cancer cell lines and broad-spectrum anti-tumor effects. It can be seen from the in vitro activity data on MCF-7 breast cancer cell line that the cytotoxicity is maintained, while some derivatives even have better cytotoxicity than that of the prior art. The in vivo absorption and transport of taxanes derivatives is predicted by using the human-derived colorectal adenocarcinoma cell line Caco-2 cell monolayer model. It can be seen from the experimental results that, compared with the prior art, most of these derivatives have improved oral bioavailability. Therefore, the cytotoxicity of these taxanes derivatives containing structure of 1,14-carbonate baccatin III are maintained (or even enhanced), furthermore, their oral bioavailability are also enormously improved.

CONTENT OF THE INVENTION

The present invention provides taxanes compounds having the structure represented by the following general formula I:

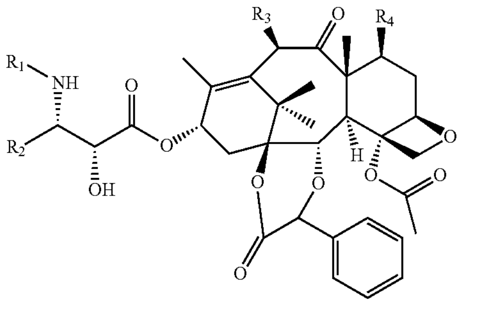

wherein, $R_1$ is —$COR_6$, —$COOR_6$, or —$CONR_{7a}R_{7b}$;

$R_2$ is a C1-C6 alkyl, a C1-C6 alkenyl group, a substituted hydrocarbon group, a heterocyclic group, an aromatic group or a substituted aromatic group;

$R_3$ is —$OR_6$, —$OCOOR_6$, —$OCOSR_6$, or —$OCONR_{7a}R_{7b}$;

$R_4$ is —$OR_6$, —$OCOOR_6$, —$OCOSR_6$, —$OCONR_{7a}R_{7b}$, H or OH;

wherein, $R_6$ is a C1-C6 alkyl, a C1-C6 alkenyl, a C1-C6 alkynyl group, a substituted hydrocarbon group, an aromatic group or a heterocyclic group; $R_{7a}$ and $R_{7b}$ are respectively hydrogen, a hydrocarbon group, a substituted hydrocarbon group or a heterocyclic group.

The present invention further provides a preparation method of taxanes compounds of the present invention.

Said preparation method of taxanes compounds of the present invention comprises the following steps:

Step 1 synthesis of taxanes mother nucleus part: by using 10-deacetyl baccatin III (10-DAB) as raw material, firstly, the hydroxyl groups at C7 and C10 positions of the mother nucleus part are selectively protected with substitutents, then the C13 hydroxy group is oxidized into keto-carbonyl group, followed by highly stereoselectively introducing a hydroxyl group with β configuration at C14 by using N-(sulfonyl) oxaziridine, to form 1,14-carbonate structure under the action of N,N'-carbonyldiimidazole (CDI), and finally the C13 keto-carbonyl group is highly stereoselectively reduced into hydroxyl group with α configuration by CBS reduction method to give the taxanes mother nucleus part;

Step 2 synthesis of a precursor of five-member ring oxazolidine acid side chain: the precursor of five-member ring oxazolidine acid side chain is prepared by a series of reactions including introduction of protective groups, addition condensation, acid hydrolysis, aldol condensation, catalytic hydrogenation and the like;

Step 3 synthesis of taxanes derivatives: the precursor of five-member ring oxazolidine acid side chain is linked with the taxanes mother nucleus part by esterification, and a series of taxanes derivatives are generated after removal of protective group by acid hydrolysis.

More specifically, the preparation method of the taxanes compounds of the present invention comprises the following steps:

Step 1 synthesis of taxanes mother nucleus part: by using 10-deacetyl baccatin III (10-DAB) as raw material, firstly, the hydroxyl groups at C7 and C10 positions of the mother nucleus part are selectively protected with substitutents, then the C13 hydroxy group is oxidized into keto-carbonyl group, followed by highly stereoselectively introducing a hydroxyl group with β configuration at C14 by using N-(sulfonyl) oxaziridine, to form 1,14-carbonate structure under the action of CDI, and finally C13 keto-carbonyl group is highly stereoselectively reduced into hydroxyl group with α configuration by CBS reduction method to give the taxanes mother nucleus part;

Step 2 synthesis of a precursor of five-member ring oxazolidine acid side chain: glycolic acid, used as raw material, is protected successively by benzyl group and butyloxycarbonyl group (Boc group) to generate the Boc-protected benzyl glycolate; different substituted aldehydes are condensed with ($S_R$)-t-butyl sulfinamide to form the corresponding enamine compounds; the Boc-protected benzyl glycolate and the enamine compound are reacted via an addition reaction in the presence of lithium salt, and then a chiral intermediate is given after acid hydrolysis, and the obtained intermediate is reacted with 1,1'-(dimethoxymethyl) p-methoxybenzene via an aldol condensation reaction, catalyzed by pyridinium p-toluenesulfonate (PPTS) to obtain a condensation compound. The amino group of the condensation compound is substituted with different substituents, and the precursor of five-member ring oxazolidine acid side chain is finally given after catalytic hydrogenation;

Step 3 synthesis of taxanes derivatives: the precursor of five-member ring oxazolidine acid side chain is linked with the taxanes mother nucleus part by esterification, and a series of taxanes derivatives are generated after removal of the protective group by acid hydrolysis.

Furthermore, the present invention provides a pharmaceutical composition comprising the compounds of the above defined general formula (I), pharmaceutically acceptable salts or solvates thereof as active ingredients, as well as the use of the same in manufacturing oral antitumor medicaments.

The present invention has the following advantages:

1. In the present invention, the CBS reduction method is selected in stereoselective reduction of C13 keto-carbonyl group. Compared with the traditional reduction method by using metal borohydride, the CBS reduction method is able to highly stereoselectively reduce to obtain hydroxyl group with α configuration on C13 with an ee value>99.9% and a yield of 90% or higher.

2. A series of taxanes derivatives containing 1,14-carbonate baccatin III were synthesized by simultaneously changing substituents at multiple positions of C7, C10, C14, C3'N and C3' of paclitaxel. In the in vitro cytotoxicity assay on a variety of cancer cell lines, they showed good antitumor activities. The in vitro oral bioavailability of such taxanes derivatives was predicted by using Caco-2 cell monolayer trans-membrane transport assay, showing from the experimental results that the membrane permeability of most of such derivatives were higher than that of paclitaxel and the oral bioavailability thereof were expected to be improved at different levels. By analyzing the result of efflux ratio in the bidirectional transport assay, it was shown that such derivatives could inhibit the efflux effect of P-gp in different degrees, and further verified that the oral absorption capacity of these compounds was improved. In addition, the compound PCMI-08, which showed the highest membrane permeability in the in vitro assay, was selected to carry out in vivo oral bioavailability with rats. It was shown from the experimental results that its absolute oral bioavailability was increased to 65.8%, indicating that the in vivo oral absorption capability thereof was improved in a significant degree by compared with that of paclitaxel. Accordingly, the taxanes derivatives containing 1,14-carbonate baccatin III of the present invention were potential oral antitumor medicaments.

DETAILED DESCRIPTION OF THE INVENTION

Figure 1:
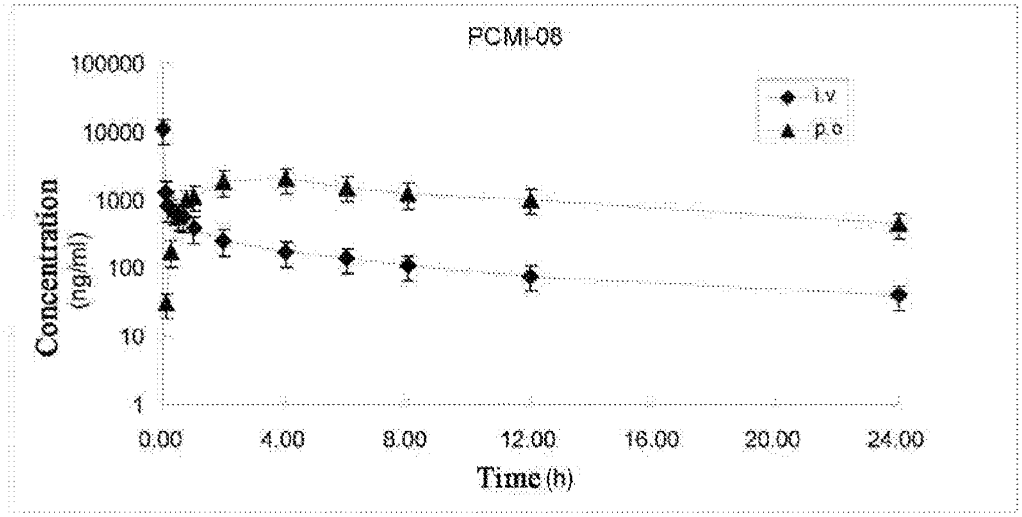
FIG. 1 is the plasma concentration-time curve of PCMI-08.
Figure 2:
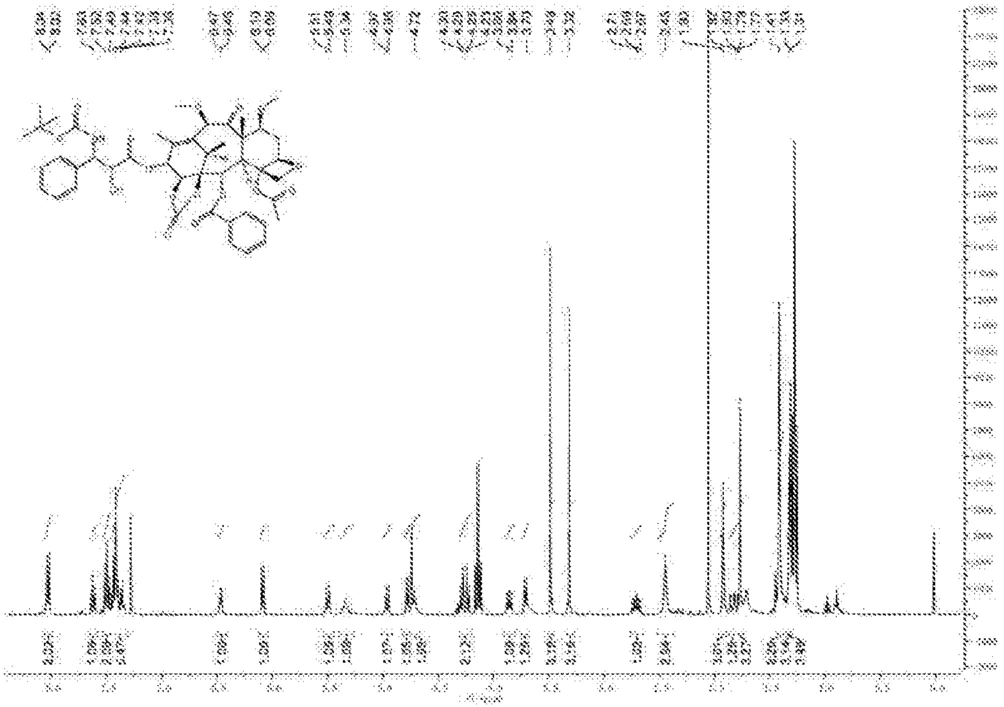
FIG. 2 is the $^1H$ NMR spectrum of PCMI-01.
Figure 3:
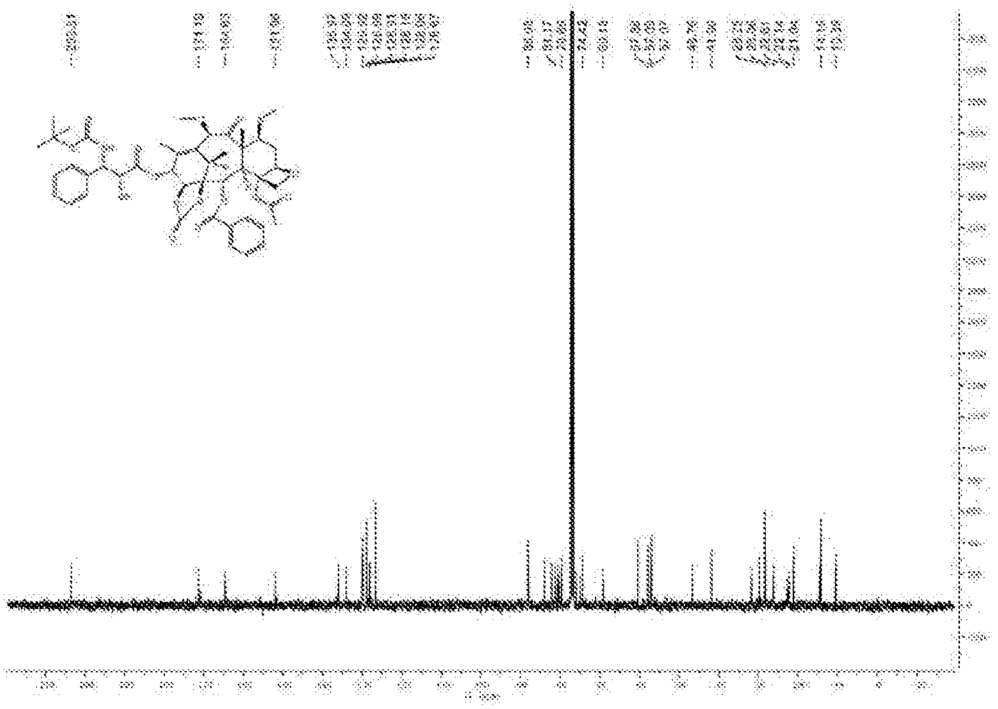
FIG. 3 is the $^{13}C$ NMR spectrum of PCMI-01.
Figure 4:
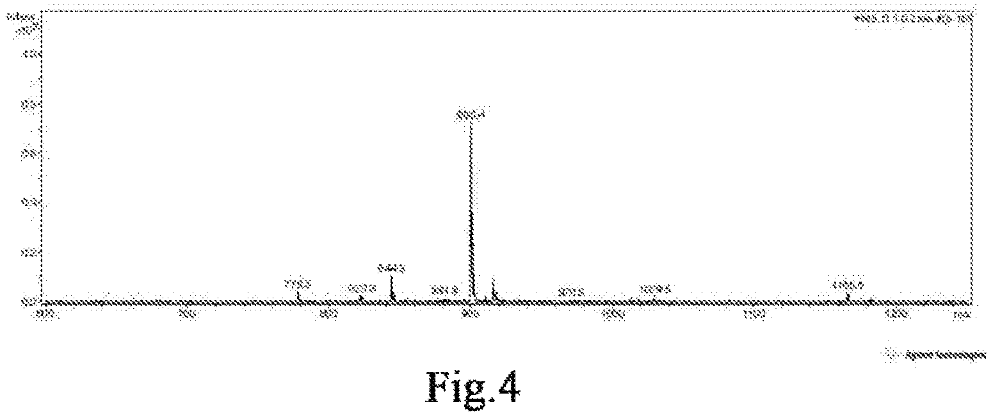
FIG. 4 is the MS spectrum of PCMI-01.
Figure 5:
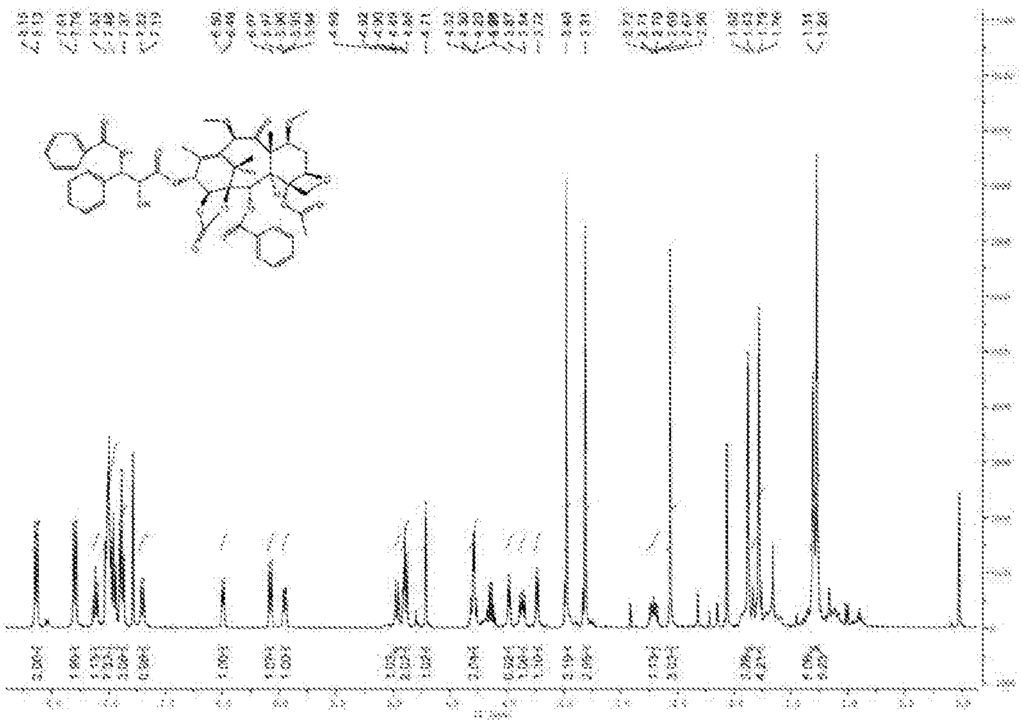
FIG. 5 is the $^1H$ NMR spectrum of PCMI-02.
Figure 6:
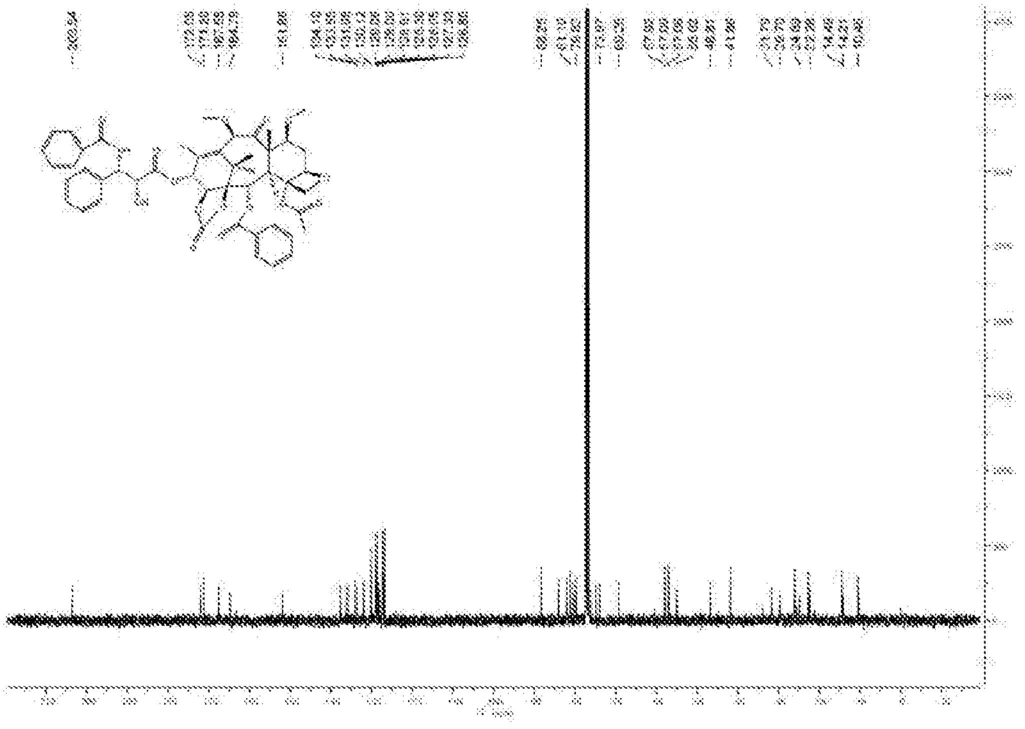
FIG. 6 is the $^{13}C$ NMR spectrum of PCMI-02.
Figure 7:
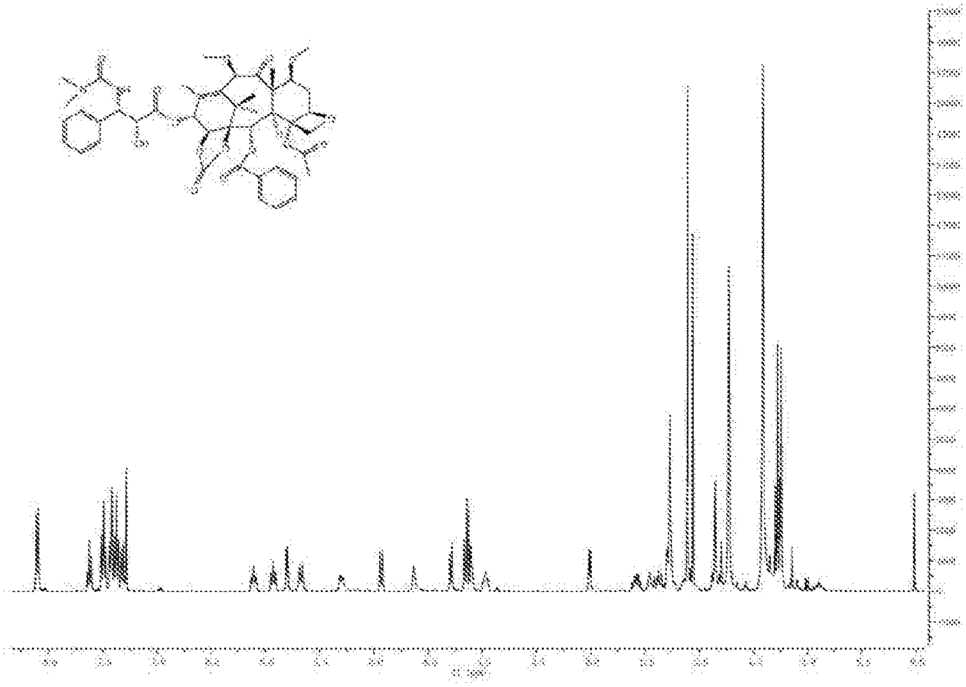
FIG. 7 is the $^1H$ NMR spectrum of PCMI-03.
Figure 8:
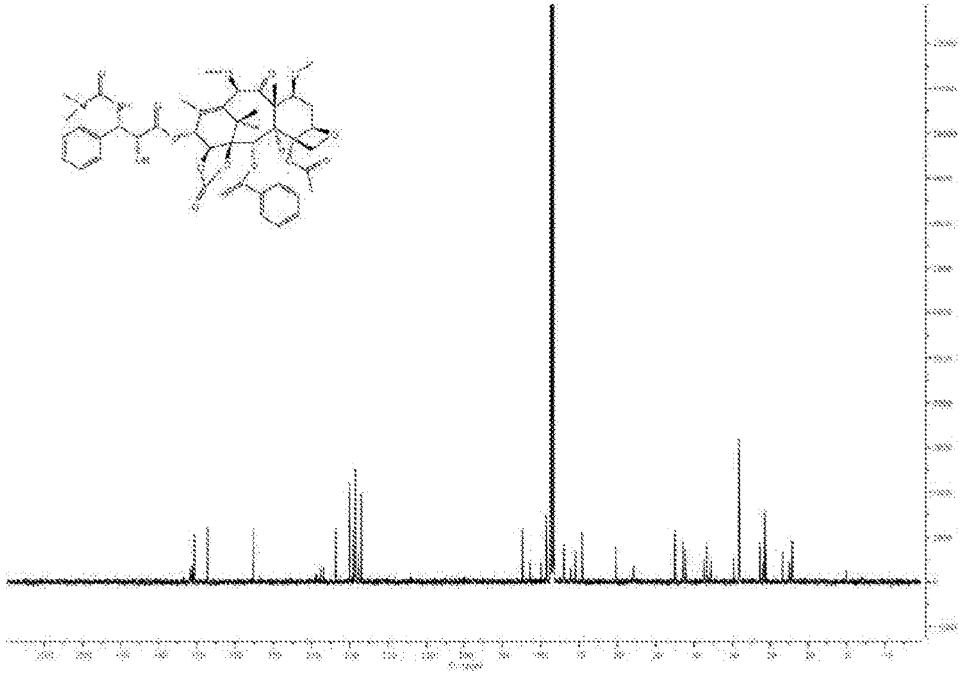
FIG. 8 is the $^{13}C$ NMR spectrum of PCMI-03.
Figure 9:
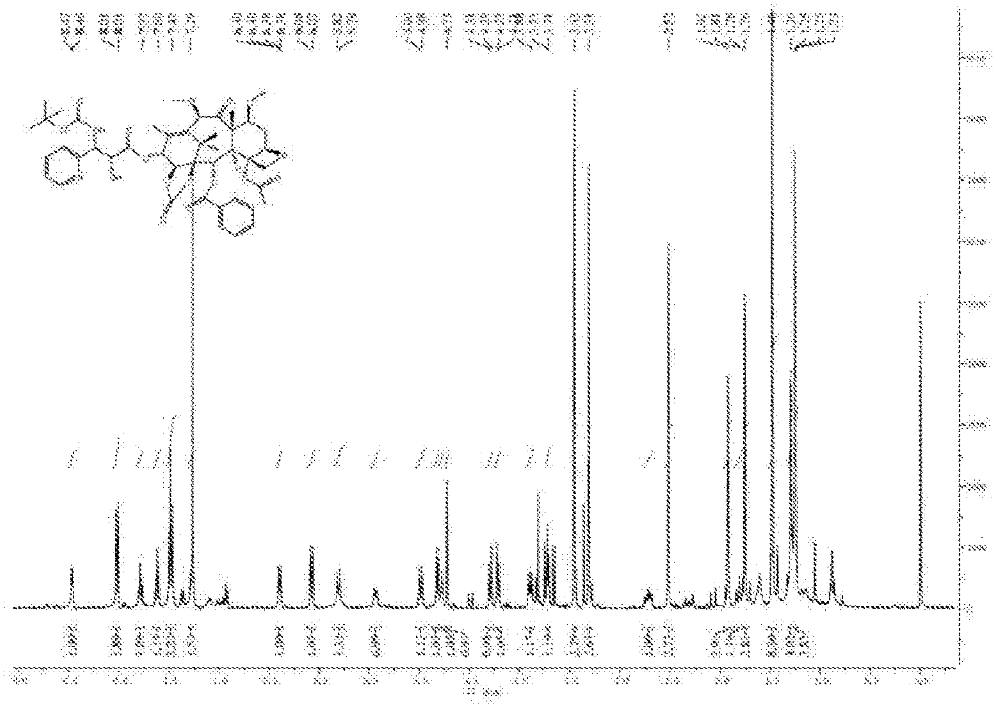
FIG. 9 is the $^1H$ NMR spectrum of PCMI-04.
Figure 10:
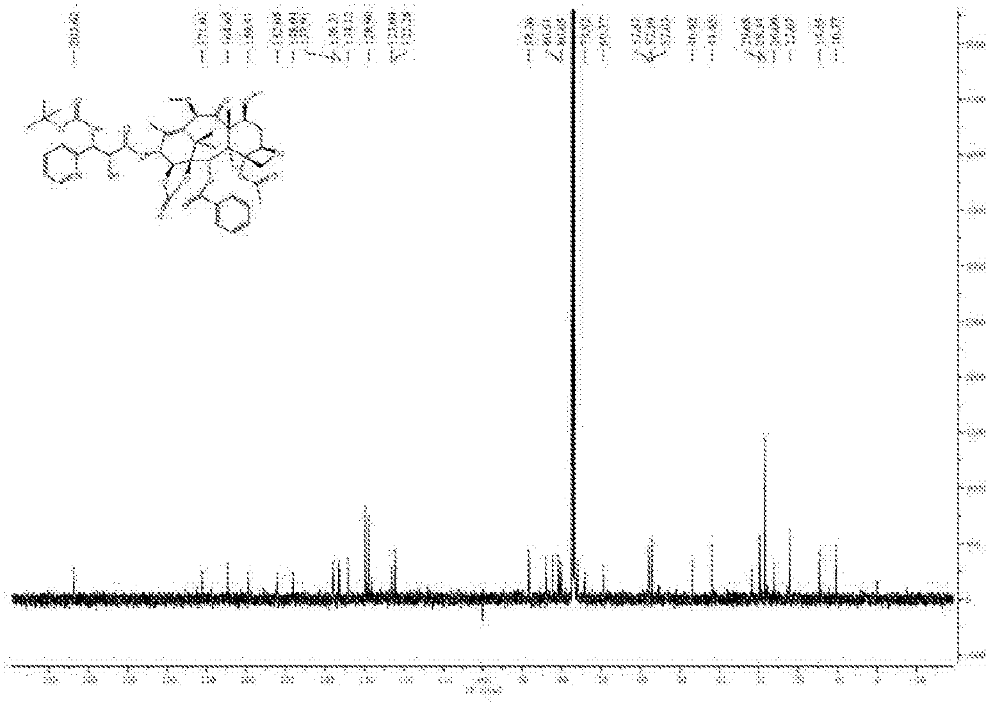
FIG. 10 is the $^{13}C$ NMR spectrum of PCMI-04.
Figure 11:
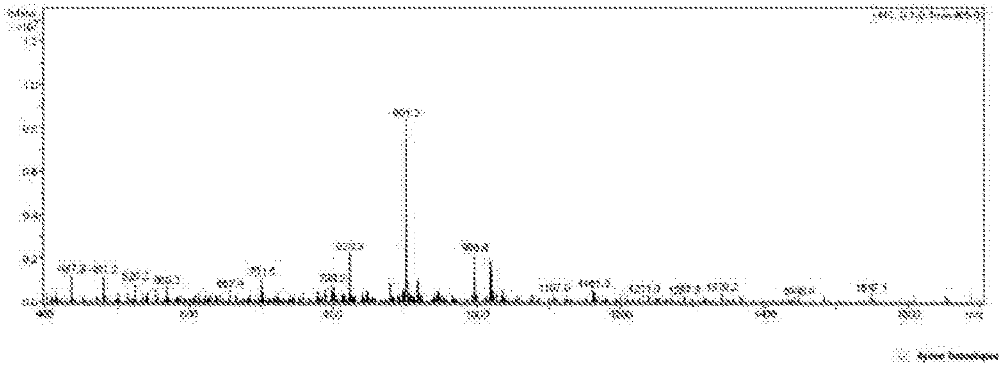
FIG. 11 is the MS spectrum of PCMI-04.
Figure 12:
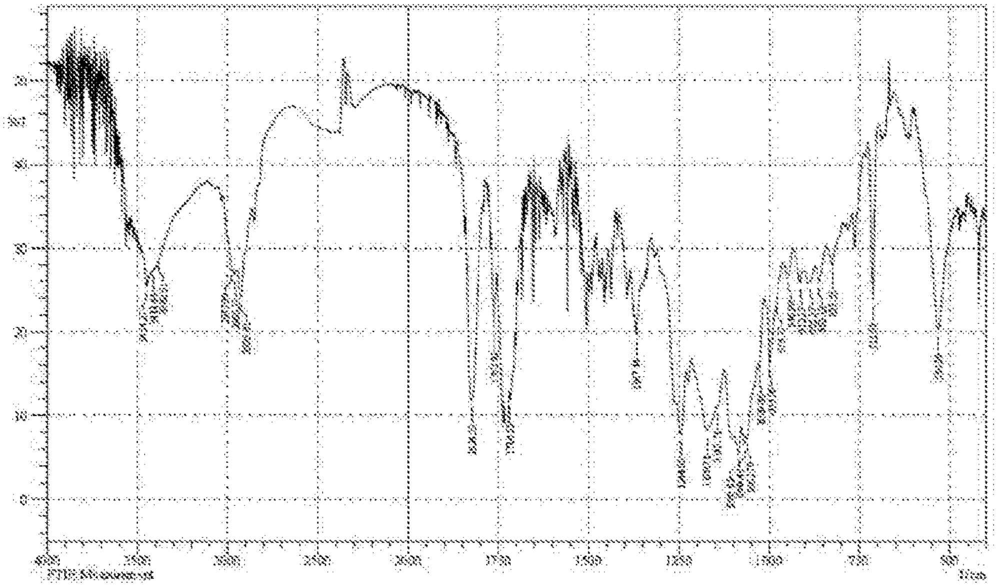
FIG. 12 is the IR spectrum of PCMI-04.
Figure 13:
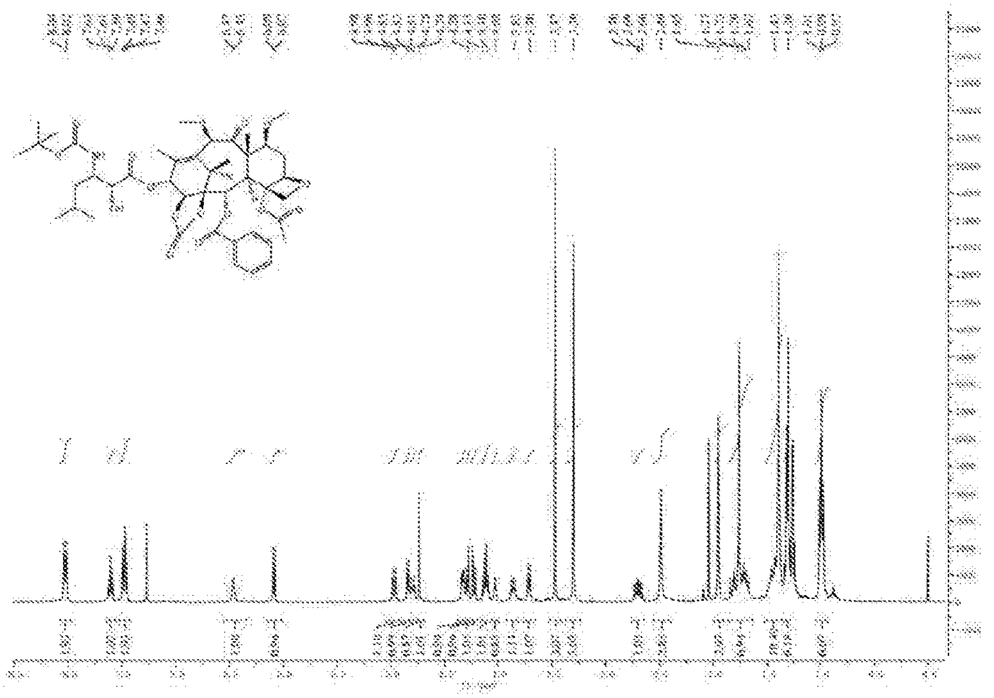
FIG. 13 is the $^1H$ NMR spectrum of PCMI-05.
Figure 14:
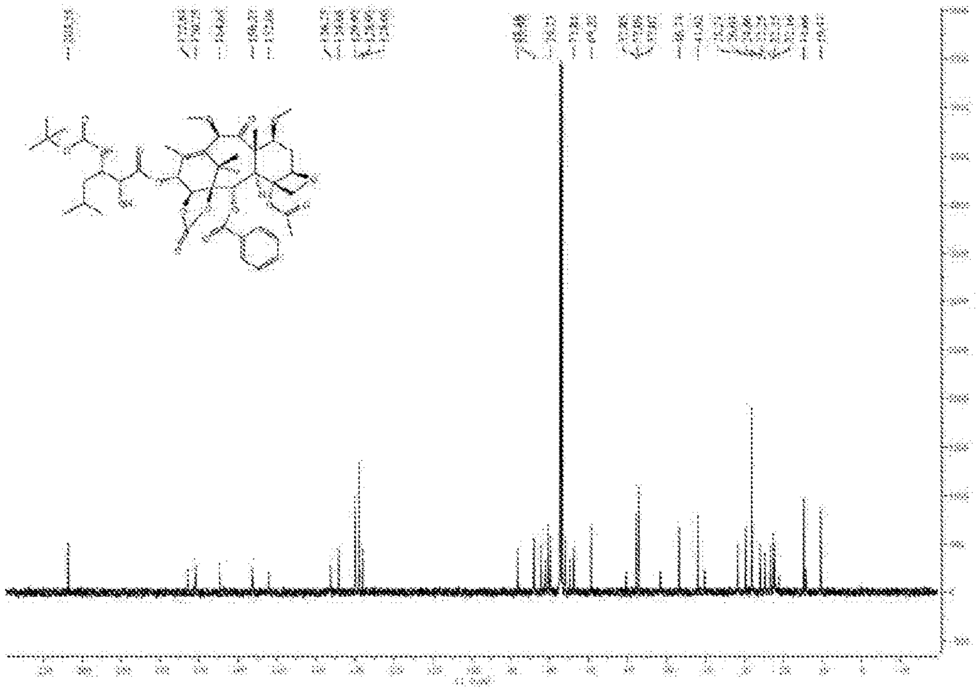
FIG. 14 is the $^{13}C$ NMR spectrum of PCMI-05.
Figure 15:
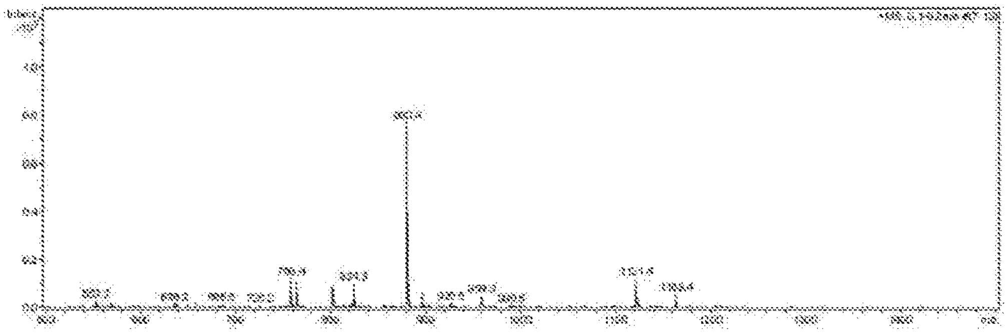
FIG. 15 is the MS spectrum of PCMI-05.
Figure 16:
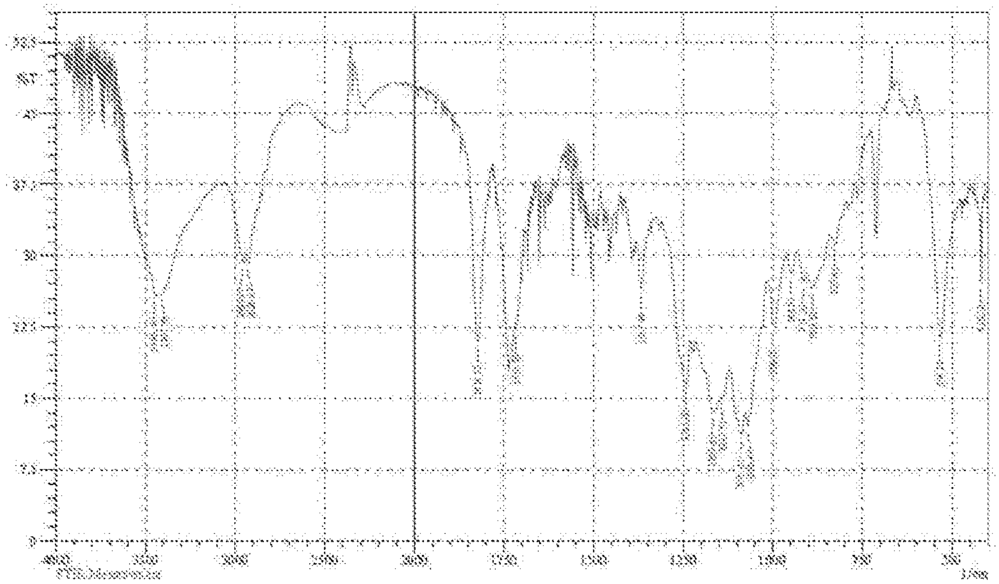
FIG. 16 is the IR spectrum of PCMI-05.
Figure 17:
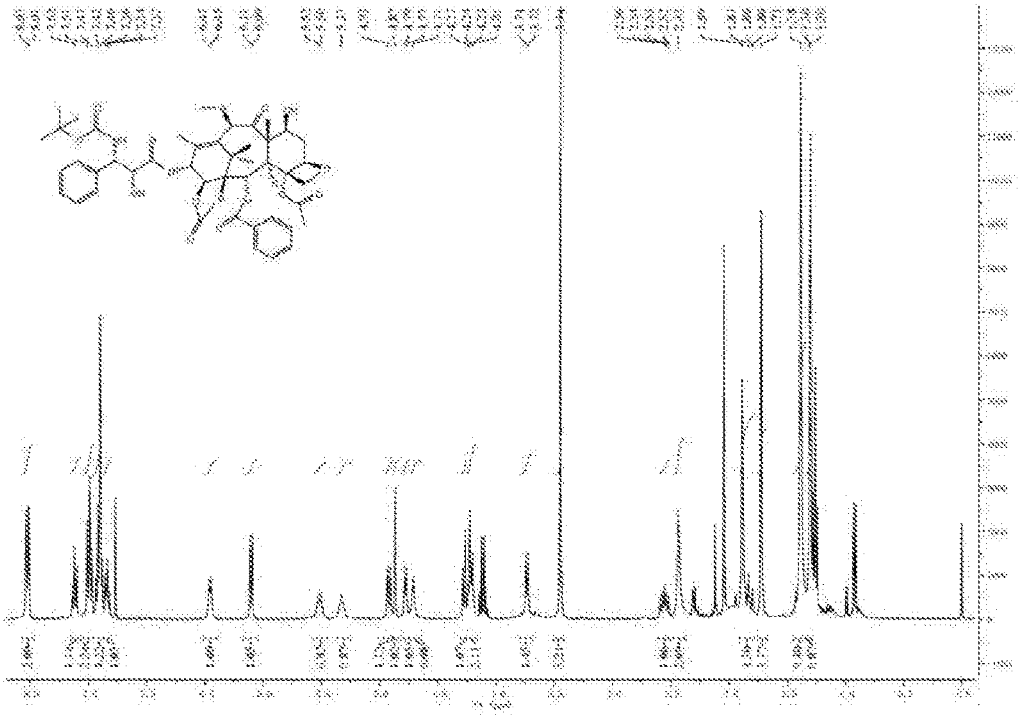
FIG. 17 is the $^1H$ NMR spectrum of PCMI-06.
Figure 18:
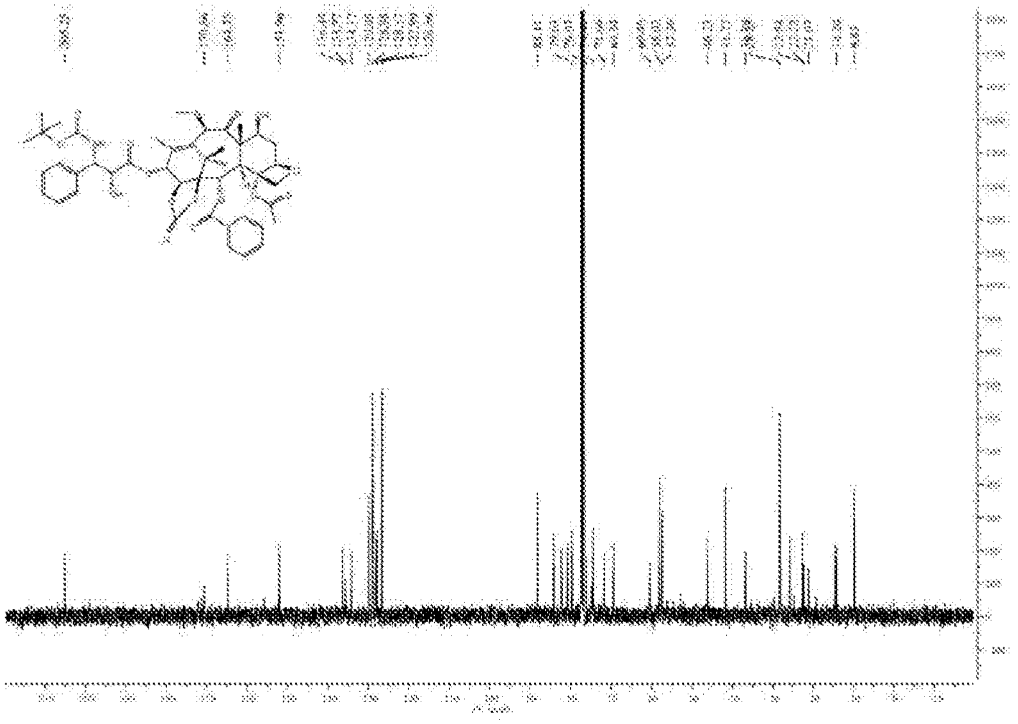
FIG. 18 is the $^{13}C$ NMR spectrum of PCMI-06.
Figure 19:
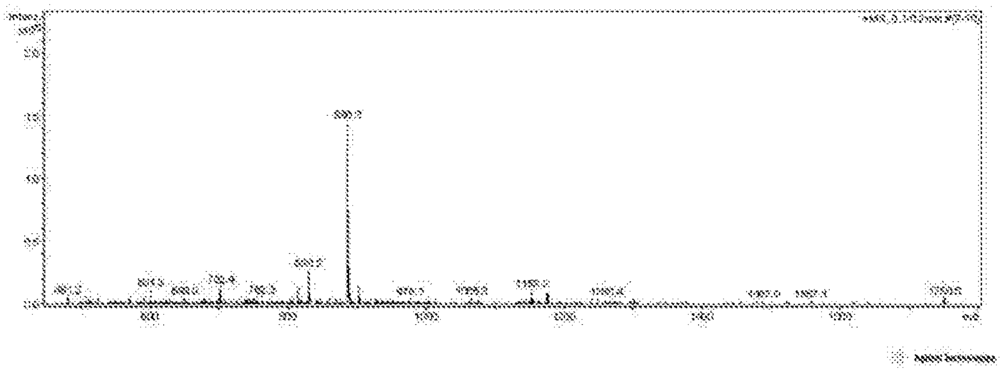
FIG. 19 is the MS spectrum of PCMI-06.
Figure 20:
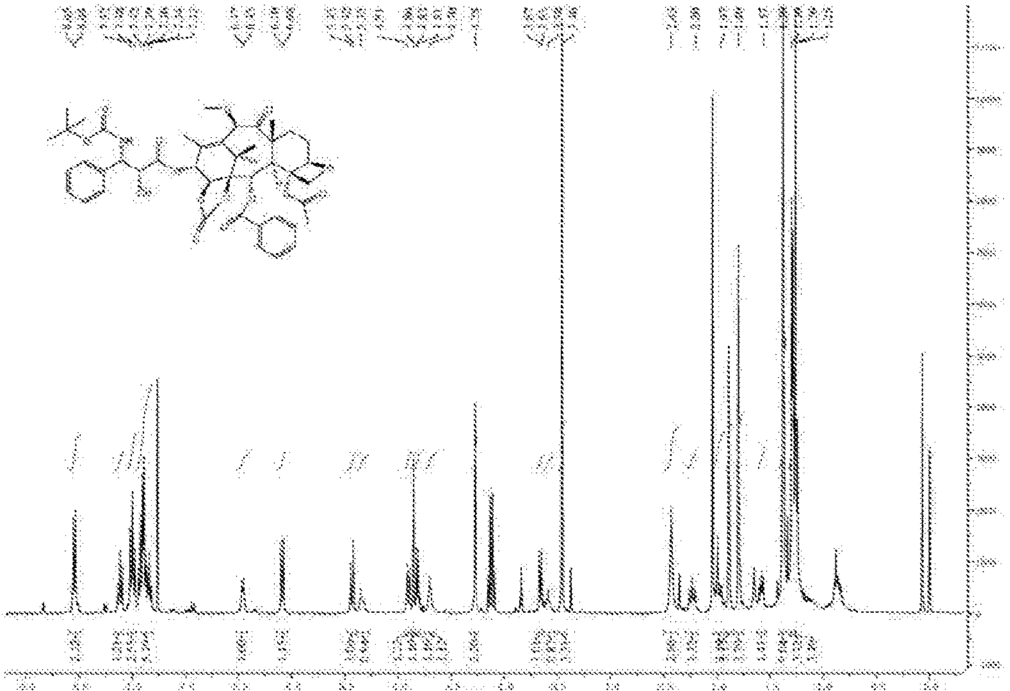
FIG. 20 is the $^1H$ NMR spectrum of PCMI-07.
Figure 21:
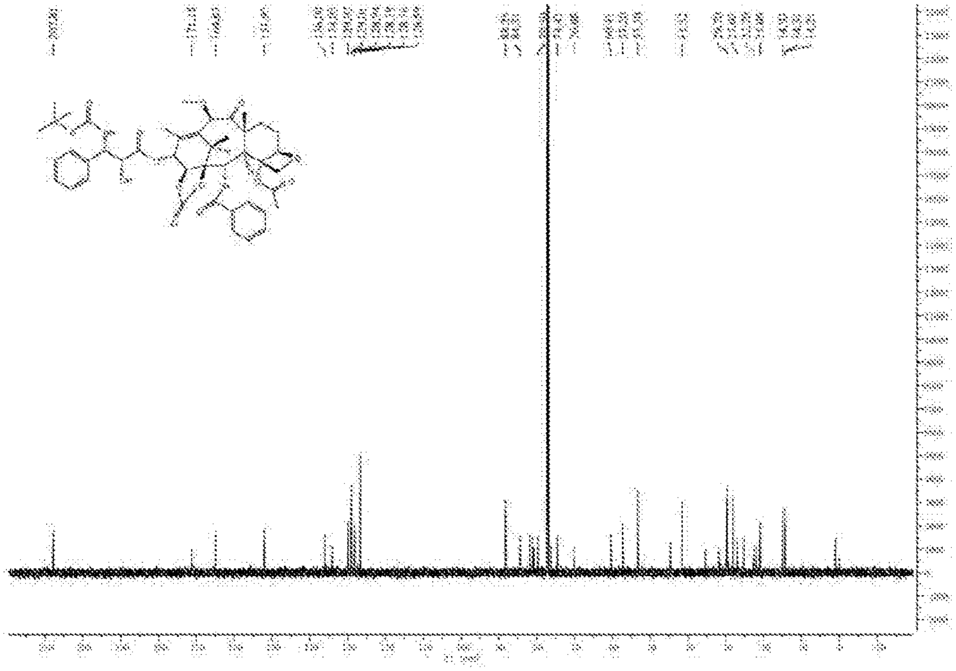
FIG. 21 is the $^{13}C$ NMR spectrum of PCMI-07.
Figure 22:
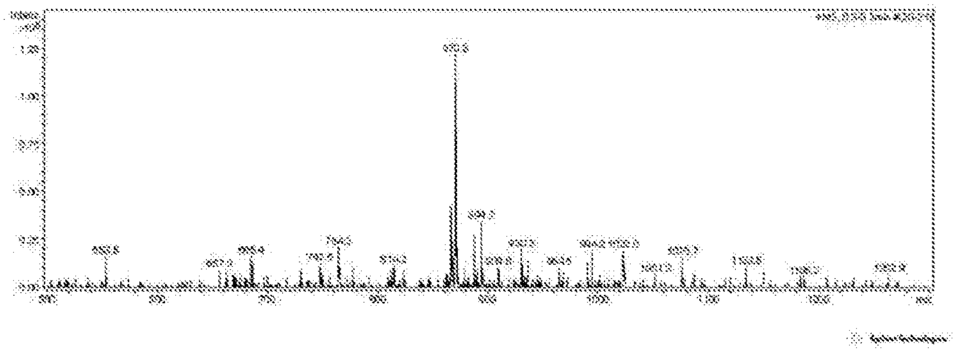
FIG. 22 is the MS spectrum of PCMI-07.
Figure 23:
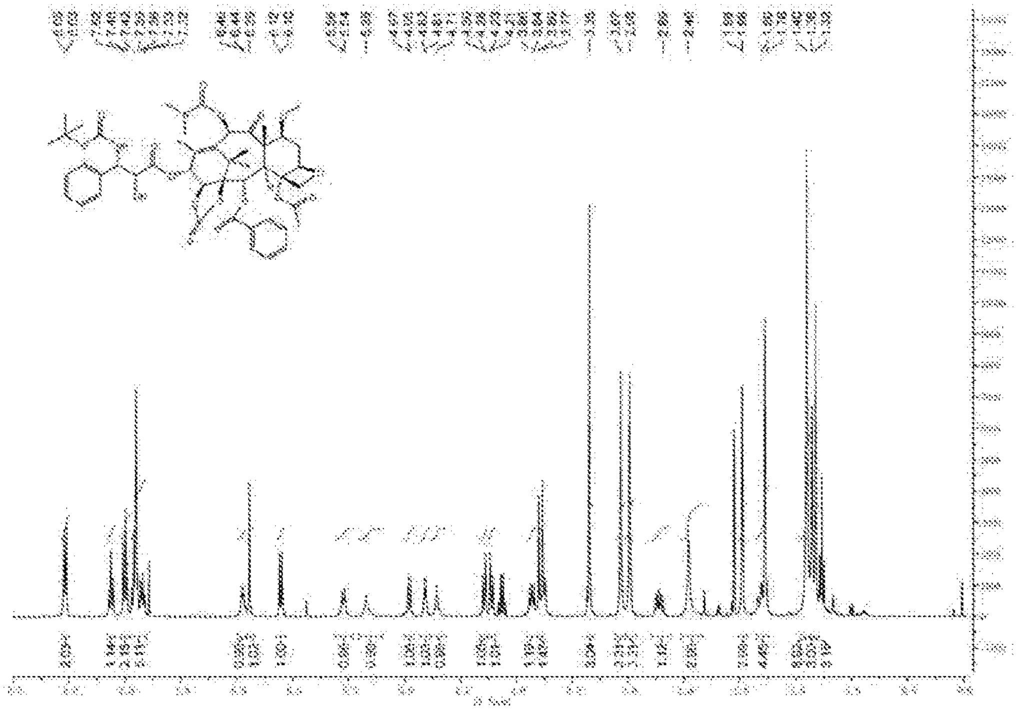
FIG. 23 is the $^1H$ NMR spectrum of PCMI-08.
Figure 24:
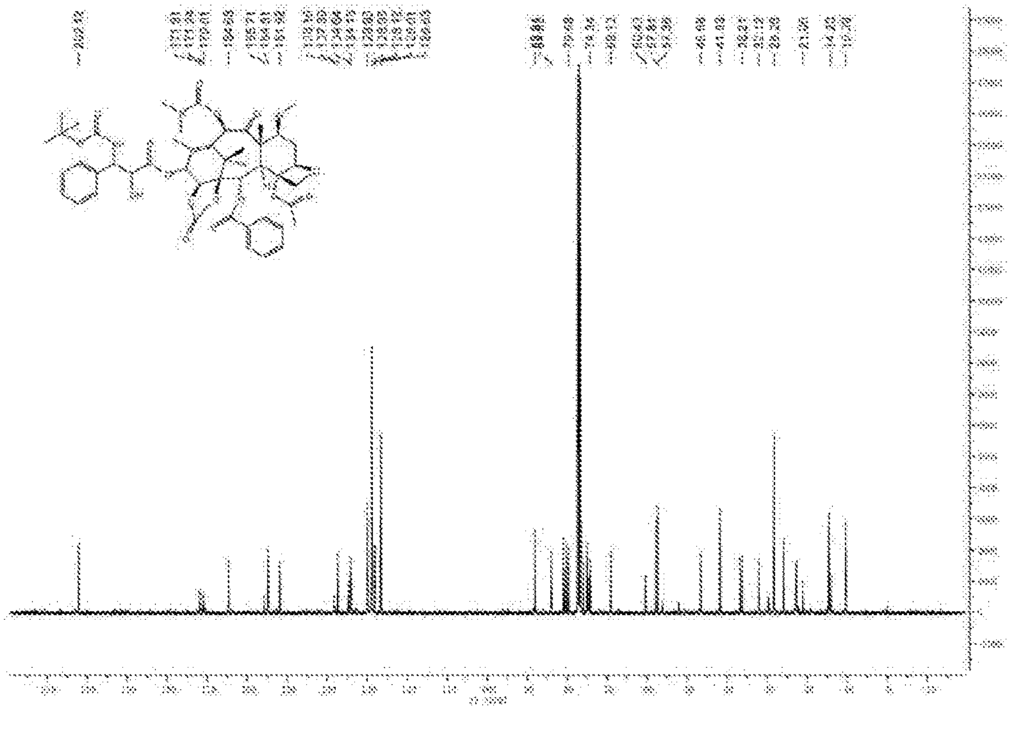
FIG. 24 is the $^{13}C$ NMR spectrum of PCMI-08.
Figure 25:
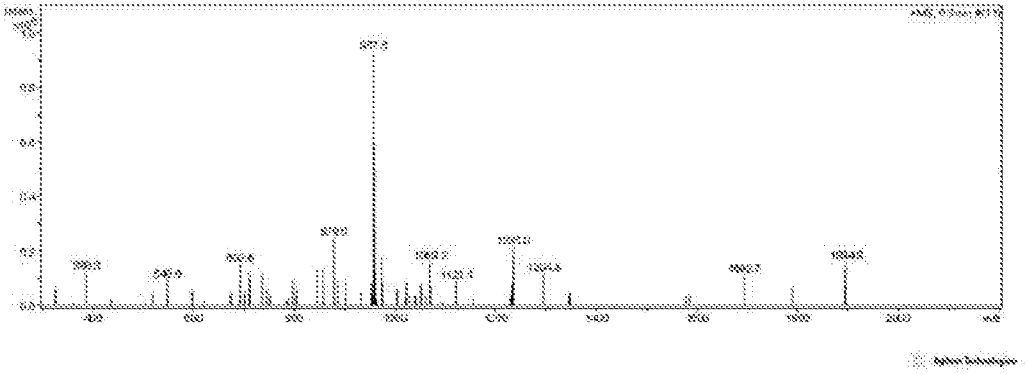
FIG. 25 is the MS spectrum of PCMI-08.
Figure 26:
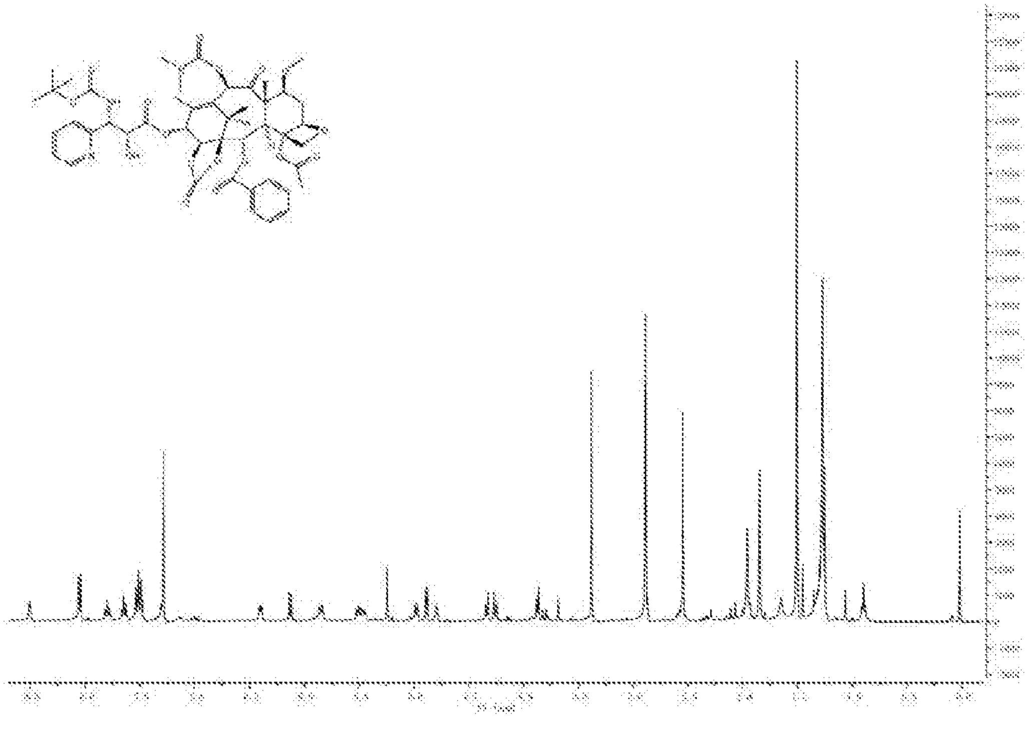
FIG. 26 is the $^1H$ NMR spectrum of PCMI-09.
Figure 27:
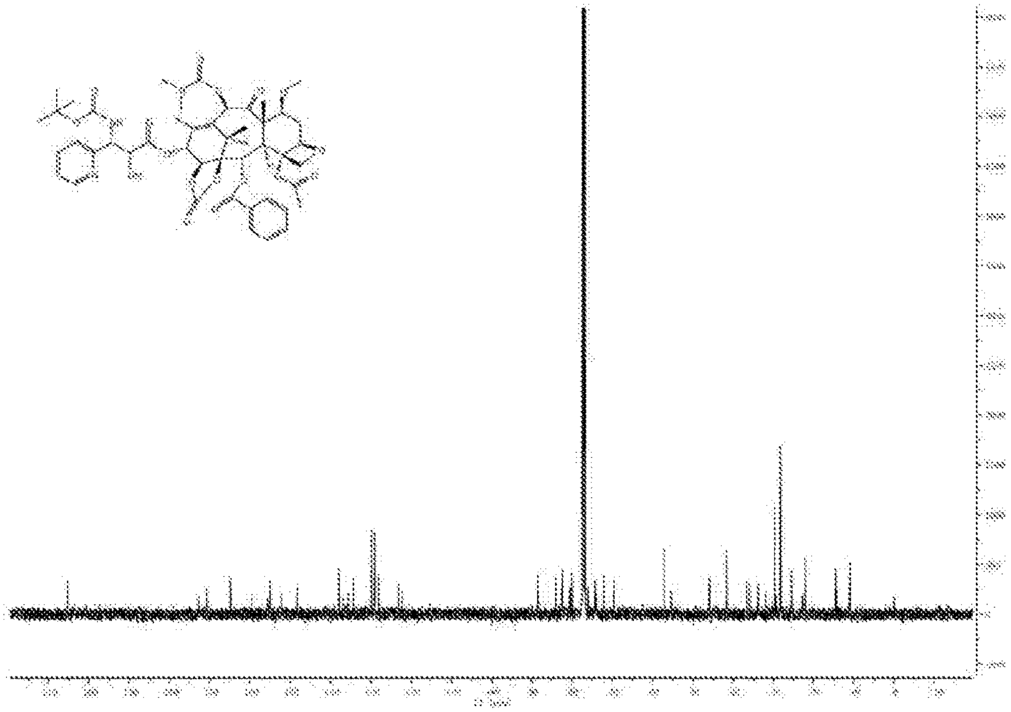
FIG. 27 is the $^{13}C$ NMR spectrum of PCMI-09.
Figure 28:
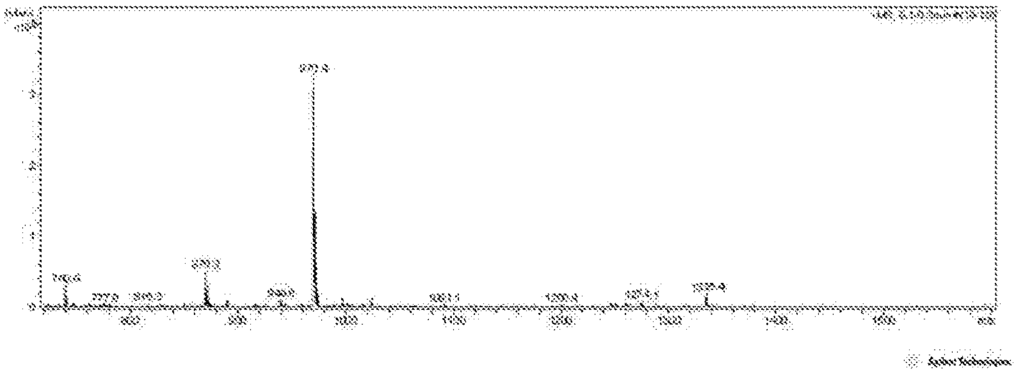
FIG. 28 is the MS spectrum of PCMI-09.
Figure 29:
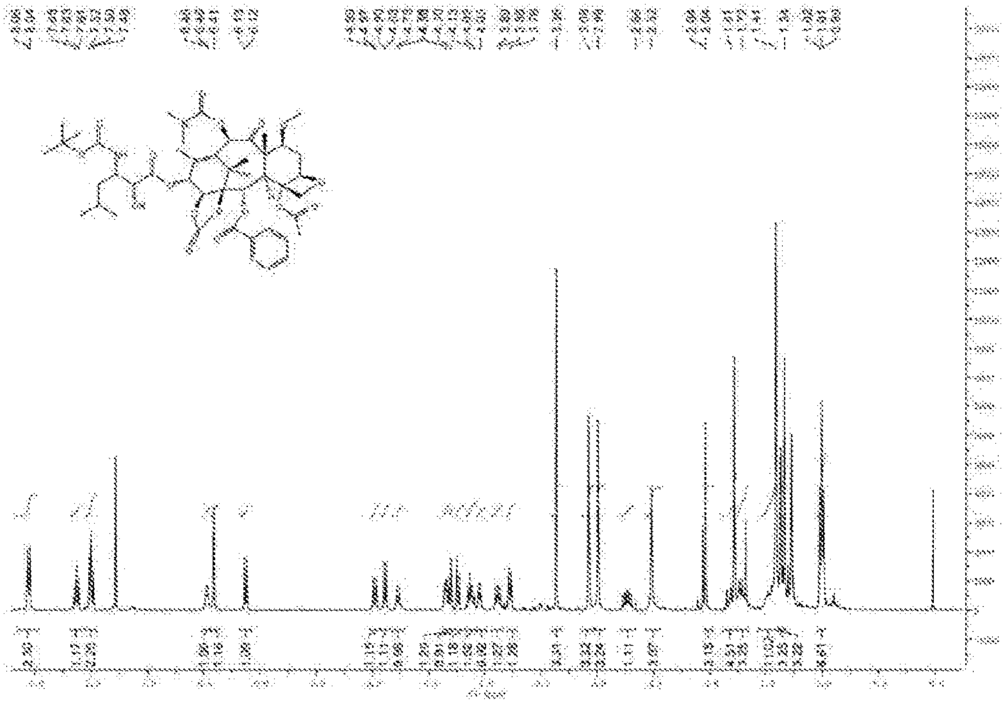
FIG. 29 is the $^1H$ NMR spectrum of PCMI-10.
Figure 30:
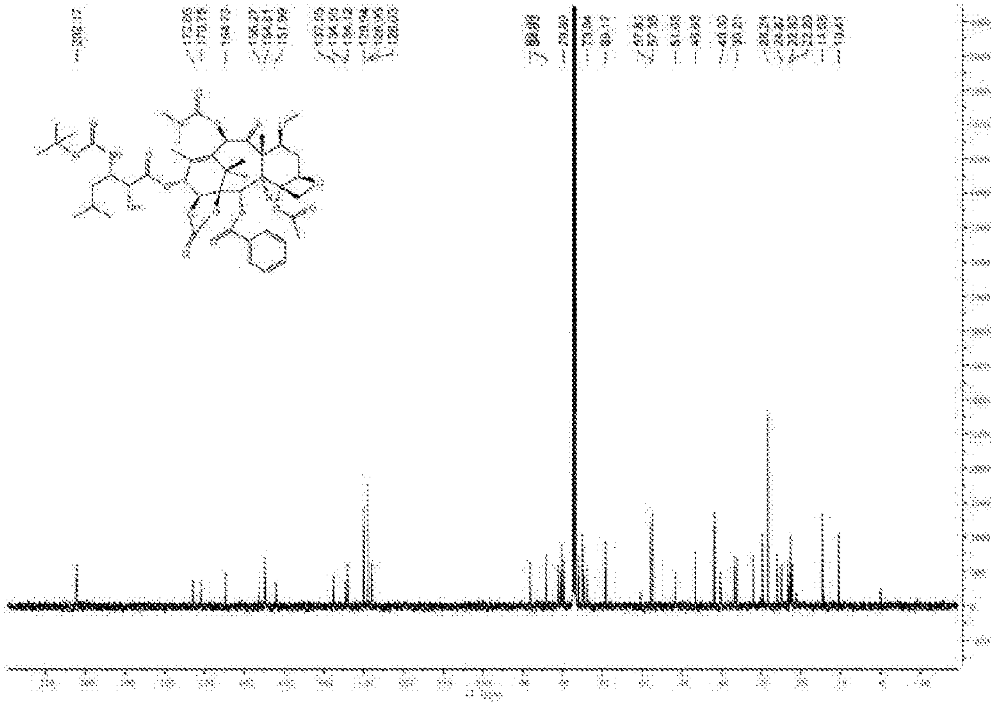
FIG. 30 is the $^{13}C$ NMR spectrum of PCMI-10.
Figure 31:
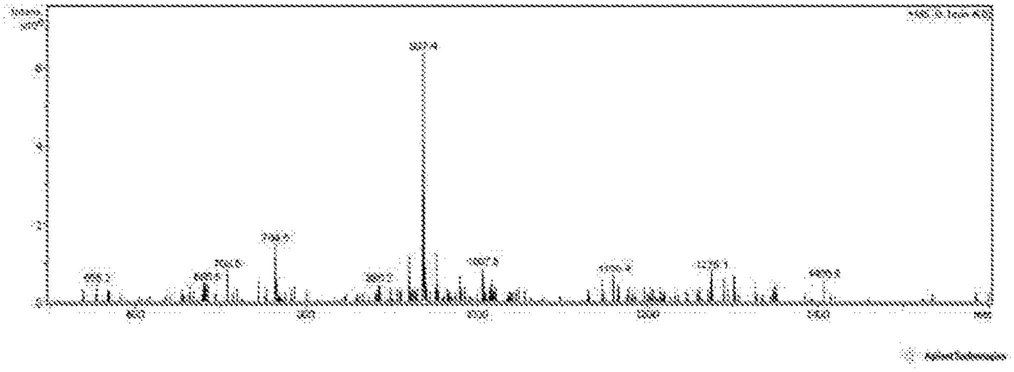
FIG. 31 is the MS spectrum of PCMI-10.
Figure 32:
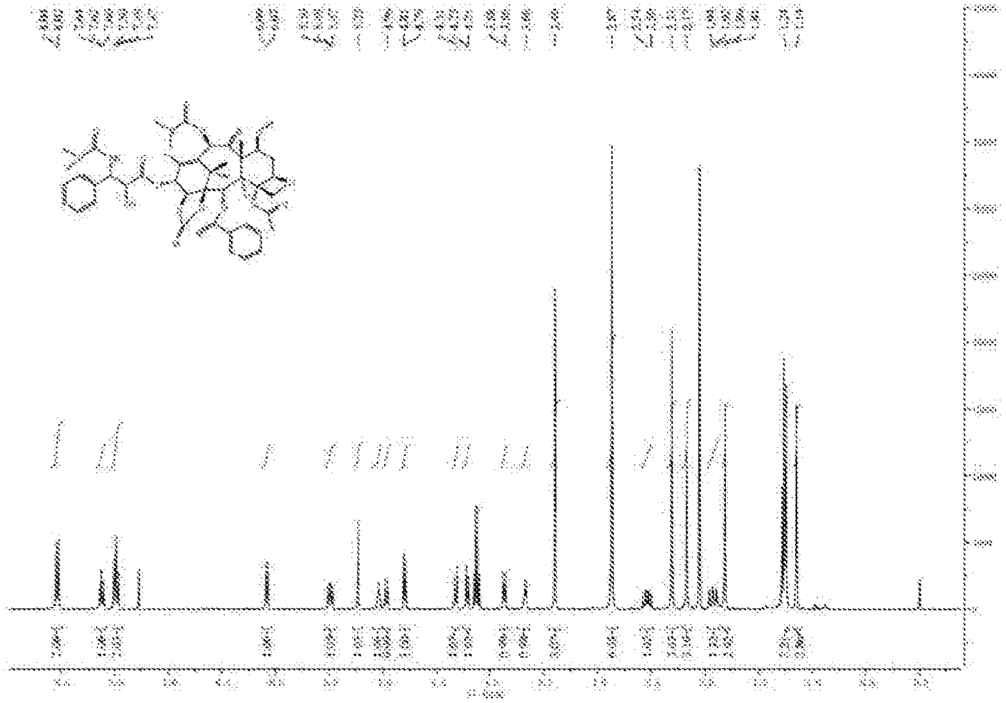
FIG. 32 is the $^1H$ NMR spectrum of PCMI-11.
Figure 33:
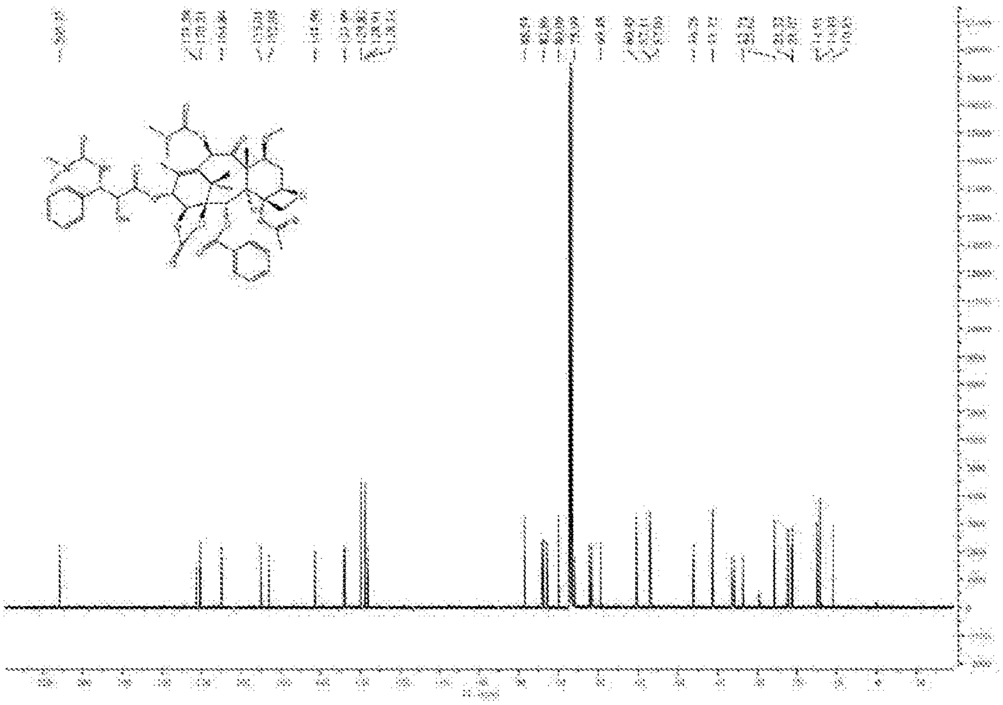
FIG. 33 is the $^{13}C$ NMR spectrum of PCMI-11.
Figure 34:
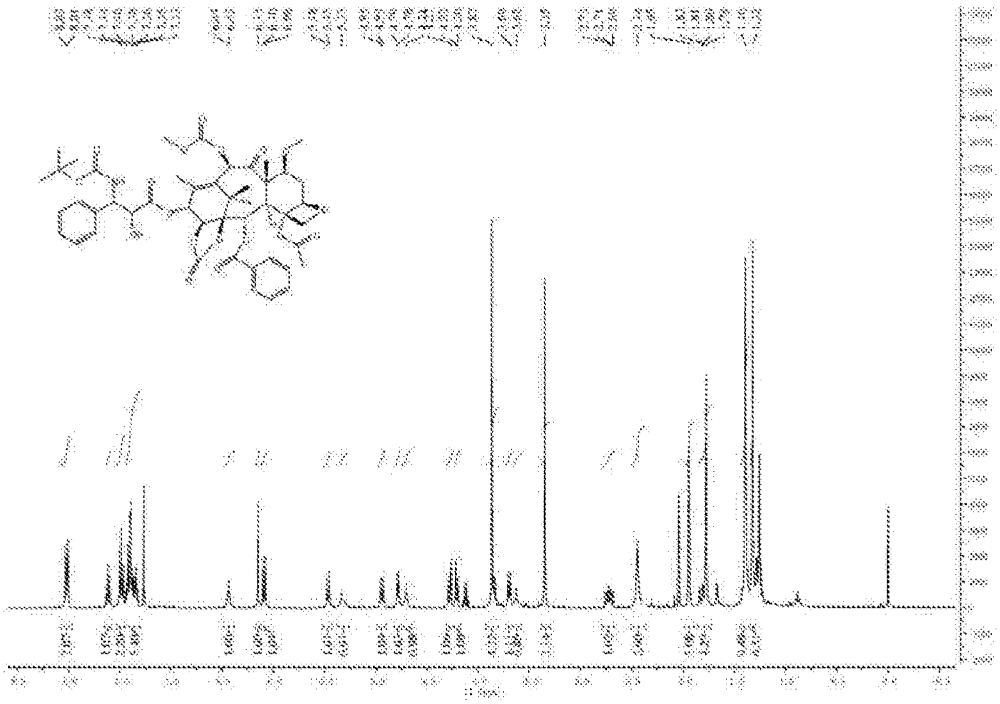
FIG. 34 is the $^1H$ NMR spectrum of PCMI-12.
Figure 35:
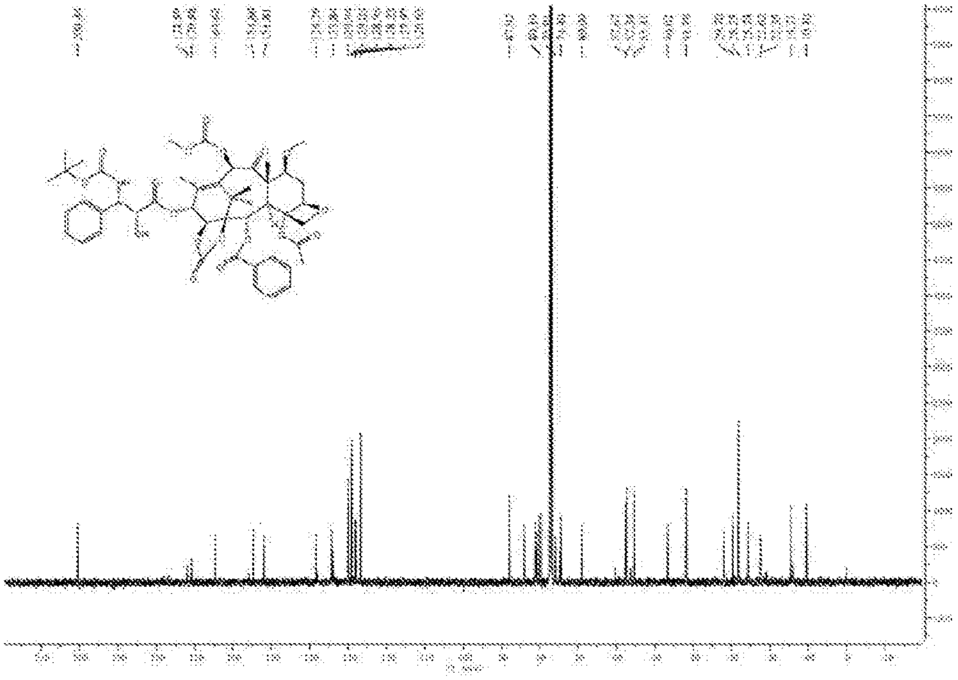
FIG. 35 is the $^{13}C$ NMR spectrum of PCMI-12.
Figure 36:
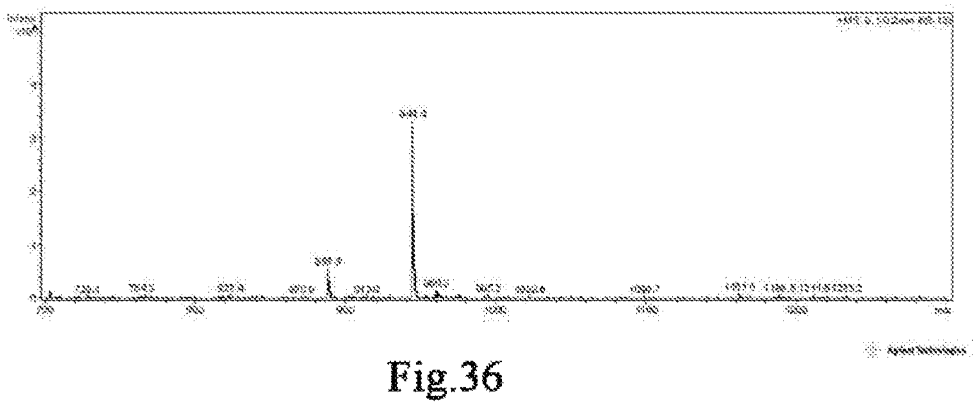
FIG. 36 is the MS spectrum of PCMI-12.
Figure 37:
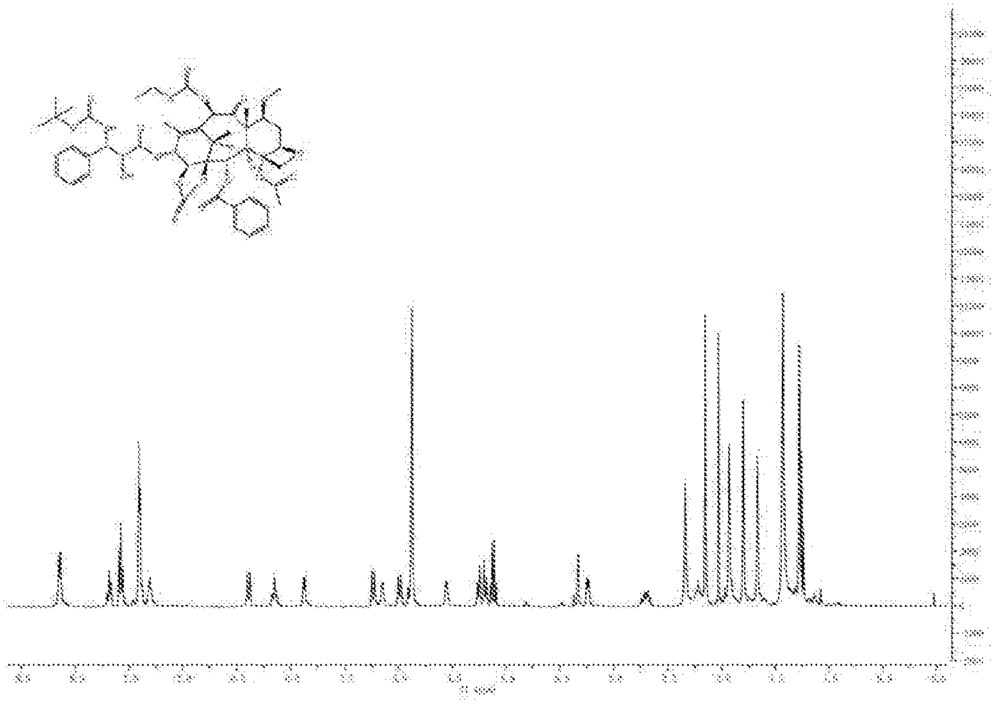
FIG. 37 is the $^1H$ NMR spectrum of PCMI-13.
Figure 38:
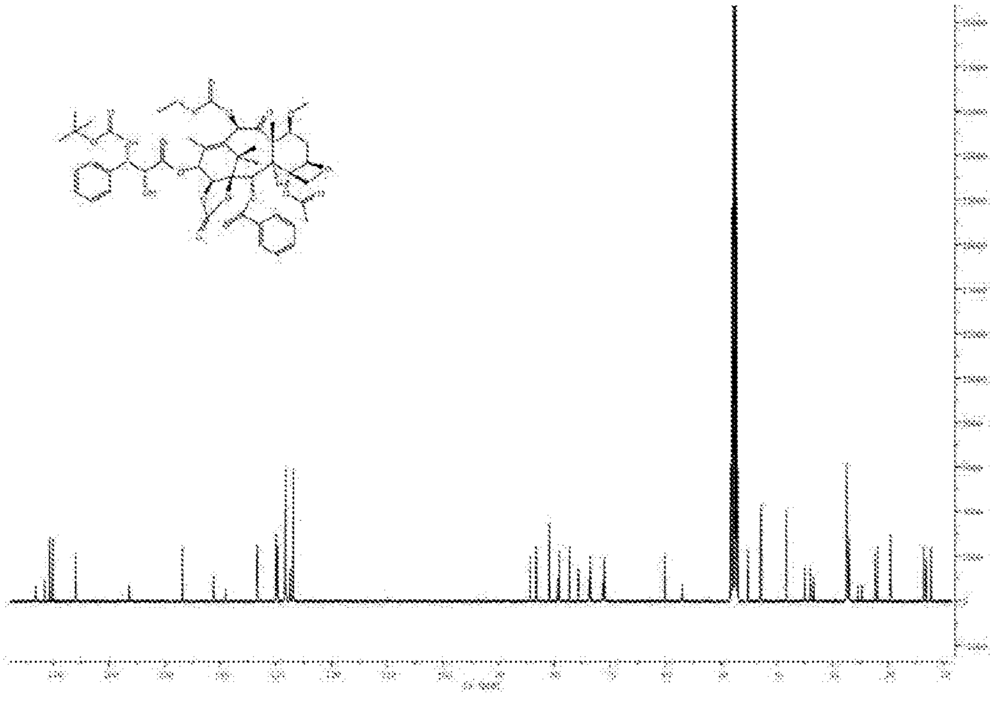
FIG. 38 is the $^{13}C$ NMR spectrum of PCMI-13.
Figure 39:
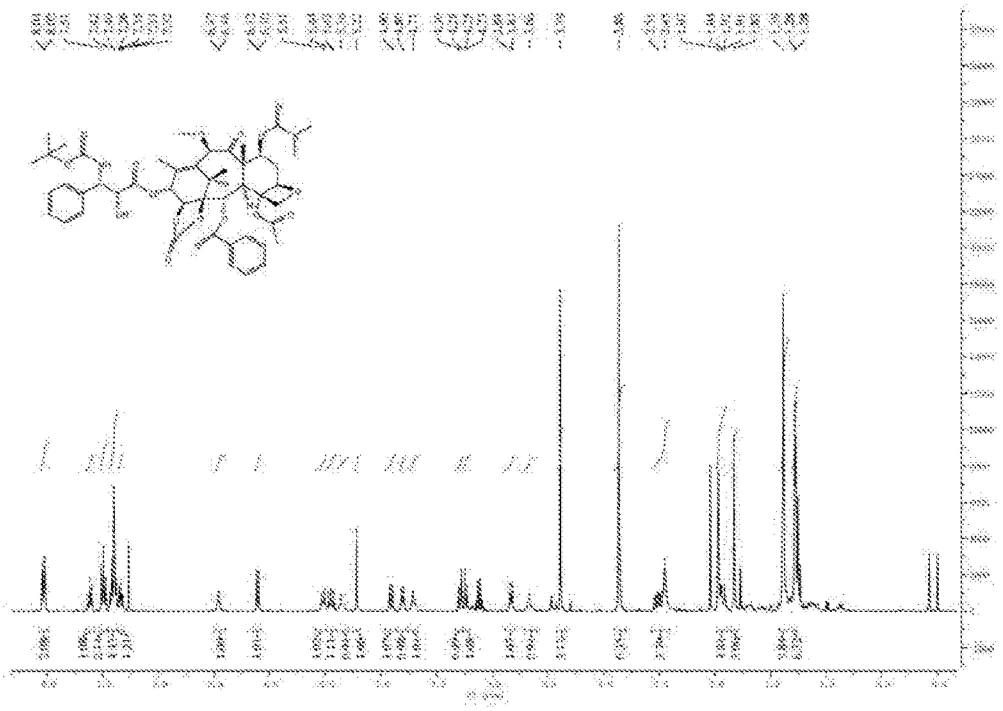
FIG. 39 is the $^1H$ NMR spectrum of PCMI-14.
Figure 40:
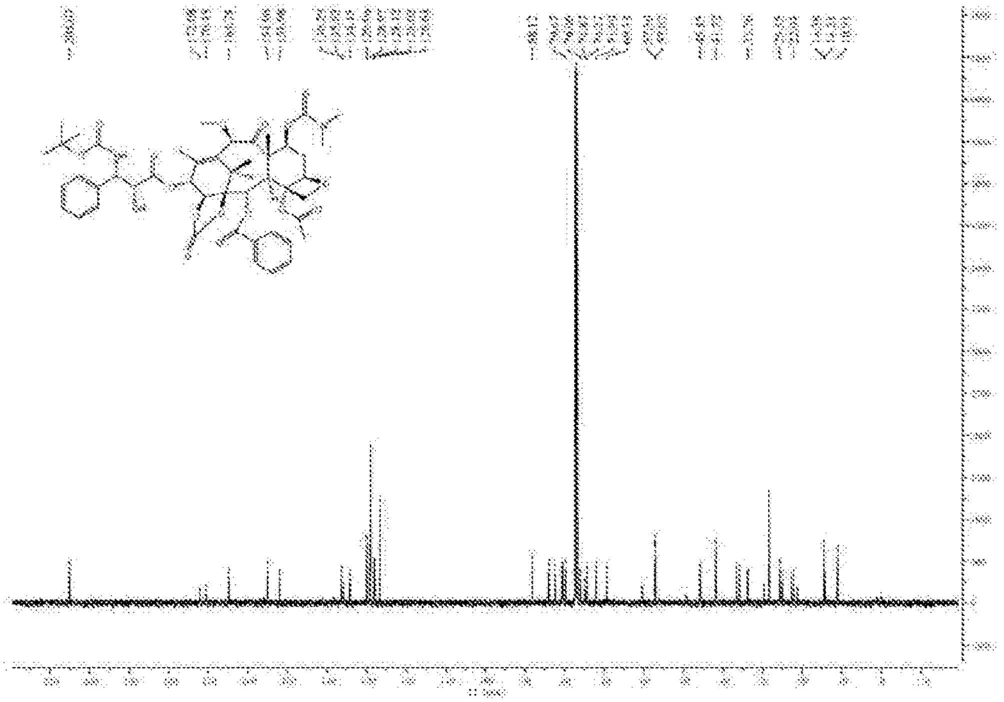
FIG. 40 is the $^{13}C$ NMR spectrum of PCMI-14.
Figure 41:
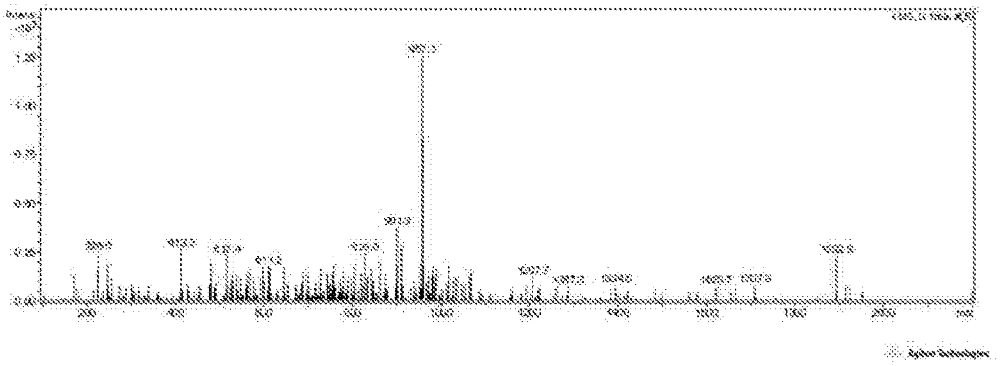
FIG. 41 is the MS spectrum of PCMI-14.
Figure 42:
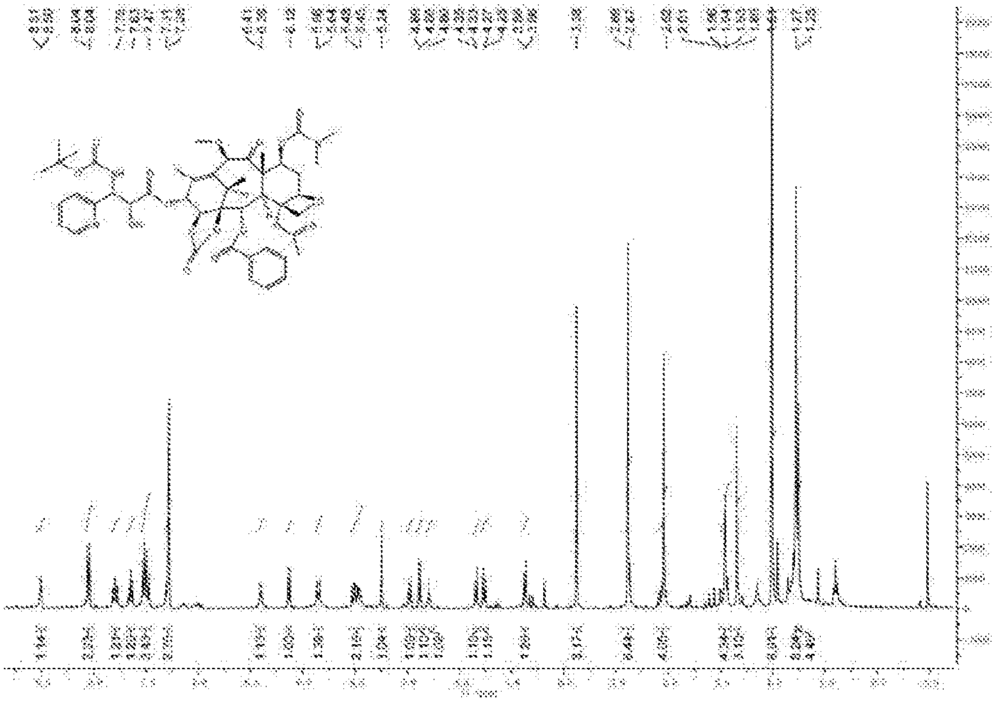
FIG. 42 is the $^1H$ NMR spectrum of PCMI-15.
Figure 43:
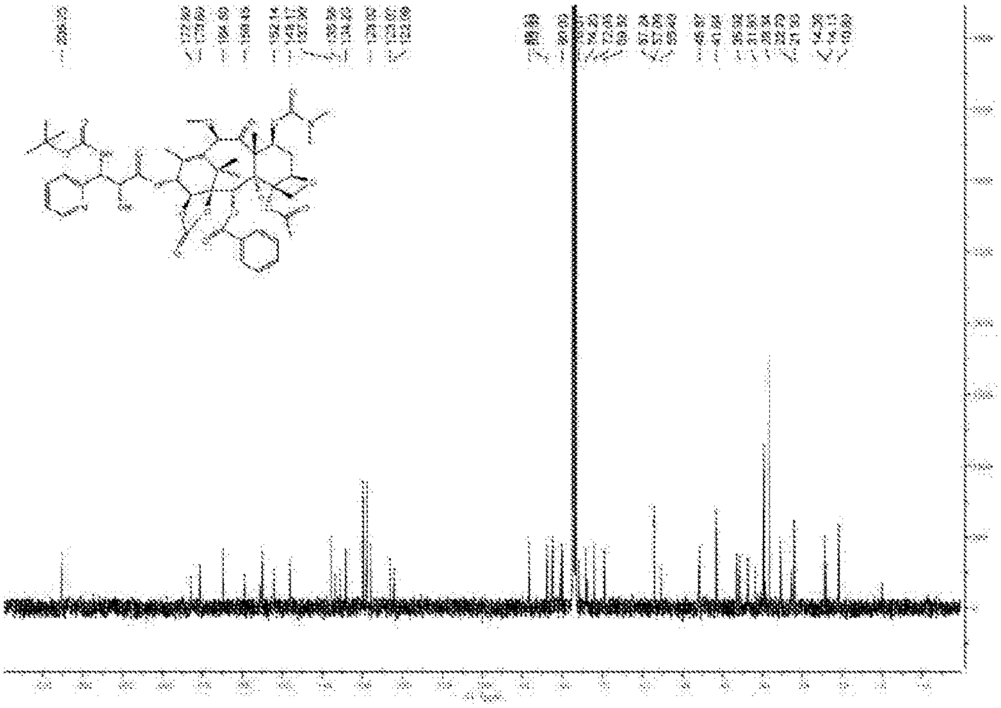
FIG. 43 is the $^{13}C$ NMR spectrum of PCMI-15.
Figure 44:
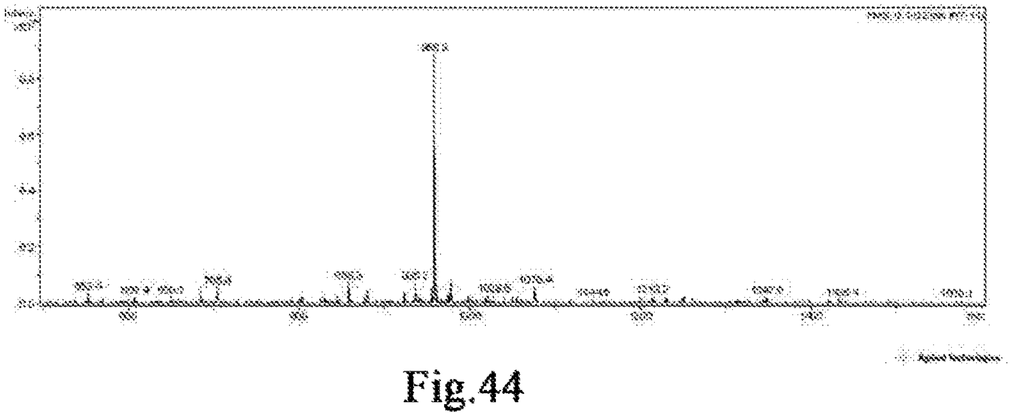
FIG. 44 is the MS spectrum of PCMI-15.
Figure 45:
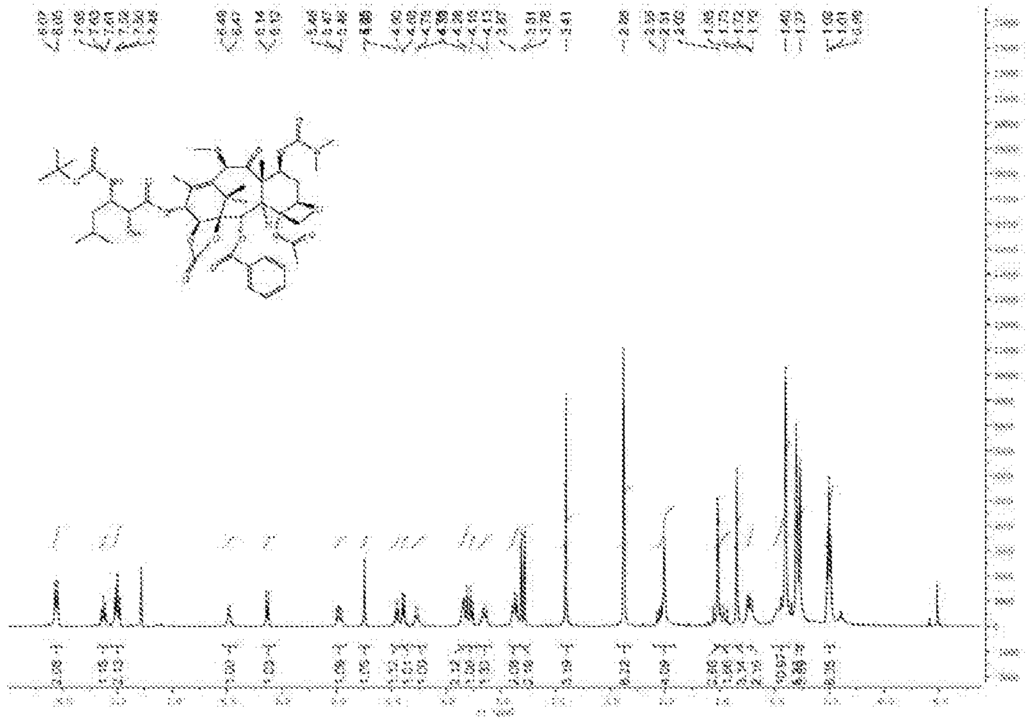
FIG. 45 is the $^1H$ NMR spectrum of PCMI-16.
Figure 46:
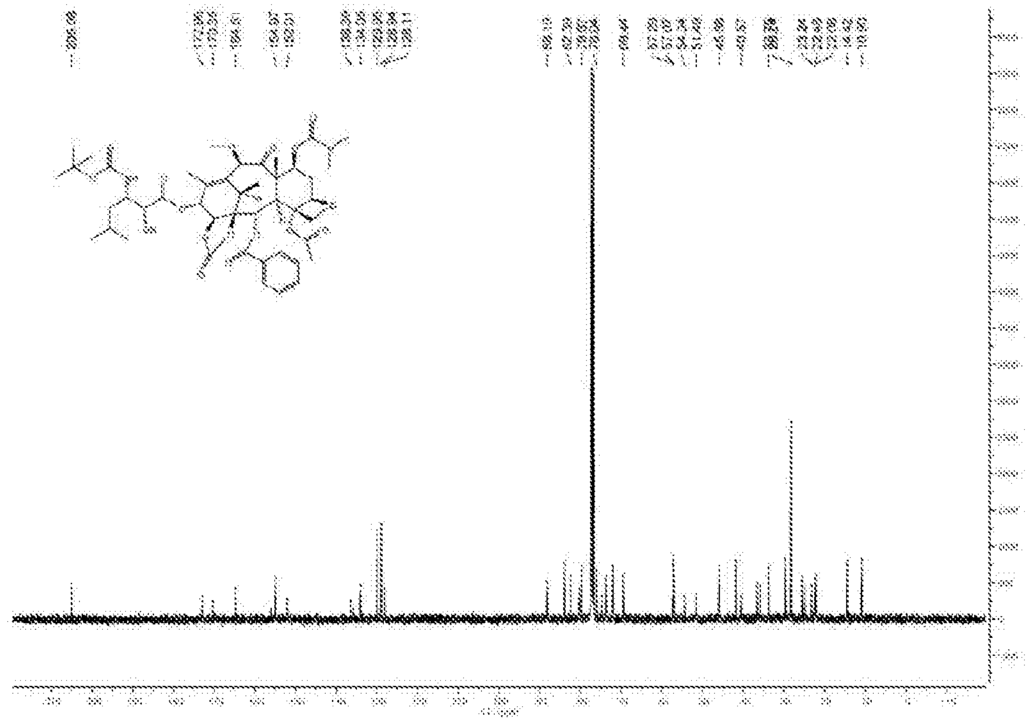
FIG. 46 is the $^{13}C$ NMR spectrum of PCMI-16.
Figure 47:
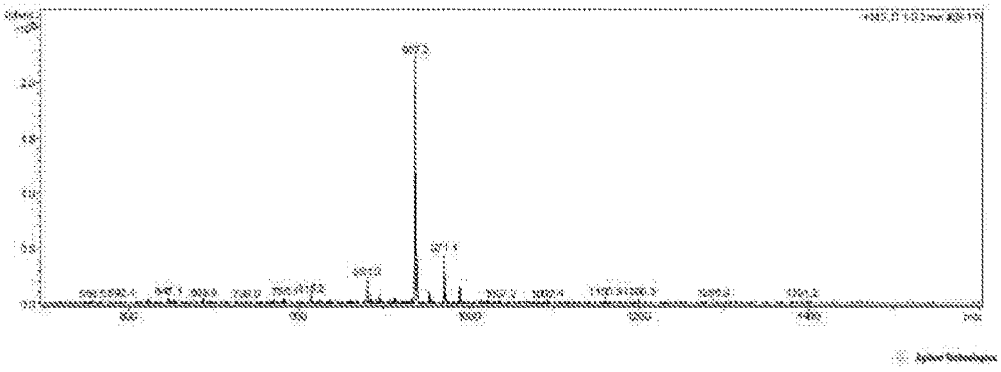
FIG. 47 is the MS spectrum of PCMI-16.
Figure 48:
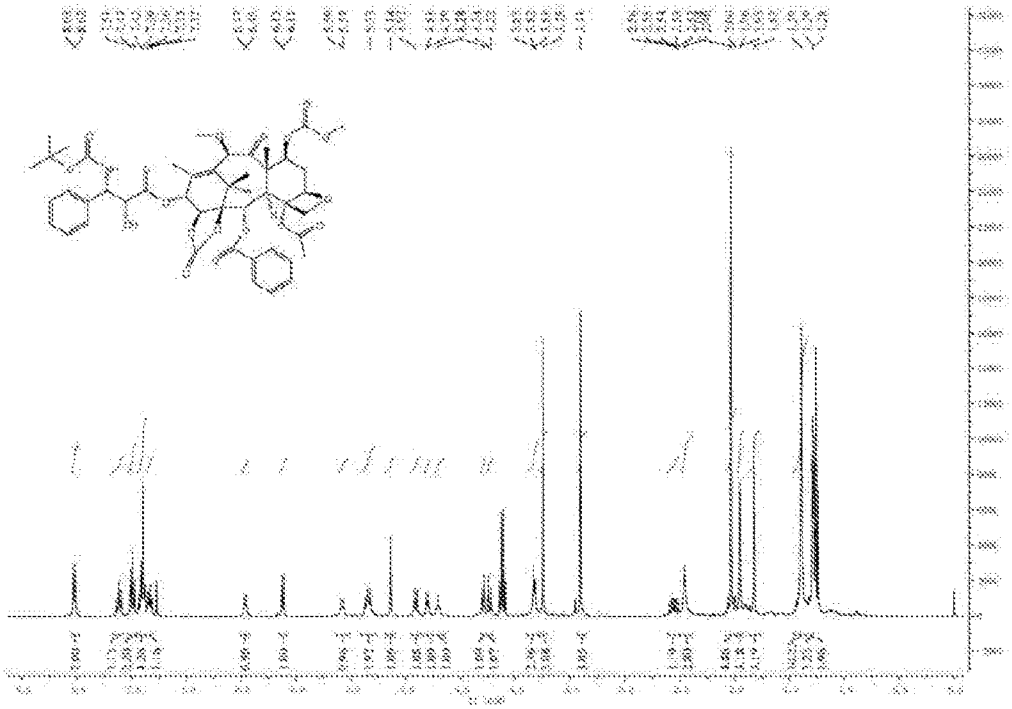
FIG. 48 is the $^1H$ NMR spectrum of PCMI-17.
Figure 49:
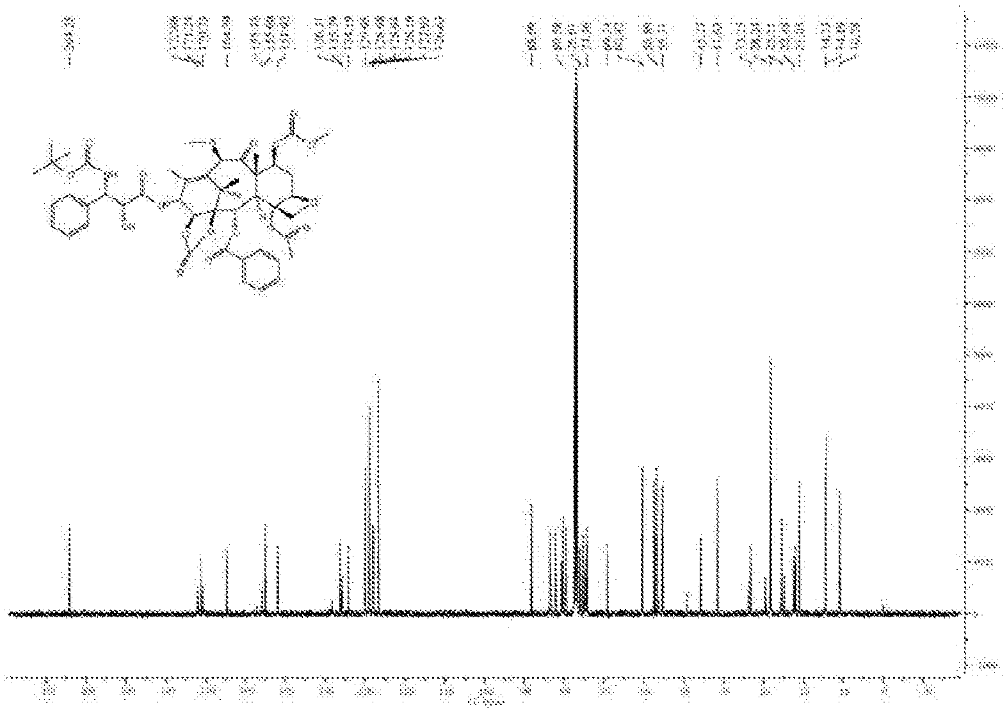
FIG. 49 is the $^{13}C$ NMR spectrum of PCMI-17.
Figure 50:
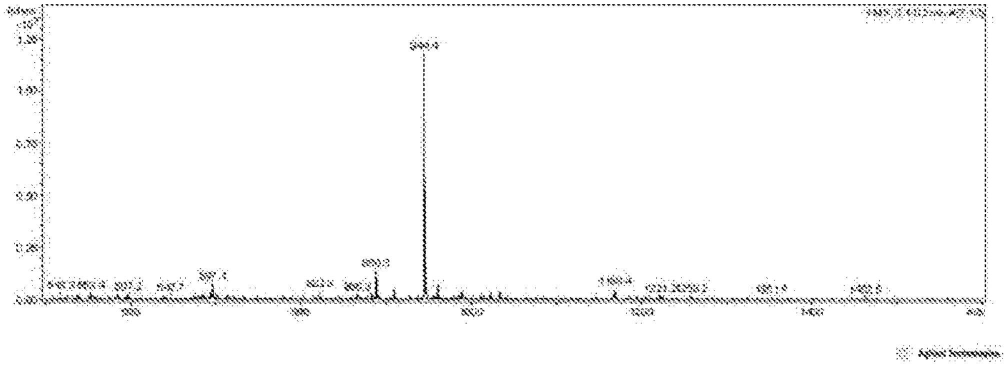
FIG. 50 is the MS spectrum of PCMI-17.
Figure 51:
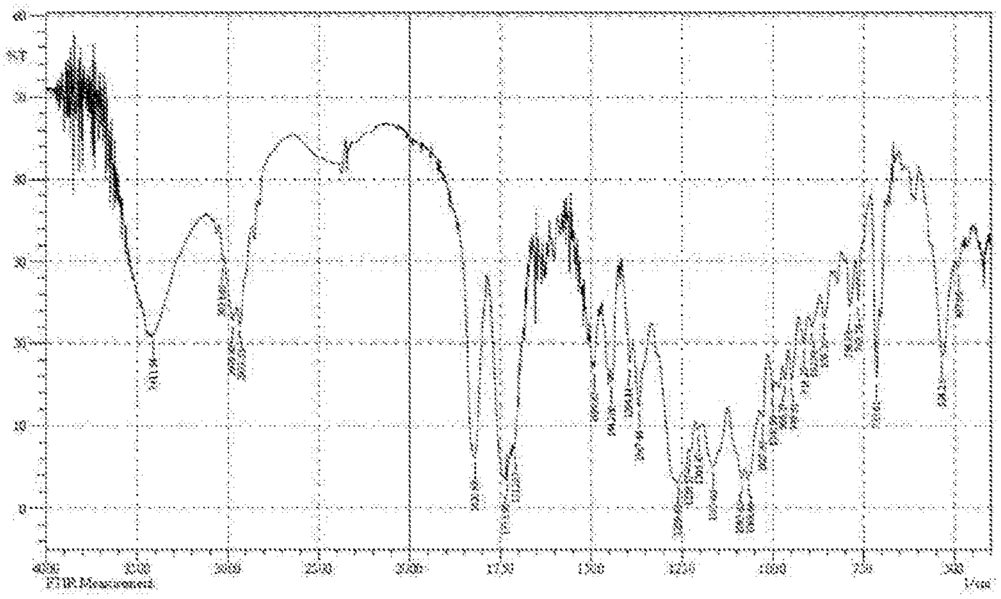
FIG. 51 is the IR spectrum of PCMI-17.
Figure 52:
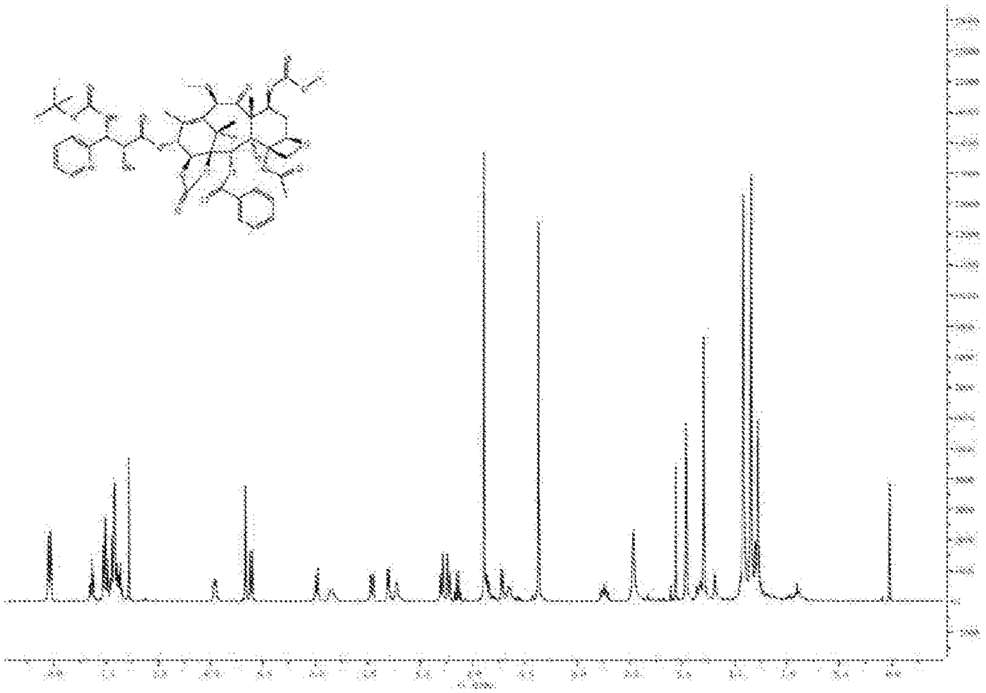
FIG. 52 is the $^1H$ NMR spectrum of PCMI-18.
Figure 53:
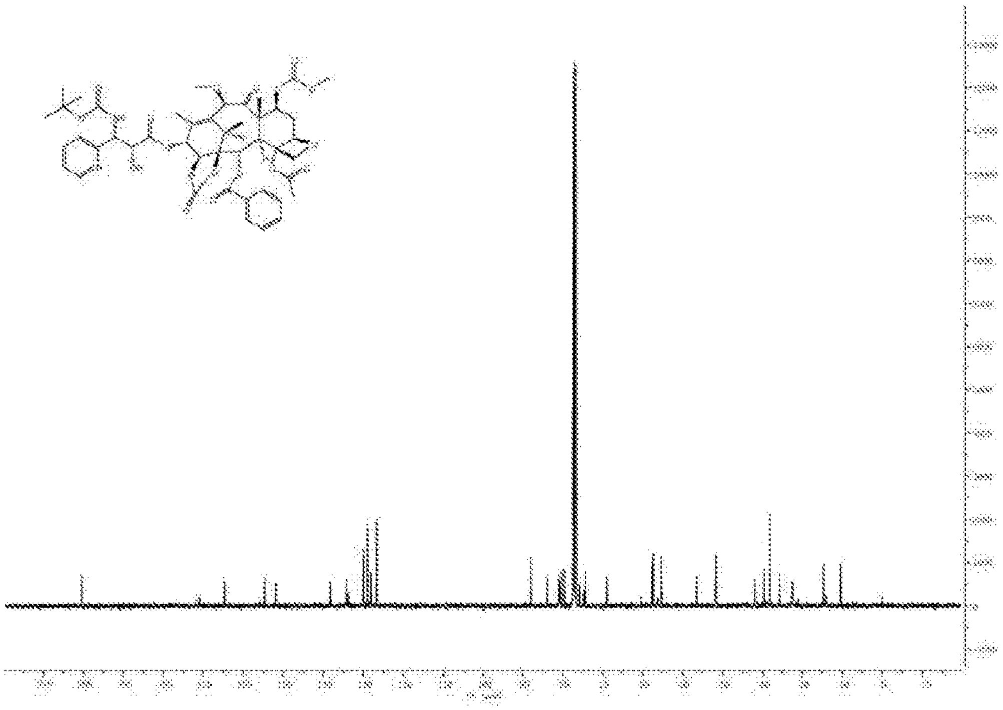
FIG. 53 is the $^{13}C$ NMR spectrum of PCMI-18.
Figure 54:
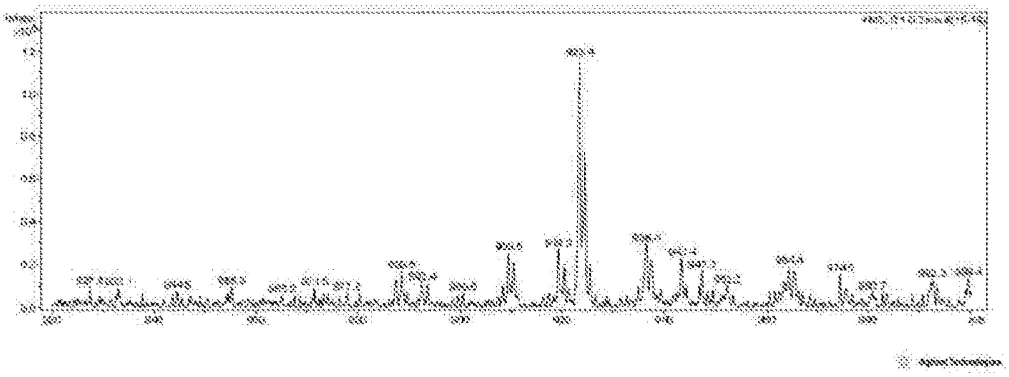
FIG. 54 is the MS spectrum of PCMI-18.
Figure 55:
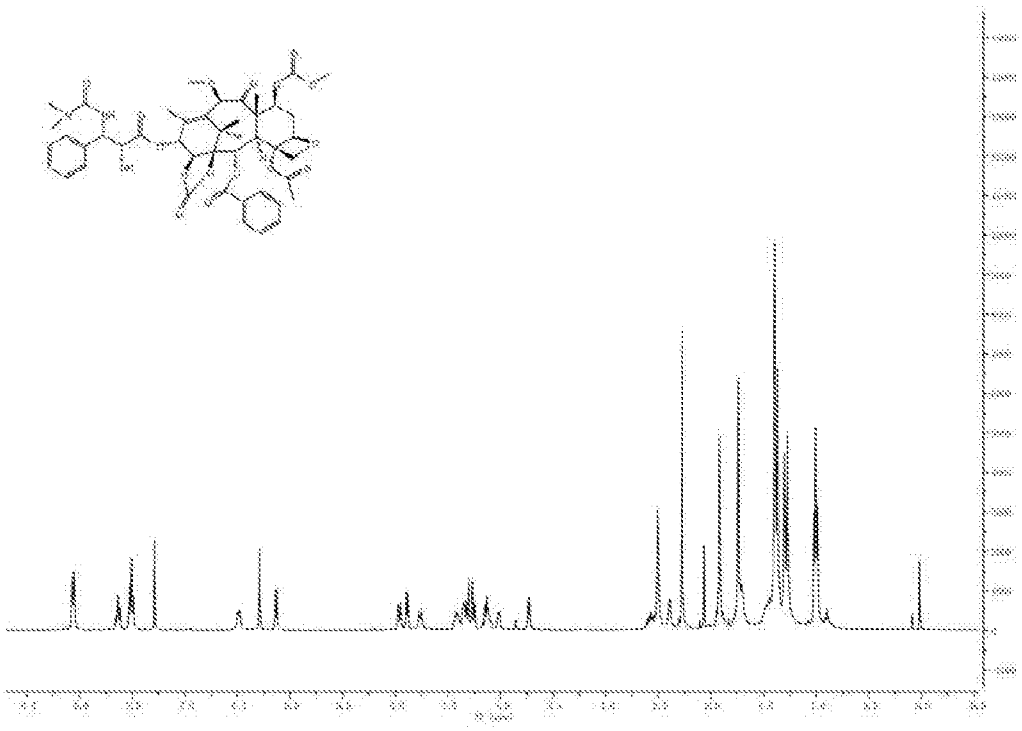
FIG. 55 is the $^1H$ NMR spectrum of PCMI-19.
Figure 56:
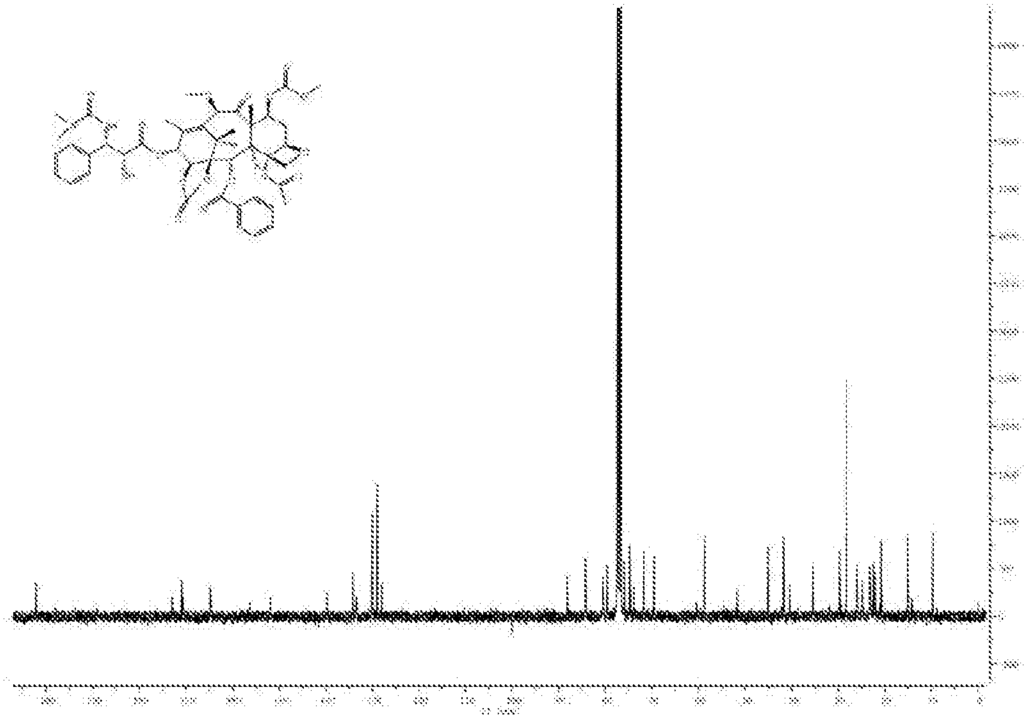
FIG. 56 is the $^{13}C$ NMR spectrum of PCMI-19.
Figure 57:
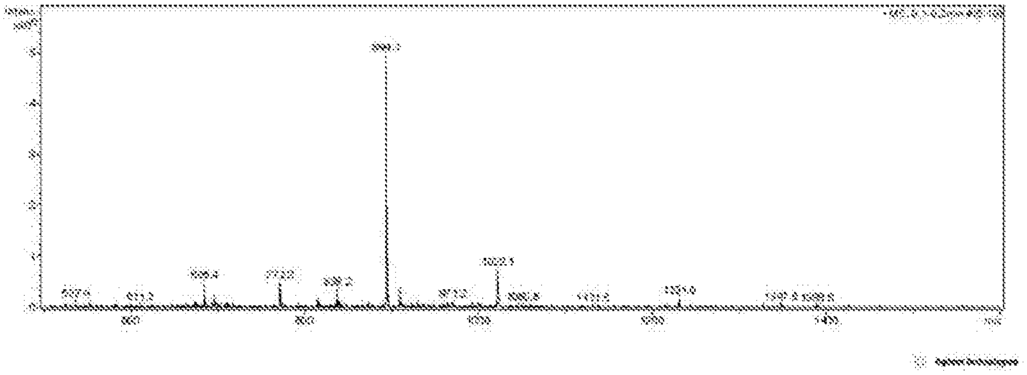
FIG. 57 is the MS spectrum of PCMI-19.
Figure 58:
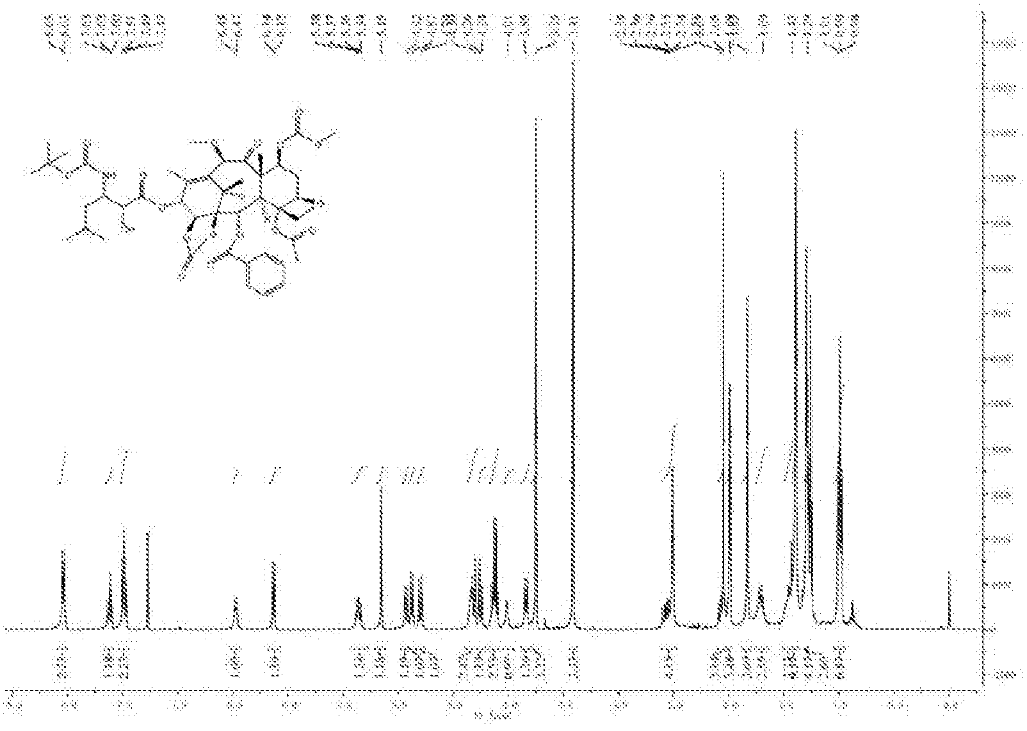
FIG. 58 is the $^1H$ NMR spectrum of PCMI-20.
Figure 59:
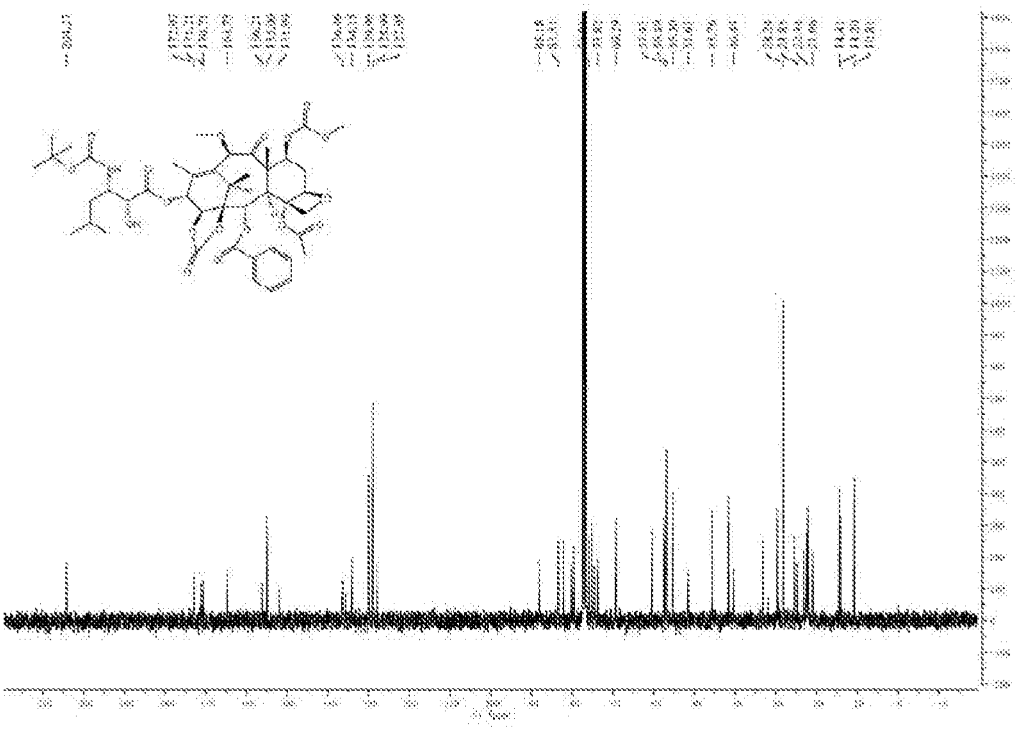
FIG. 59 is the $^{13}C$ NMR spectrum of PCMI-20.
Figure 60:
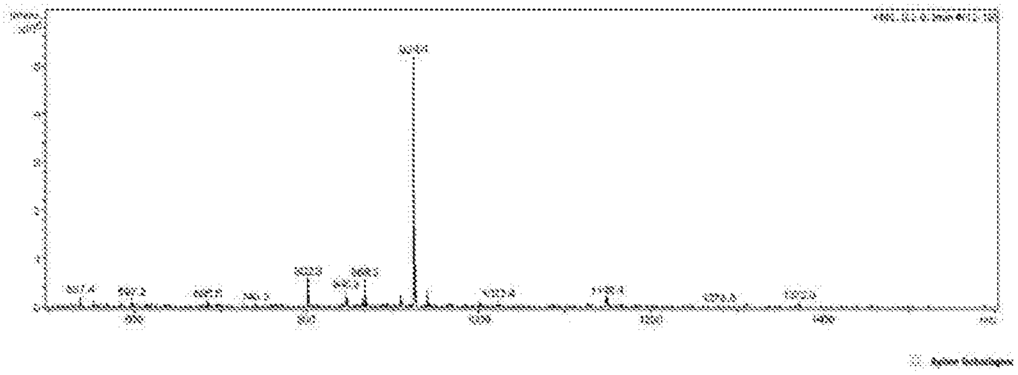
FIG. 60 is the MS spectrum of PCMI-20.
Figure 61:
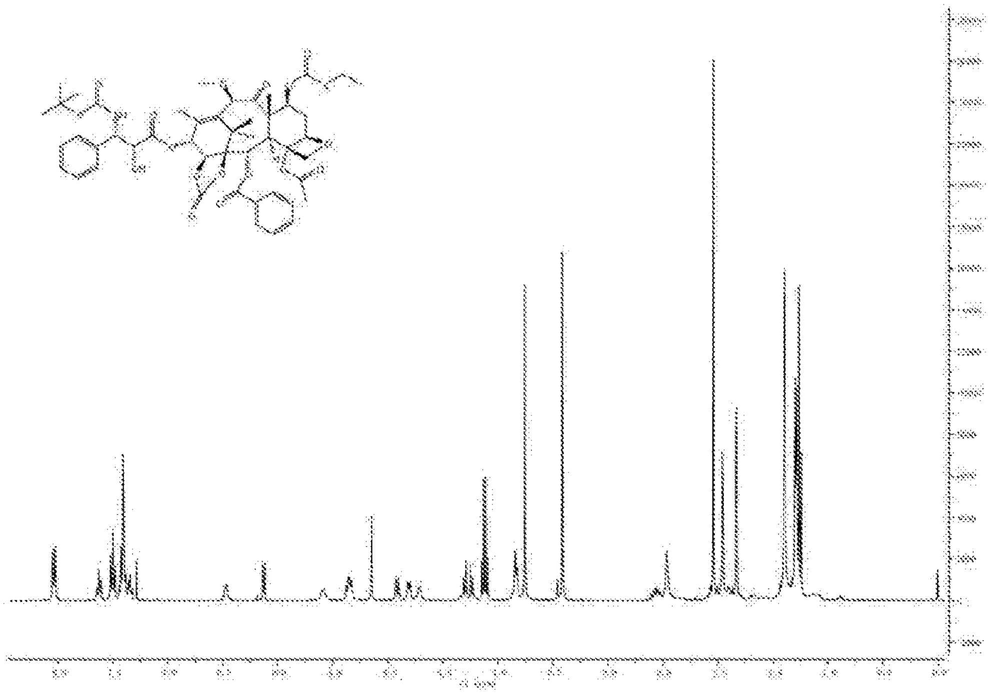
FIG. 61 is the $^1H$ NMR spectrum of PCMI-21.
Figure 62:
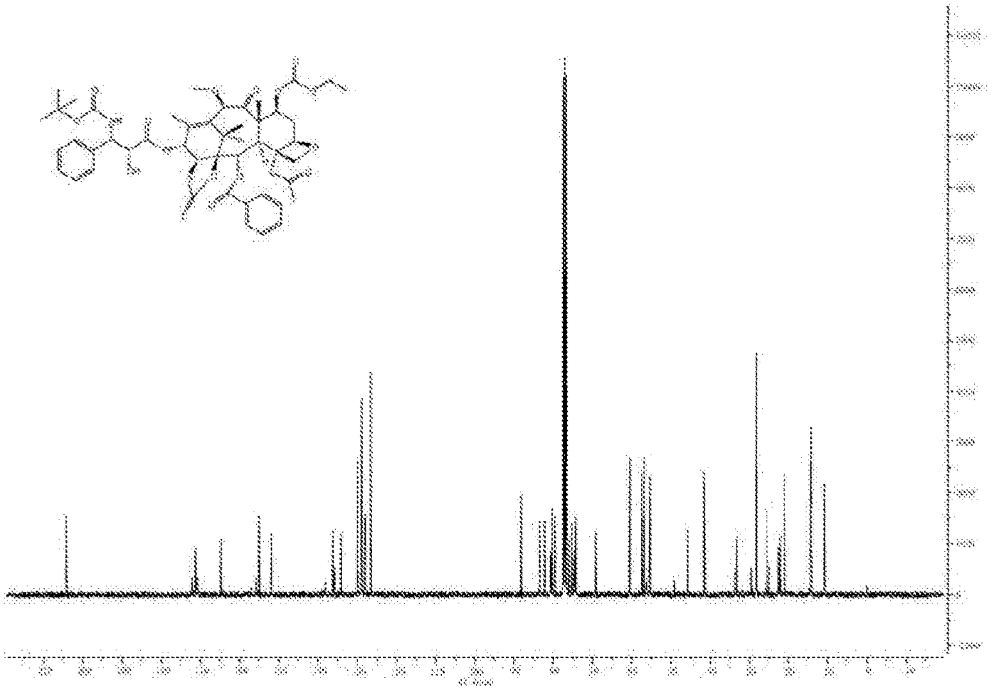
FIG. 62 is the $^{13}C$ NMR spectrum of PCMI-21.

The term "alkyl" used herein refers to the group consisting of carbon and hydrogen atoms only without any unsaturated degree (such as double bonds, triple bonds or rings), which covers all kinds of possible geometric isomers and stereo-isomers thereof. The groups are attached to the rest of the molecule by a single bond. The term "C1-C6 alkyl" used herein refers to the above defined alkyl with a carbon number of 1-6. As non-limiting examples of C1-C6 alkyl, the following groups with straight chain or branched chain may be enumerated: methyl, ethyl, n-propyl, isopropyl, n-butyl, isobutyl, sec-butyl, t-butyl, n-pentyl and isomers thereof, as well as n-hexyl and isomers thereof.

The term "alkenyl" used herein refers to the group which is formed from the above mentioned alkyl group (except methyl) by having one or more double bonds. The term "C1-C6 alkenyl" refers to the above defined alkenyl with a carbon number of 1-6.

The term "alkynyl" used herein refers to the group which is formed from the above mentioned alkyl group (except methyl) by having one or more triple bonds. The term "C1-C6 alkynyl" refers to the above defined alkynyl with a carbon number of 1-6.

The term "hydrocarbon group" used herein refers to the group consisting of carbon and hydrogen atoms only. The term "substituted hydrocarbon group" refers to the above defined alkyl, alkenyl or alkynyl group and the like having substituents. The substituent can be a hydroxyl group, an amino group and the like.

The term "heterocyclic group" used herein refers to an aromatic 5-14 member ring or a non-aromatic 3-15 member ring consisting of carbon atoms and heteroatoms independently selected from N, O or S. The aromatic ring may be monocyclic, bicyclic or polycyclic, in which the bicyclic and polycyclic groups are formed from monocyclic groups by connected with each other through single bonds or in a fused way. As non-limiting examples of heteroaryl groups, the following groups may be enumerated: oxazolyl, isoxazolyl, imidazolyl, furyl, indolyl, isoindolyl, pyrrolyl, triazolyl, triazinyl, tetrazolyl, thienyl, thiazolyl, isothiazolyl, pyridinyl, pyrimidinyl, pyrazinyl, pyridazinyl, benzofuranyl, benzothiazolyl, benzoxazolyl, benzimidazolyl, benzothienyl, benzopyranyl, carbazolyl, quinolinyl, isoquinolinyl, quinazolinyl, cinnolinyl, naphthyridinyl, pteridinyl, purinyl, quinoxalinyl, thiadiazolyl, indolizinyl, acridinyl, phenazinyl, phthalazinyl, coumarinyl, pyrazolopyridinyl, pyridinopyridazinyl, pyrrolopyridinyl, imidazopyridinyl, pyrazolopyridazinyl; and the groups formed from the above heteroaryl groups by connected with each other through single bonds or in a fused way. The non-aromatic ring may be monocyclic, bicyclic or polycyclic, and fused ring, bridged ring or spiro ring, which may optionally contain one or more double bonds. As non-limiting examples of the heterocyclic groups, the following groups may be enumerated: azepinyl, acridinyl, benzodioxolyl, benzodioxanyl, chromanyl, dioxolanyl, dioxaphospholanyl, decahydro isoquinolinyl, indanyl, indolinyl, isoindolinyl, isochromanyl, isothiazolidinyl, isoxazolidinyl, morpholinyl, oxazolinyl, oxazolidinyl, oxadiazolyl, 2-oxo-piperazinyl, 2-oxo-piperidinyl, 2-oxopyrrolidinyl, 2-oxo-azepinyl, octahydroindolyl, octahydroisoindolyl, perhydroazepinyl, piperazinyl, 4-piperidonyl, piperidinyl, phenothiazinyl, phenoxazinyl, quinuclidinyl, tetrahydroisoquinolinyl, tetrahydrofuranyl, tetrahydropyranyl, tetrahydropyrrolidinyl, thiazolinyl, thiazolidinyl, thiomorpholinyl, thiomorpholine sulfoxide and thiomorpholinyl sulfone.

The term "aryl" used herein refers to an aromatic ring consisting of at least 6 carbon atoms, which may be monocyclic, bicyclic or polycyclic, in which bicyclic and polycyclic rings may be formed from monocyclic rings by connected with each other through single bonds or in a fused way. As non-limiting examples of the aryl groups, the following groups may be enumerated: phenyl, naphthyl, anthryl, phenanthryl, indenyl, pyrenyl, perylenyl, azulenyl, acenaphthenyl, fluorenyl, benzoacenaphthenyl, triphenylenyl, chrysenyl, biphenyl, binaphthyl and the like.

The term "substituted aromatic group" used herein refers to the above defined aromatic group having substituents. The substituent may be an alkyl, an alkenyl, an alkynyl, a hydroxyl, an amino and the like.

The present invention provides taxanes compounds having the structure represented by the following general formula I:

I

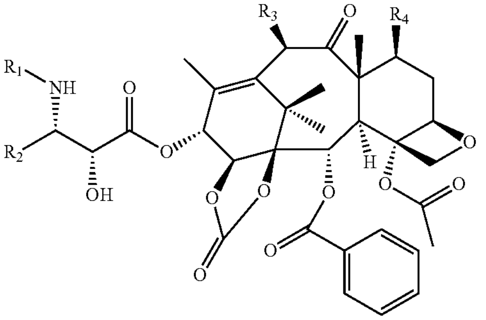

wherein, $R_1$ is —$COR_6$, —$COOR_6$, or —$CONR_{7a}R_{7b}$;

$R_2$ is a C1-C6 alkyl, a C1-C6 alkenyl group, a substituted hydrocarbon group, a heterocyclic group, an aromatic group or a substituted aromatic group;

$R_3$ is —$OR_6$, —$OCOOR_6$, —$OCOSR_6$, or —$OCONR_{7a}R_{7b}$;

$R_4$ is —$OR_6$, —$OCOOR_6$, —$OCOSR_6$, —$OCONR_{7a}R_{7b}$, H or OH;

wherein, $R_6$ is a C1-C6 alkyl, a C1-C6 alkenyl, a C1-C6 alkynyl, a substituted hydrocarbon group, an aromatic group or a heterocyclic group; $R_{7a}$ and $R_{7b}$ are respectively hydrogen, a hydrocarbon group, a substituted hydrocarbon group or a heterocyclic group.

Preferably, $R_1$ is benzoyl, t-butyloxycarbonyl, or N,N'-dimethylcarbamoyl;

$R_2$ is phenyl,

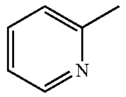 , or 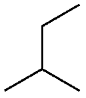 ;

$R_3$ is —OMe, —$OCOOCH_3$, —$OCON(CH_3)_2$, or —$OCOSC_2H_5$;

$R_4$ is —OMe, —$OCOOCH_3$, —$OCON(CH_3)_2$, —$OCOSC_2H_5$, H or OH.

Most preferably, the taxanes compounds of the present invention are selected from the compounds having the following structures:

| Code | MW | Formula | Structure |
|---|---|---|---|
| PCMI-01 | 877 | $C_{46}H_{55}NO_{16}$ | 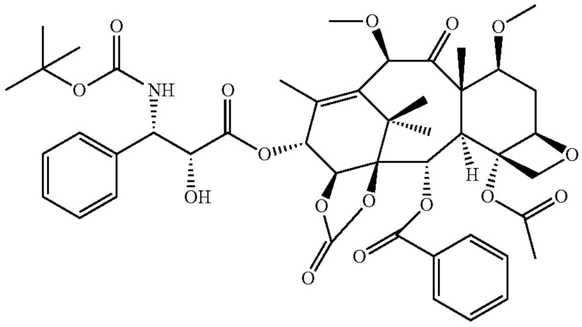 |

-continued
| Code | MW | Formula | Structure |
|---|---|---|---|
| PCMI-02 | 881 | $C_{48}H_{51}NO_{15}$ | 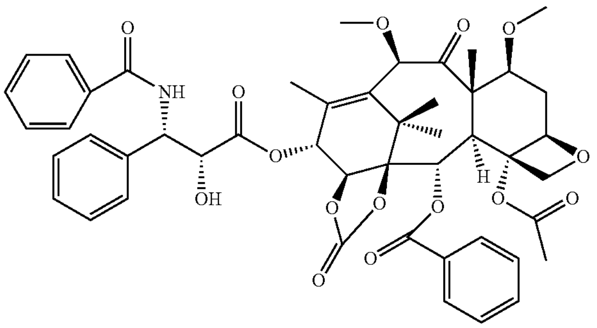 |
| PCMI-03 | 848 | $C_{44}H_{52}N_2O_{15}$ | 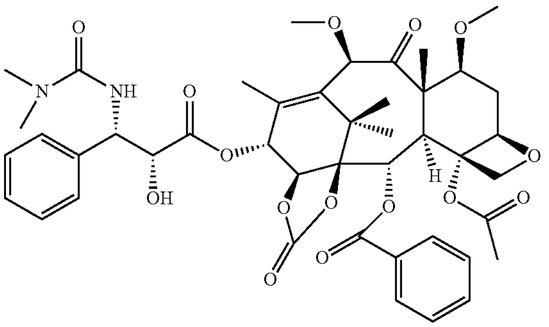 |
| PCMI-04 | 878 | $C_{45}H_{54}N_2O_{16}$ | 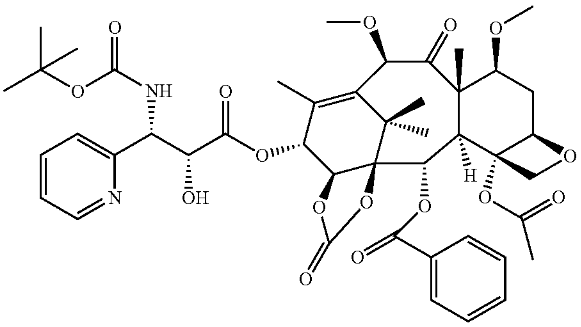 |
| PCMI-05 | 857 | $C_{44}H_{59}NO_{16}$ | 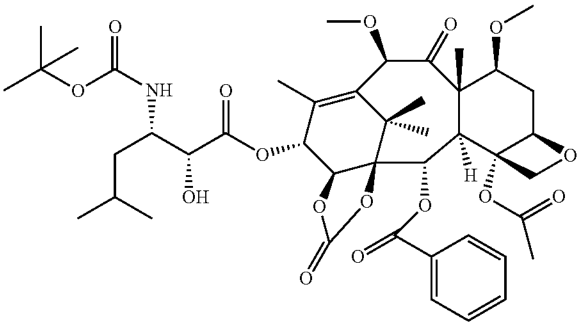 |

-continued
| Code | MW | Formula | Structure |
| --- | --- | --- | --- |
| PCMI-06 | 863 | $C_{45}H_{53}NO_{16}$ | 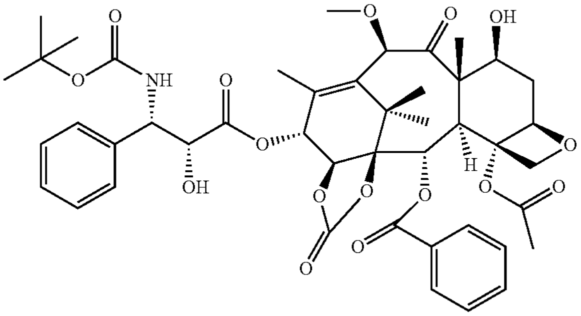 |
| PCMI-07 | 847 | $C_{45}H_{53}NO_{15}$ | 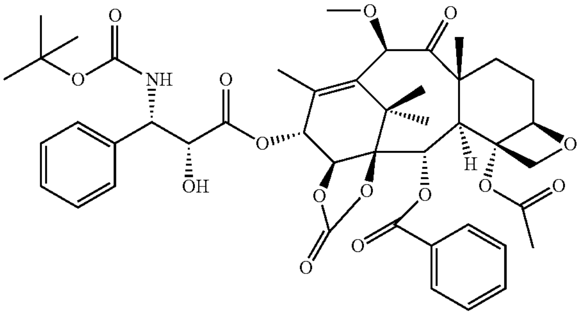 |
| PCMI-08 | 934 | $C_{48}H_{58}N_2O_{17}$ | 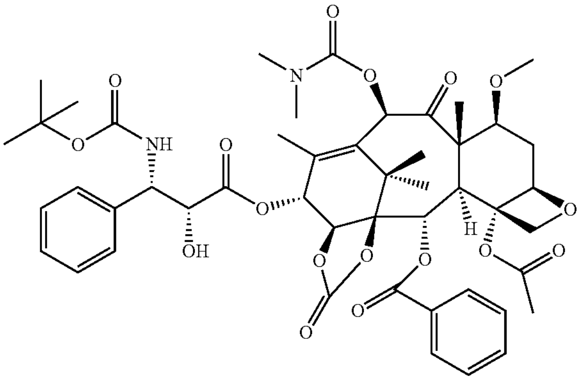 |
| PCMI-09 | 935 | $C_{47}H_{57}N_3O_{17}$ | 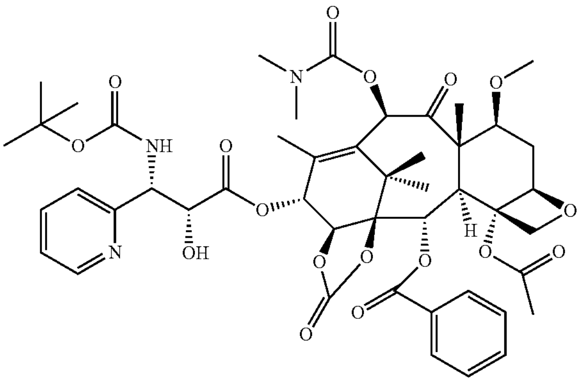 |

-continued
| Code | MW | Formula | Structure |
|---|---|---|---|
| PCMI-10 | 914 | $C_{46}H_{62}N_2O_{17}$ | 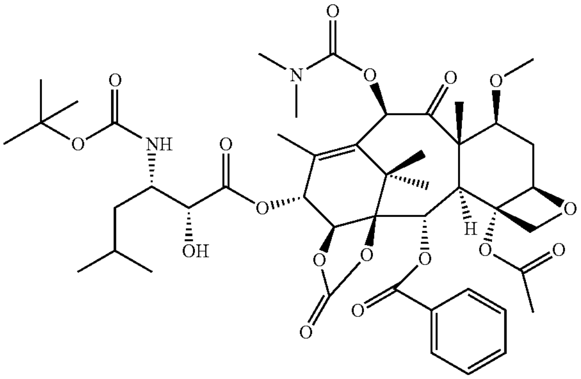 |
| PCMI-11 | 905 | $C_{46}H_{55}N_3O_{16}$ | 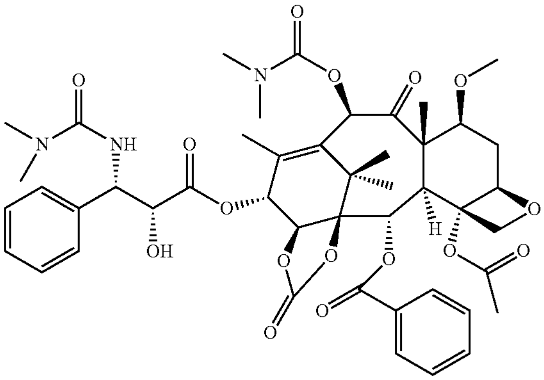 |
| PCMI-12 | 921 | $C_{47}H_{55}NO_{18}$ | 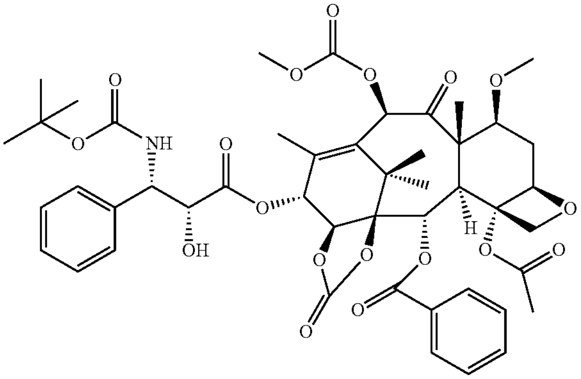 |
| PCMI-13 | 951 | $C_{48}H_{57}NO_{17}S$ | 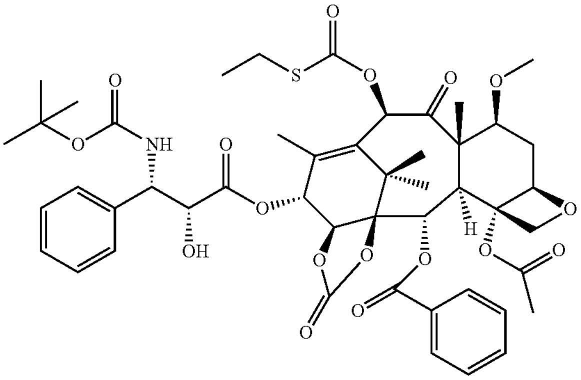 |

-continued
| Code | MW | Formula | Structure |
|---|---|---|---|
| PCMI-14 | 934 | $C_{48}H_{58}N_2O_{17}$ | 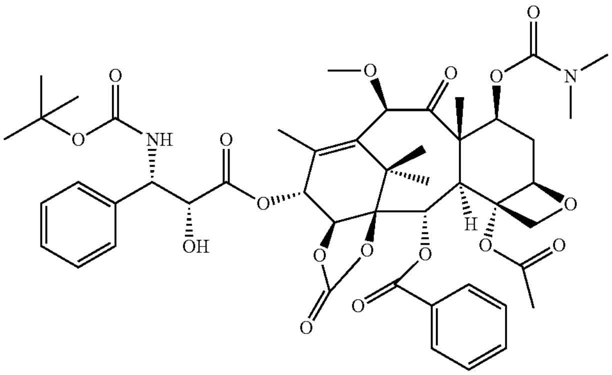 |
| PCMI-15 | 935 | $C_{47}H_{57}N_3O_{17}$ | 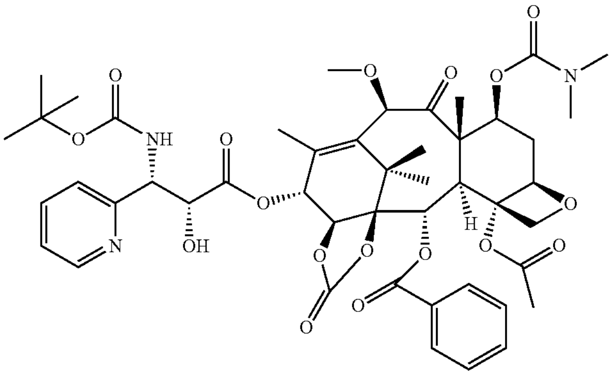 |
| PCMI-16 | 914 | $C_{46}H_{62}N_2O_{17}$ | 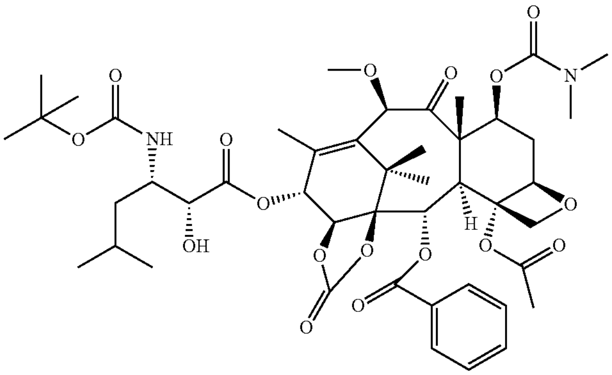 |
| PCMI-17 | 921 | $C_{47}H_{55}NO_{18}$ | 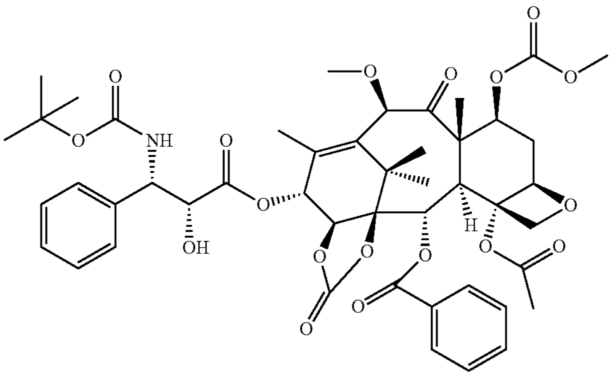 |

-continued
| Code | MW | Formula | Structure |
|---|---|---|---|
| PCMI-18 | 922 | $C_{46}H_{54}N_2O_{18}$ | 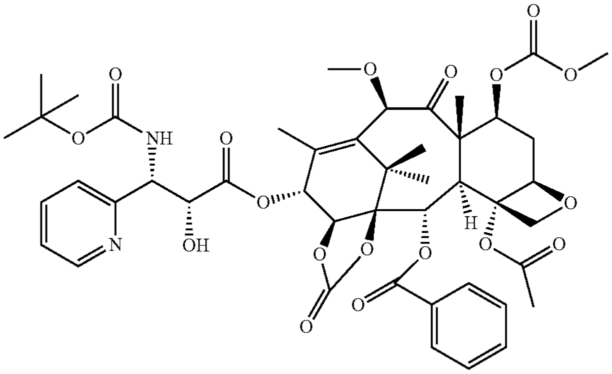 |
| PCMI-19 | 892 | $C_{45}H_{52}N_2O_{17}$ | 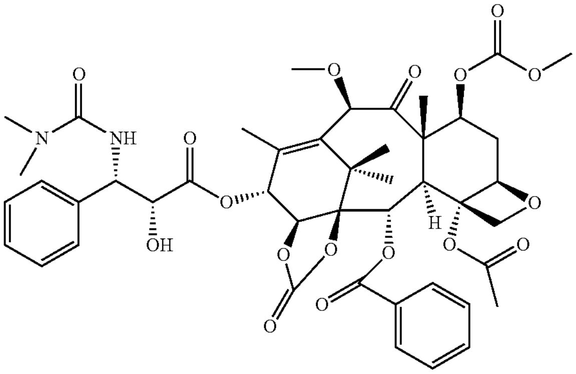 |
| PCMI-20 | 901 | $C_{45}H_{59}NO_{18}$ | 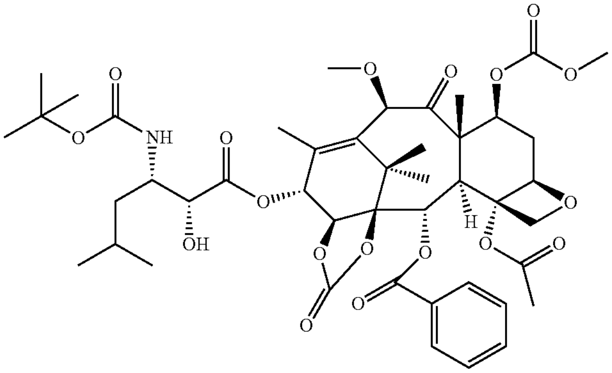 |
| PCMI-21 | 951 | $C_{48}H_{57}NO_{17}S$ | 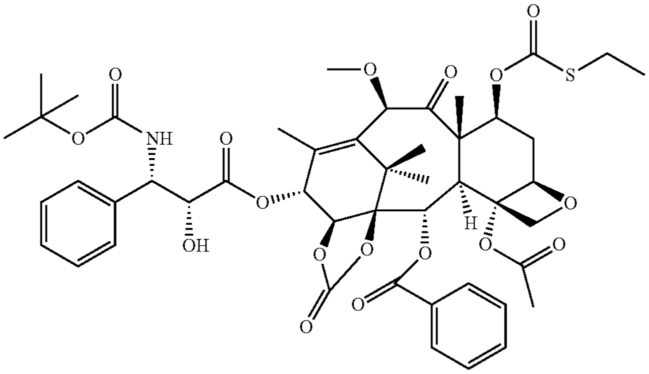 |

According to the present invention, the compounds having the structures represented by the general formula (I) also include all isomers of these compounds and mixtures of the isomers.

If necessary, the compounds having the structures represented by the general formula (I) may be formed into a pharmaceutically acceptable non-toxic salts.

According to the present invention, the compounds having the structures represented by the general formula (I) may optionally exist in the form of solvates (such as hydrates). Therefore, these solvates (such as hydrates) are also included within the compounds of the present invention.

Furthermore, the present invention provides a pharmaceutical composition comprising the compounds having the structures represented by the above defined general formula (I), the pharmaceutically acceptable salts or solvates thereof as active ingredients, as well as and the use thereof in manufacturing oral antitumor medicaments.

In the pharmaceutical composition of the present invention, the weight ratio of the compounds of the present invention is 0.01%-99.99% with the balance of pharmaceutically acceptable carriers. The pharmaceutical composition is in the form of suitable preparations. The preparations include: tablets, capsules, granules, pills, powders, slurries, suspensions, injections, powder-injections, suppositories, creams, drops or patches. Wherein, the tablets are sugar-coated tablets, film-coated tablets, enteric coated tablets or sustained release tablets; the capsules are hard capsules, soft capsules or sustained release capsules; the powder-injections are lyophilized powder-injections.

In the dosage form of the pharmaceutical composition of the present invention, each dosage form contains an effective amount of 0.1 mg-1000 mg of the compounds of the present invention. Wherein, each dosage form refers to each unit thereof, e.g. each tablet in tablets, each capsule in capsules. Alternatively, it can also refer to the dose administrated at each time (e.g. a dose of 100 mg at each time).

The solid carriers may be used, when the pharmaceutical composition of the present invention is prepared into solid or semi-solid preparations such as powders, tablets, dispersible powders, capsules, cachets, suppositories and ointments. The usable solid carrier is preferably selected from one or more substances of diluents, flavors, solubilizers, lubricants, suspending agents, binders, bulking agents and the like, or may be encapsulating materials. In powder preparations, it contains 5-70 wt % of the micronized active ingredient in the carriers. Suitable solid carriers include magnesium carbonate, magnesium stearate, talc powder, sucrose, lactose, pectin, dextrin, starch, gelatin, methyl cellulose, sodium carboxymethyl cellulose, low boiling point wax, cocoa butter and the like. Since tablets, powders, cachets and capsules are easily to be administrated, they represent the most advantageous oral solid preparations.

The liquid preparations of the present invention include solutions, suspensions and emulsions. For example, the injection preparations for parenteral administration can be in the form of water solution or water-propylene glycol solution, which is used to adjust isotonicity, pH, etc., making it adapted to the physiological conditions of the living body. Alternatively, liquid preparations can be prepared in the form of polyethylene glycol or water solution. The oral water solution can be prepared by dissolving the active ingredients in water and adding appropriate amounts of colorants, flavors, stabilizing agents and thickening agents therein. In addition, the oral water suspensions can be prepared by dispersing the micronized active ingredients into viscous materials, such as natural and synthetic gums, methylcellulose, sodium carboxymethyl cellulose and other known suspending agents.

For convenience of administration and dose uniformity, it is particularly advantageous to prepare the aforementioned pharmaceutical preparations in the form of a preparation unit. The preparation unit refers to a physically separable unit containing a single dose. Each unit contains a well-calculated predetermined amount of active ingredients, which can produce desired therapeutic effects. This preparation unit may be in the packaged form, for example tablets, capsules, powders in small tubes or bottles, or ointments, gels or creams in tubes or bottles.

Although the amount of active ingredient in the preparation unit can be varied, it is generally in a range of 1 mg-1000 mg based on the efficacy of the selected active ingredient.

When the compounds of the present invention represented by the formula (I) are used as antitumor agents, their dose may be varied depending on the needs of patients, conditions of the disease, the selected compounds and the like.

According to the present invention, the taxanes compounds are prepared by a method comprising the following steps:

Step 1 synthesis of taxanes mother nucleus part: by using 10-deacetyl baccatin III (10-DAB) as raw material, firstly, the hydroxyl groups at C7 and C10 positions of the mother nucleus part are selectively protected with substitutents, then the C13 hydroxy group is oxidized into keto-carbonyl group, followed by highly stereoselectively introducing a hydroxyl group with β configuration at C14 by using N-(sulfonyl) oxaziridine, to form 1,14-carbonate structure under the action of CDI, and finally C13 keto-carbonyl group is highly stereoselectively reduced into hydroxyl group with α configuration by CBS reduction method to give the taxanes mother nucleus part;

Step 2 synthesis of a precursor of five-member ring oxazolidine acid side chain: the precursor of five-member ring oxazolidine acid side chain is prepared by a series of reactions including introduction of protective groups, addition condensation, acid hydrolysis, aldol condensation, catalytic hydrogenation and the like;

Step 3 synthesis of taxanes derivatives: the precursor of five-member ring oxazolidine acid side chain is linked with the taxanes mother nucleus part by esterification, and a series of taxanes derivatives are generated after removal of the protective group by acid hydrolysis.

Preferably, the preparation method of the taxanes compounds of the present invention comprises the following steps:

Step 1 synthesis of taxanes mother nucleus part: by using 10-deacetyl baccatin III (10-DAB) as raw material, firstly, the hydroxyl groups at C7 and C10 positions of the mother nucleus part are selectively protected with substitutents, then the C13 hydroxy group is oxidized into keto-carbonyl group, followed by highly stereoselectively introducing a hydroxyl group with β configuration at C14 by using N-(sulfonyl) oxaziridine, to form 1,14-carbonate structure under the action of CDI, and finally C13 keto-carbonyl group is highly stereoselectively reduced into hydroxyl group with α configuration by CBS reduction method to give the taxanes mother nucleus part.

Step 2 synthesis of a precursor of five-member ring oxazolidine acid side chain: glycolic acid, used as raw material, is protected successively by benzyl group and t-butyloxycarbonyl group (Boc group) to generate the Boc-protected benzyl glycolate; different substituted aldehydes are condensed with ($S_R$)-t-butyl sulfinamide to form the corresponding enamine compounds; the Boc-protected benzyl glycolate and the enamine compound are reacted via an addition reaction in the presence of lithium salt, and then a chiral intermediate is given after acid hydrolysis, and the obtained intermediate is reacted with 1,1'-(dimethoxymethyl) p-methoxybenzene via an aldol condensation reaction, catalyzed by pyridinium p-toluenesulfonate (PPTS) to obtain a condensation compound. The amino group of the condensation compound is substituted with different substituents, and the precursor of five-member ring oxazolidine acid side chain is finally given after catalytic hydrogenation. The reaction route is as follows:

wherein, in Step 1, the hydroxyl groups at C7 and C10 positions are protected with substituents:

(1) When $R_3$ and $R_4$ are —$OR_6$, the reaction involved is: firstly, the hydroxyl group is reacted with p-toluenesulfonyl chloride (TsCl) at room temperature to 0° C. in tetrahydrofuran or dichloromethane as the solvent and pyridine (Py) as the alkali to give p-toluenesulfonate, which is further reacted with a Grignard reagent to give the corresponding ether —$OR_6$;

(2) When $R_3$ and $R_4$ are —$OCOOR_6$ or —$OCONR_{7a}R_{7b}$, the reaction involved is: under alkaline conditions, the hydroxyl

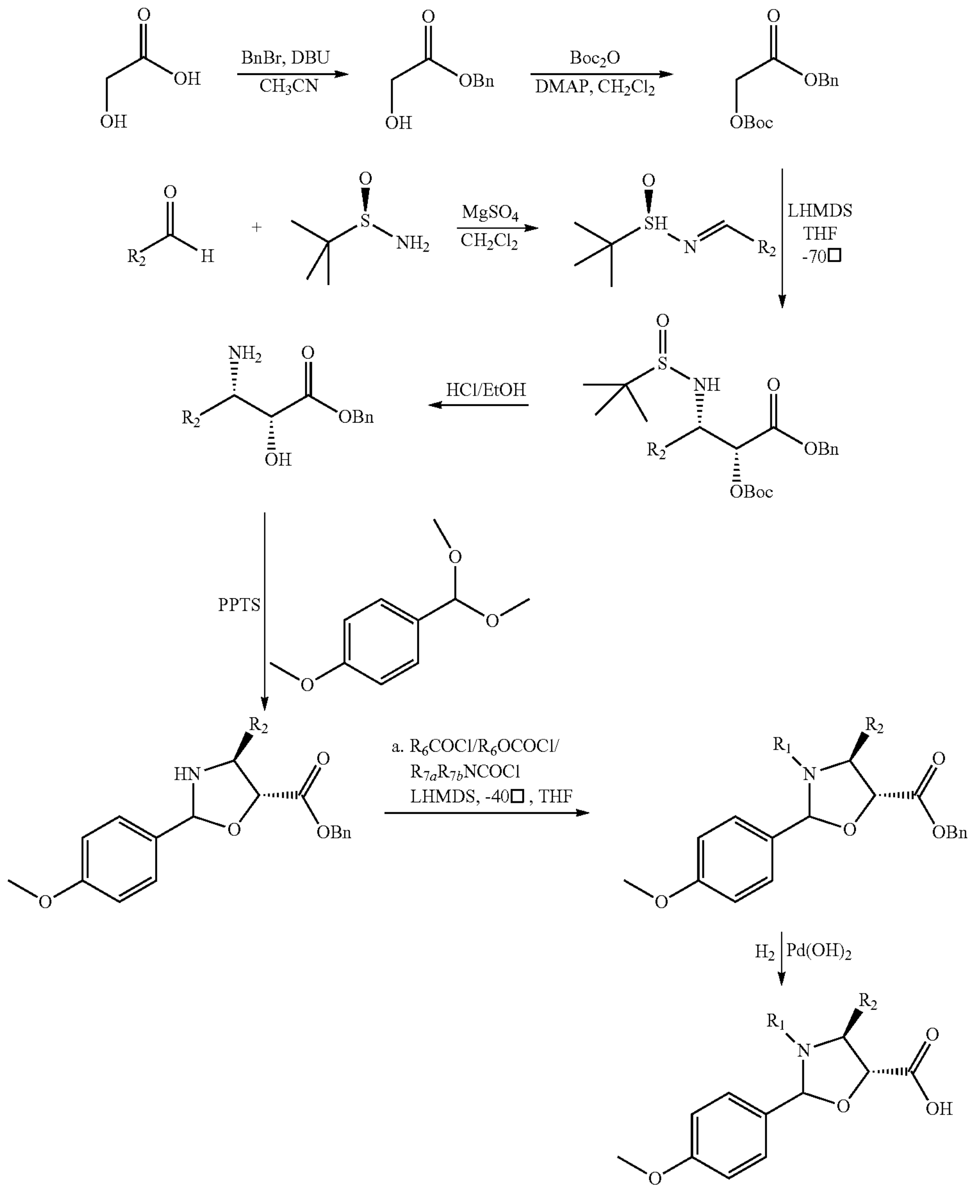

Step 3 synthesis of taxanes derivatives: the precursor of five-member ring oxazolidine acid side chain is linked with the taxanes mother nucleus part by esterification, and a series of taxanes derivatives are generated after removal of the protective group by acid hydrolysis.

group is reacted with the corresponding acyl chloride in tetrahydrofuran as the solvent at room temperature to −70° C.;

(3) When $R_3$ and $R_4$ are —$OCOSR_6$, the reaction involved is: the hydroxyl group is reacted with N,N'-carbonyldiimidazole (CDI) in tetrahydrofuran as the solvent at room temperature, and the obtained product is further reacted with mercaptan via substitution reaction.

In Step 1, the stereoselective reduction on the C13 keto-carbonyl group by CBS reduction method includes the following specific steps: C13-oxo is stereoselectively reduced into C13-α-OH by using anhydrous tetrahydrofuran, dry dichloromethane or alcohols as the solvent, (R)-2-methyl oxazaborodine as the catalyst and boranes as the reducing agent at room temperature to −70° C.

In Step 2, said different substituted aldehydes include C1-C6 hydrocarbyl aldehydes, C1-C6 substituted hydrocarbyl aldehydes, aromatic aldehydes, substituted aromatic aldehydes and heteroaromatic aldehydes and the like; The reaction involved in the substitution of the amino group on the chiral intermediates is carried out by using tetrahydrofuran, dichloromethane or dioxane as the solvent, to react with the corresponding acyl chlorides under alkaline conditions at room temperature to −70° C.; In the catalytic hydrogenation reaction, palladium-charcoal or palladium hydroxide is used as the catalyst, hydrogen is introduced at normal pressure or pressurized conditions, and the reaction is preferably carried out in alcohols, tetrahydrofuran or dichloromethane and the like as the solvent.

Preferably,

In Step 1, the hydroxyl groups C7 and C10 positions are protected by substitutents:

(1) When $R_3$ and $R_4$ are —$OR_6$, dichloromethane is preferably used as the solvent, the temperature is at 0° C. and the Grignard reagent includes $R_6MgBr$;

(2) When $R_3$ and $R_4$ are —$OCOOR_6$ or —$OCONR_{7a}R_{7b}$, lithium hexamethyldisilazide is preferably used as the alkali and the temperature is preferably at −40° C.; the acyl chloride includes $R_6OCOCl$ and $R_{7a}R_{7b}NCOCl$;

(3) When $R_3$ and $R_4$ are —$OCOSR_6$, the mercaptan includes $R_6SH$.

In Step 1, the stereoselective reduction on the C13 keto-carbonyl group by CBS reduction method is preferably carried out at room temperature by using anhydrous tetrahydrofuran as the solvent;

In Step 2, in the reaction involved in the substitution of the amino group on the intermediate, lithium hexamethyldisilazide (LHMDS) is preferably used as the alkali and tetrahydrofuran is used as the solvent; the temperature is preferably at −40° C., the acyl chloride includes $R_6COCl$, $R_6OCOCl$ and $R_{7a}R_{7b}NCOCl$; in the catalytic hydrogenation reaction, palladium hydroxide is preferably used as the catalyst, hydrogen is introduced at 20 psi and the reaction is preferably carried out in an alcoholic solution.

The taxanes compounds of the present invention have oral antitumor activity and the beneficial effects of the present invention are illustrated below by experimental data.

1. Cytotoxicity Assay Using Human Tumor Cell Lines

Paclitaxel was used as the positive drug. MTT assay was used to investigate the proliferation inhibition rate of taxanes derivatives containing 1,14-carbonate baccatin III of the present invention on 16 cancer cell lines (including MCF-7, MDA-MB-436 breast cancer cells; A549, NCI-H460 non-small cell lung cancer; A2780 ovarian cancer; A375, B16 melanoma; HCT 116, HT-29 colon cancer; Hela cervical cancer; HL-60, K562 leukemia; LNCaP, Du145 prostate cancer; LN-18, BGC-823 gastric cancer) at a concentration of 1 μM and the experimental results are shown in Table 1.

TABLE 1

Proliferation inhibition rate of the taxanes compounds of the present invention on 16 cancer cell lines

| | Proliferation inhibition rate at a concentration of 1 μM | | | | | | | |
|---|---|---|---|---|---|---|---|---|
| Compounds | A2780 Ovarian cancer | HeLa Uterin cancer | MCF-7 Breast cancer | NCI-H460 Non-small cell lung cancer | A375 Melanoma | HT29 Colon cancer | HL60 Leukemia | DU145 Prostate cancer |
| Paclitaxel | 96.68 | 101.04 | 94.20 | 87.48 | 96.22 | 88.36 | 96.80 | 90.62 |
| PCMI-01 | 96.72 | 100.54 | 96.00 | 87.94 | 90.80 | 89.41 | 96.57 | 87.76 |
| PCMI-02 | 94.69 | 98.20 | 93.54 | 82.25 | 89.84 | 88.98 | 95.90 | 84.71 |
| PCMI-03 | 95.13 | 99.36 | 95.27 | 85.31 | 88.56 | 88.47 | 95.69 | 84.96 |
| PCMI-04 | 94.65 | 98.28 | 100.73 | 81.84 | 82.17 | 88.28 | 95.81 | 83.87 |
| PCMI-05 | 94.59 | 99.45 | 84.86 | 81.98 | 87.90 | 87.93 | 97.17 | 83.88 |
| PCMI-06 | 96.00 | 99.89 | 86.26 | 84.68 | 94.40 | 87.33 | 97.66 | 89.14 |
| PCMI-07 | 95.02 | 100.10 | 87.12 | 82.65 | 92.54 | 86.58 | 97.46 | 86.78 |
| PCMI-08 | 92.50 | 97.27 | 81.28 | 85.19 | 92.85 | 81.67 | 96.85 | 86.73 |
| PCMI-09 | 95.63 | 101.39 | 89.77 | 85.82 | 96.93 | 87.84 | 98.52 | 90.26 |
| PCMI-10 | 94.98 | 99.86 | 85.90 | 81.01 | 94.18 | 86.21 | 97.49 | 87.98 |
| PCMI-11 | 94.58 | 99.59 | 82.38 | 82.16 | 92.37 | 85.91 | 97.89 | 87.16 |
| PCMI-12 | 94.33 | 100.43 | 81.75 | 82.32 | 91.97 | 85.44 | 97.19 | 86.65 |
| PCMI-13 | 95.86 | 100.48 | 84.68 | 86.23 | 93.14 | 87.38 | 97.53 | 90.66 |
| PCMI-14 | 94.23 | 99.88 | 88.45 | 86.94 | 95.31 | 87.26 | 97.45 | 89.78 |
| PCMI-15 | 95.73 | 101.19 | 95.53 | 86.03 | 97.86 | 88.67 | 97.83 | 90.76 |
| PCMI-16 | 96.12 | 101.60 | 97.22 | 87.23 | 96.29 | 89.19 | 97.81 | 91.41 |
| PCMI-17 | 96.60 | 100.94 | 93.12 | 89.16 | 94.89 | 88.49 | 97.34 | 90.68 |
| PCMI-18 | 95.69 | 98.75 | 96.23 | 88.59 | 95.06 | 85.23 | 97.85 | 89.68 |
| PCMI-19 | 94.24 | 99.56 | 89.65 | 87.35 | 95.16 | 87.23 | 96.89 | 89.97 |
| PCMI-20 | 95.51 | 100.57 | 85.40 | 86.79 | 93.38 | 87.25 | 96.92 | 88.62 |
| PCMI-21 | 96.40 | 99.54 | 88.69 | 85.51 | 96.65 | 87.65 | 96.52 | 90.58 |

TABLE 1-continued

Proliferation inhibition rate of the taxanes compounds of the present invention on 16 cancer cell lines

| Compound | Proliferation inhibition rate at a concentration of 1 μM MDA-MB-436 Breast cancer | LN-18 Gastric canser | BGC-823 Gastric cancer | A549 Non-small cell lung cancer | B16 Melanoma | HCT 116 Colon cancer | K562 Leukemia | LNCaP Prostate cancer |
|---|---|---|---|---|---|---|---|---|
| Paclitaxel | 83.09 | 94.49 | 92.52 | 81.59 | 84.05 | 70.36 | 96.62 | 87.10 |
| PCMI-01 | 81.46 | 92.82 | 93.10 | 66.90 | 78.06 | 59.69 | 92.85 | 80.67 |
| PCMI-02 | 82.62 | 96.58 | 94.22 | 79.59 | 84.07 | 66.36 | 94.67 | 83.65 |
| PCMI-03 | 80.12 | 95.35 | 92.32 | 68.57 | 78.23 | 58.31 | 93.56 | 82.64 |
| PCMI-04 | 79.43 | 91.80 | 89.83 | 66.26 | 73.24 | 55.04 | 91.52 | 79.19 |
| PCMI-05 | 74.46 | 93.26 | 90.89 | 67.81 | 71.49 | 58.72 | 91.36 | 81.59 |
| PCMI-06 | 77.82 | 94.58 | 93.63 | 75.52 | 80.65 | 67.08 | 93.35 | 83.63 |
| PCMI-07 | 80.47 | 96.12 | 94.14 | 74.89 | 78.60 | 68.85 | 94.01 | 84.87 |
| PCMI-08 | 65.68 | 87.69 | 80.81 | 68.13 | 70.64 | 58.70 | 90.79 | 84.32 |
| PCMI-09 | 81.34 | 94.98 | 94.88 | 75.80 | 81.71 | 65.46 | 92.60 | 86.16 |
| PCMI-10 | 77.27 | 93.66 | 91.21 | 70.51 | 71.43 | 65.57 | 90.63 | 85.87 |
| PCMI-11 | 78.96 | 92.88 | 90.64 | 72.34 | 72.56 | 64.32 | 92.13 | 86.45 |
| PCMI-12 | 81.41 | 93.44 | 93.01 | 73.59 | 75.91 | 66.56 | 91.22 | 86.32 |
| PCMI-13 | 81.03 | 93.83 | 94.04 | 77.11 | 81.23 | 68.45 | 94.25 | 86.33 |
| PCMI-14 | 80.24 | 93.45 | 95.78 | 76.18 | 80.33 | 65.45 | 92.69 | 85.32 |
| PCMI-15 | 81.99 | 95.71 | 94.98 | 74.60 | 80.75 | 68.33 | 93.24 | 86.66 |
| PCMI-16 | 81.23 | 95.24 | 95.28 | 74.65 | 83.06 | 67.09 | 94.95 | 86.77 |
| PCMI-17 | 85.08 | 95.94 | 95.12 | 80.34 | 82.31 | 69.56 | 96.53 | 86.69 |
| PCMI-18 | 82.34 | 94.65 | 94.32 | 78.68 | 81.25 | 68.32 | 94.52 | 84.56 |
| PCMI-19 | 83.58 | 93.87 | 93.27 | 80.24 | 83.65 | 67.28 | 92.68 | 87.25 |
| PCMI-20 | 81.08 | 94.30 | 94.95 | 80.39 | 81.60 | 68.59 | 93.78 | 85.96 |
| PCMI-21 | 83.09 | 94.74 | 93.26 | 74.88 | 75.81 | 70.09 | 94.95 | 87.38 |

Preliminary activity evaluation indicates that such taxanes derivatives show similar or stronger cytotoxicity on most cancer cell lines than that of the positive control drug. Only in both cancer cell lines of A549 and B16, the cytotoxicity of the taxanes derivatives is slightly lower than that of the positive control drug. Experimental results show that such taxanes derivatives of the present invention have excellent tumor inhibiting activity.

From the activity evaluation data of the above-mentioned preliminary screen, it can be seen that the series of taxanes derivatives synthesized in the present invention have activity. Afterward, the compounds are investigated to examine their $IC_{50}$ values on breast cancer cell line MCF-7. Paclitaxel was used as the positive control drug. Experiments for each compound were independently repeated for three times and multiple holes were used in each experiment. The exposure time of drugs was 72 hours. The median lethal dose ($IC_{50}$) is expressed as mean±SD and the experimental data are shown in Table 2.

TABLE 2

$IC_{50}$ values of the taxanes compounds of the present invention on breast cancer cell line MCF-7

| Compounds | MCF-7 ($IC_{50}$, nM) |
|---|---|
| Paclitaxel | 7.05 ± 0.12 |
| PCMI-01 | 2.10 ± 0.08 |
| PCMI-02 | 6.93 ± 0.12 |
| PCMI-03 | 2.89 ± 0.10 |
| PCMI-04 | 3.40 ± 0.14 |
| PCMI-05 | 4.04 ± 0.18 |
| PCMI-06 | 16.24 ± 0.08 |
| PCMI-07 | 4.49 ± 0.02 |
| PCMI-08 | 7.93 ± 0.14 |
| PCMI-09 | 14.31 ± 0.12 |
| PCMI-10 | 6.44 ± 0.18 |
| PCMI-11 | 4.25 ± 0.06 |
| PCMI-12 | 3.24 ± 0.04 |

TABLE 2-continued $IC_{50}$ values of the taxanes compounds of the present invention on breast cancer cell line MCF-7

| Compounds | MCF-7 ($IC_{50}$, nM) |
|---|---|
| PCMI-13 | 3.89 ± 0.12 |
| PCMI-14 | 15.40 ± 0.16 |
| PCMI-15 | 18.21 ± 0.24 |
| PCMI-16 | 21.17 ± 0.21 |
| PCMI-17 | 3.84 ± 0.08 |
| PCMI-18 | 4.12 ± 0.16 |
| PCMI-19 | 6.58 ± 0.02 |
| PCMI-20 | 2.94 ± 0.04 |
| PCMI-21 | 3.46 ± 0.16 |

As shown from the data of Table 2, the $IC_{50}$ value of the positive control drug paclitaxel is 7.05 nM. The $IC_{50}$ values of taxanes derivatives containing the structure of 1,14-carbonate baccatin III of the present invention thereof are quite equal to that of paclitaxel, maintaining at the same order of magnitude. While $IC_{50}$ values of some derivatives are better than that of paclitaxel. Thus, it can be seen that in vitro activity of the derivatives of the present invention remain unchanged or even be improved as compared with paclitaxel.

2. Caco-2 Cell Monolayer Membrane Transport Assay

Human-derived colorectal adenocarcinoma cell line Caco-2 cell monolayer model was used to study the bidirectional transport of the target compounds from the apical (AP) side to the basolateral (BL) side and from BL side to AP side. HPLC was used for quantitative analysis to calculate transport parameters, apparent permeability coefficient (Papp) and the efflux ratio. Paclitaxel was used as the positive control drug and the P-gp substrates erythromycin was used as a reference to predict the oral bioavailability in vivo of these taxanes derivatives and affinity thereof with P-gp.

TABLE 3

A-to-B Papp of the taxanes derivatives of the present invention in Caco-2 cell model

| Compounds | | Papp × $10^{-6}$ cm/sec Sample-01 | Sample-02 | Mean | SD |
|---|---|---|---|---|---|
| Erythromycin | A-B | 0.80 | 0.63 | 0.71 | 0.16 |
| | B-A | 7.15 | 7.04 | 7.09 | 0.01 |
| Metoprolol | A-B | 28.09 | 26.25 | 27.17 | 0.05 |
| | B-A | 22.44 | 22.96 | 22.70 | 0.02 |
| Atenolol | A-B | 1.07 | 0.67 | 0.87 | 0.32 |
| | B-A | 0.50 | 0.55 | 0.53 | 0.06 |
| Paclitaxel | A-B | 1.02 | 0.93 | 0.97 | 0.07 |
| PCMI-01 | A-B | 4.47 | 3.87 | 4.17 | 0.10 |
| PCMI-02 | A-B | 1.50 | 1.47 | 1.48 | 0.02 |
| PCMI-03 | A-B | 3.45 | 3.89 | 3.67 | 0.31 |
| PCMI-04 | A-B | 4.46 | 2.86 | 3.66 | 0.31 |
| PCMI-05 | A-B | 2.59 | 2.56 | 2.57 | 0.01 |
| PCMI-06 | A-B | 1.31 | 1.13 | 1.22 | 0.11 |
| PCMI-07 | A-B | 3.24 | 2.05 | 2.64 | 0.32 |
| PCMI-08 | A-B | 19.53 | 17.33 | 18.43 | 0.08 |
| PCMI-09 | A-B | 5.78 | 3.59 | 4.68 | 0.33 |
| PCMI-10 | A-B | 1.25 | 0.89 | 1.07 | 0.24 |
| PCMI-11 | A-B | 1.24 | 1.02 | 1.13 | 0.16 |
| PCMI-12 | A-B | <1.36* | <1.43* | <1.43 | N/A |
| PCMI-13 | A-B | <1.30* | <1.67* | <1.67 | N/A |
| PCMI-14 | A-B | 3.21 | 2.87 | 3.04 | 0.24 |
| PCMI-15 | A-B | 2.14 | 2.78 | 2.46 | 0.18 |
| PCMI-16 | A-B | 1.41 | 1.87 | 1.64 | 0.20 |
| PCMI-17 | A-B | 4.70 | 3.16 | 3.93 | 0.28 |
| PCMI-18 | A-B | 2.65 | 2.33 | 2.49 | 0.23 |
| PCMI-19 | A-B | 3.78 | 4.05 | 3.92 | 0.19 |
| PCMI-20 | A-B | 1.08 | 0.75 | 0.92 | 0.25 |
| PCMI-21 | A-B | 2.32 | 2.58 | 2.45 | 0.08 |

*The measured value was lower than the minimum limit;
N/A: Undetectable by known methods

TABLE 4

Trans-membrane recovery rate in mass of the taxanes derivatives of the present invention in Caco-2 cell model

| Compounds | | Recovery rate in mass (%) Sample-01 | Sample-02 | Mean | SD |
|---|---|---|---|---|---|
| Erythromycin | A-B | 99.58 | 98.51 | 99.04 | 0.01 |
| Metoprolol | A-B | 102.51 | 95.49 | 99.00 | 0.05 |
| Atenolol | A-B | 93.89 | 96.29 | 95.09 | 0.02 |
| Paclitaxel | A-B | 94.61 | 107.07 | 100.84 | 0.09 |
| PCMI-01 | A-B | 48.17 | 61.18 | 54.67 | 0.17 |
| PCMI-02 | A-B | 44.14 | 57.37 | 50.75 | 0.18 |
| PCMI-03 | A-B | 65.12 | 58.23 | 61.68 | 0.08 |
| PCMI-04 | A-B | 85.19 | 66.54 | 75.87 | 0.17 |
| PCMI-05 | A-B | 58.11 | 51.29 | 54.70 | 0.09 |
| PCMI-06 | A-B | 128.21 | 96.59 | 112.40 | 0.20 |
| PCMI-07 | A-B | 54.25 | 46.29 | 50.27 | 0.11 |
| PCMI-08 | A-B | 101.83 | 97.05 | 99.44 | 0.03 |
| PCMI-09 | A-B | 70.43 | 82.62 | 76.53 | 0.11 |
| PCMI-10 | A-B | 33.99 | 40.55 | 37.27 | 0.12 |
| PCMI-11 | A-B | 79.65 | 80.23 | 79.94 | 0.01 |
| PCMI-12 | A-B | 27.8-29.1* | 38.2-39.5* | 27.8-39.5 | N/A |
| PCMI-13 | A-B | 40.8-42.0* | 41.5-43.1* | 40.8-43.1 | N/A |
| PCMI-14 | A-B | 95.04 | 87.58 | 91.31 | 0.06 |
| PCMI-15 | A-B | 83.68 | 74.85 | 79.27 | 0.08 |
| PCMI-16 | A-B | 32.69 | 33.52 | 33.10 | 0.02 |
| PCMI-17 | A-B | 103.50 | 73.90 | 88.70 | 0.24 |
| PCMI-18 | A-B | 85.64 | 90.87 | 88.26 | 0.04 |
| PCMI-19 | A-B | 78.23 | 70.69 | 74.46 | 0.07 |
| PCMI-20 | A-B | 89.75 | 83.30 | 86.52 | 0.05 |
| PCMI-21 | A-B | 76.56 | 67.49 | 72.03 | 0.09 |

*The measured value was lower than the minimum limit;
N/A: Undetectable by known methods

TABLE 5

Efflux ratio of the representative taxanes derivatives of the present invention in Caco-2 cell model

| Compounds | Caco-2 cell line (21 days) Papp ($10^{-6}$ cm/s) A-B | SD | B-A | SD | Efflux ratio [a] |
|---|---|---|---|---|---|
| Erythromycin | 0.58 | 0.08 | 9.89 | 0.04 | 16.92 |
| Paclitaxel | 0.97 | 0.07 | 33.39 | 0.01 | 34.38 |
| PCMI-08 | 16.40 | 0.04 | 33.48 | 0.07 | 2.04 |
| PCMI-09 | 3.56 | 0.05 | 28.97 | 0.08 | 8.14 |
| PCMI-01 | 2.83 | 0.19 | 18.20 | 0.18 | 6.42 |
| PCMI-17 | 2.40 | 0.21 | 5.74 | 0.24 | 2.39 |
| PCMI-19 | 2.79 | 0.12 | 21.34 | 0.08 | 7.65 |
| PCMI-03 | 2.97 | 0.07 | 28.56 | 0.04 | 9.62 |
| PCMI-04 | 3.21 | 0.14 | 26.45 | 0.07 | 8.24 |
| PCMI-14 | 1.98 | 0.06 | 18.96 | 0.15 | 9.58 |
| PCMI-07 | 2.64 | 0.32 | 25.26 | 0.20 | 9.56 |
| PCMI-20 | 0.92 | 0.25 | 7.16 | 0.10 | 7.81 |

[a] efflux ratio = Papp B-A/Papp A-B

The experimental results are shown in Table 3. It can be seen that the A-to-B Papp values of the most of taxanes derivatives of the present invention are higher than that of paclitaxel (Papp A-to-B=0.97), particularly for PCMI-08, the Papp A-to-B value thereof>10×$10^{-6}$ cm/s, which belongs to highly permeable substrate. These data indicate that these taxanes derivatives containing the structure of 1,14-carbonate baccatin III have good trans-membrane capacity, thus they are predicted to be better absorbed in vivo than paclitaxel.

The trans-membrane recovery rates of these taxanes derivatives are shown in Table 4. Bidirectional transports of 10 compounds selected from the 21 taxanes derivatives are evaluated and the results are shown in Table 5. It can be seen from the efflux ratios that, as compared with paclitaxel, efflux ratios of these derivatives of the present invention are reduced at different levels. Accordingly, the oral absorption in vivo is predicted to be improved.

3. In Vivo Oral Bioavailability Assay

Materials

The compound PCMI-08 was synthesized and detected according to the methods provided in the present invention. The internal standard, paclitaxel, was purchased from China's National Institute for the Control of Pharmaceutical and Biological Products (NICPBP). Chromatography-grade acetonitrile was purchased from Sigma-Aldrich Inc. Tween 80 and ethyl acetate were purchased from Aladdin reagent Inc. Male S.D. rats were purchased from Beijing Weitonglihua Inc. and raised in animal house for two weeks.

Apparatus

Agilent 1100 series HPLC, Agilent G1313A Autosampler, Thermo Finnigan TSQ quadrupole mass spectrometer (San Jose, Calif., USA), Xcalibur® (version 1.3) software (Thermo Finnigan) data analysis software.

Experimental Procedure:

200 mg of PCMI-08 was dissolved in 4 ml of a mixed solution of Tween 80 and anhydrous ethanol (1:1) to prepare a stock solution at 50 mg/ml and normal saline was added to adjust to a suitable concentration. 12 male S.D. rats (300 g of body weight) were taken and divided into two groups after overnight fasting. One group was treated with intravenous injection (5 mg/kg) and the other group was treated orally (60 mg/kg). Blood was sampled in the intravenous group at $0^{th}$ min, $5^{th}$ min, $10^{th}$ min, $20^{th}$ min, $40^{th}$ min, $1^{st}$ h, $2^{nd}$ h, $4^{th}$ h, $6^{th}$ h, $8^{th}$ h, $12^{th}$ h, $24^{th}$ h, while the oral group at $5^{th}$ min, $15^{th}$ min, $30^{th}$ min, $45^{th}$ min, $1^{st}$ h, $2^{nd}$ h, $4^{th}$ h, $6^{th}$ h, 8th h, 12th h, 24th h. After 10 min centrifugation of plasma at 4500 rpm, the upper serum was taken and transferred to the corresponding EP tube, placed in a −40° C. freezer for assay.

Construction of Standard Curve of PCMI-08

Agilent 1100 series configuration: Agilent G1313A HPLC autosampler device, 150 mm×2.1 mm C18 Thermo column (particle size 3 μm) reversed-phase column, detection wavelength at 230 nm, column temperature at 30° C., mobile phase of acetonitrile/water (7:3), a flow rate at 0.2 ml/min, injection volume of 20 μl. The mass spectrometry (MS) combined was Thermo Finnigan TSQ Quantum triple quadrupole configurated with electrospray ionization (ESI) in the positive ion mode. The parameters of MS analysis were as follows: spray chamber voltage, 4.0 kv; heated capillary temperature, 350° C.; protective gas (nitrogen); 20 psi; auxiliary gas (nitrogen): 5 psi; collision gas (argon); pressure: 1.5 mmTorr.; Collision energy: CA 17 eV; FA and IFA were 19 eV; IS was 15 eV.

Paclitaxel was selected as an internal standard with a retention time of 3.07 min. Retention time of PCMI-08 was 5.13 min. MS detection condition to PCMI-08 was set as follows: 957→901 m/z; paclitaxel as an internal standard. Detection conditions: 876→308 m/z. The concentration range of the standard curve of PCMI-08 was 5-10,000 ng/ml ($\gamma^2$>0.99) and the minimum detection limit was 5 ng/ml.

Extraction and Analysis of Plasma Samples

100 μL of plasma samples were taken, into which 100 μL of the internal standard (paclitaxel, 500 ng/ml acetonitrile solution) was added, followed by addition of 3 ml of ethyl acetate after well homogenized via vortex, after 5 min shaking, centrifuging for 8 min at a rotating speed of 4500 rpm. The supernatant was transferred to a clean EP tube with nitrogen to blow to dry under heating condition. After reconstitution with 120 μL mobile phase ($CH_3CN/H_2O$=7:3), the solution was centrifuged at 12,000 rpm for 3 min, 100 μl of supernatant was taken and transferred to an autosampler vial. After LC-MS/MS detection, statistical data and pharmacokinetic parameters were processed by Xcalibur® (version 1.3) software (Thermo Finnigan).

Results

Drug concentration-time curve of the compound PCMI-08 by oral or intravenous administration is shown in FIG. 1. Related pharmacokinetic parameters of PCMI-08 are shown in the following Table. The half-life of PCMI-08 is relatively long, generally 10 h, and the mean retention time thereof is also extended relatively up to 10 h or longer. The absolute oral bioavailability (F %) is up to 65.8%. As compared with the reported absolute oral bioavailability of paclitaxel of less than 6%, the oral bioavailability of PCMI-08 in animals has been improved to a significant extent.

TABLE 6

Relevant pharmacokinetic parameters of PCMI-08 by intravenous and oral administration

| | | PCMI-08 | |
|---|---|---|---|
| Parameters | Unit | Intravenous administration (5 mg/kg) | Oral administration (60 mg/kg) |
| $t_{1/2}$ | h | 10.21 ± 1.72 | 10.44 ± 1.14 |
| $C_{max}$ | ng/ml | 11017.79 ± 2679.59 | 2121.12 ± 454.09 |
| $t_{max}$ | h | 0 | 3.0 ± 1.1 |
| $AUC_{0-t}$ | ng · h/ml | 3439.76 ± 1479.88 | 25306.31 ± 6148.79 |
| $AUC_{0-\infty}$ | ng · h/ml | 4054.33 ± 1860.39 | 32010.17 ± 8537.60 |

TABLE 6-continued

Relevant pharmacokinetic parameters of PCMI-08 by intravenous and oral administration

| | | PCMI-08 | |
|---|---|---|---|
| Parameters | Unit | Intravenous administration (5 mg/kg) | Oral administration (60 mg/kg) |
| $MRT_{0-\infty}$ | h | 10.08 ± 2.60 | 15.19 ± 1.71 |
| F | (%) | | 65.79 |

$AUC_{0-t}$: 0-24 hours area under the curve;
$AUC_{0-\infty}$: area under the curve;
$C_{max}$: peak concentration;
$t_{max}$: peak time;
MRT: mean residence time;
$t_{1/2}$: half-life time;
F: Absolute oral bioavailability,
$F = (AUC_{p.o} \times dose_{i.v})/(AUC_{i.v} \times dose_{p.o}) \times 100\%$

EXAMPLES

The following examples are provided to further illustrate the present invention and not intended to limit the present invention in any way.

Example 1 Preparation of PCMI-01

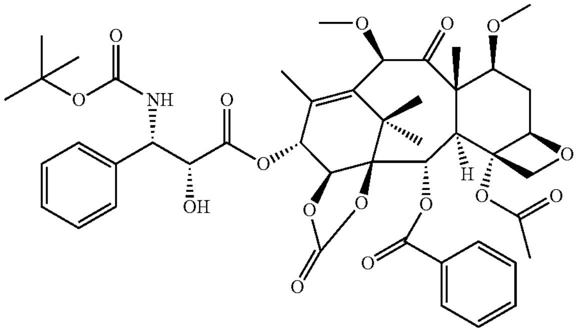

1) Preparation of (4S,5R)-3-t-butyloxycarbonyl-2-(4-methoxyphenyl)-4-phenyl-5-oxazolidine carboxylic acid

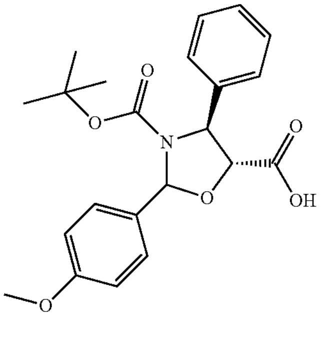 [SMILES: COc1ccc(C2O[C@@H](C(=O)O)[C@H](c3ccccc3)N2C(=O)OC(C)(C)C)cc1]

a. Preparation of benzyl glycolate

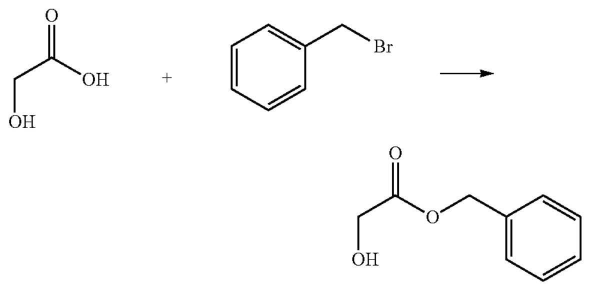

Glycolic acid (7.60 g, 0.10 mol) was dissolved in 10 ml of acetonitrile, into which benzyl bromide (13.60 g, 0.08 mol) was added and uniformly stirred. DBU (12.16 g, 0.08 mol) was slowly added dropwise into the reaction liquid at 0° C. After that, the reaction liquid was stirred overnight at room temperature. The reaction liquid was poured into ice water, extracted with ethyl acetate, the combined resultant organic phase was washed with 1M hydrochloric acid solution and saturated salt water successively, dried with anhydrous sodium sulfate and concentrated by rotary evaporation to give the compound as a yellow oil (12.50 g, 94%).

b. Preparation of Boc-protected benzyl glycolate

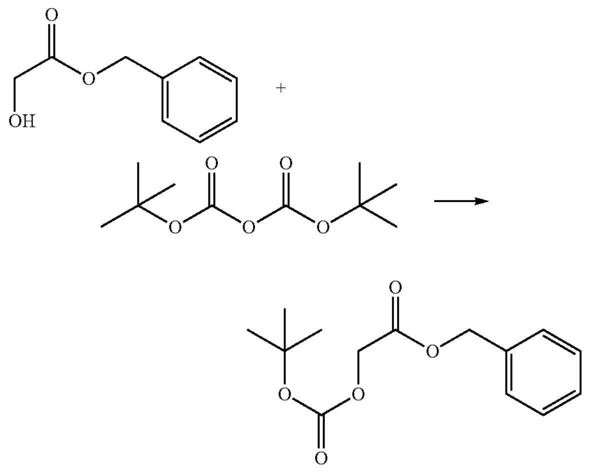

Benzyl glycolate (30 g, 0.25 mol) and Boc anhydride (39.1 g, 0.19 mol) were dissolved in 30 ml of dichloromethane. 5 ml of DMAP (4.62 g, 0.038 mol) in dichloromethane solution was added dropwise into the resultant reaction liquid at 80° C. After that, the reaction liquid was reacted at 15° C. for 0.5 h. After completion of the reaction, the reaction liquid was poured into ice water, extracted with ethyl acetate, the combined resultant organic phase was washed with water and saturated salt water successively. The organic phase was concentrated and recrystallized with petroleum ether/ethyl acetate in a ratio of 10:1 to give a white solid (32.5 g, 66%).

c. Preparation of N-t-butyl sulfinyl benzylenamine

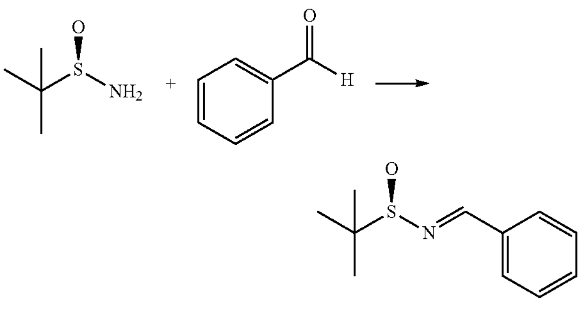

($S_R$)-t-butyl sulfinamide (5.22 g, 0.043 mol) and benzaldehyde (5.51 g, 0.052 mol) were dissolved in 20 ml of dichloromethane and the solution was added with magnesium sulfate (25.90 g, 0.22 mol) and PPTS (0.54 g, 2.20 mmol). The reaction liquid was stirred at room temperature for 24 h, filtered and the obtained filter cake was rinsed with dichloromethane for 3 times (20 ml×3) to give the crude product after concentration. The crude product was purified by column chromatography (petroleum ether/ethyl acetate=15:1) to give a colorless oil (7.71 g, 85.8%).

d. Preparation of benzyl 2R-t-butyloxycarbonyl-3S-t-butyl sulfinamide-phenyl propionate

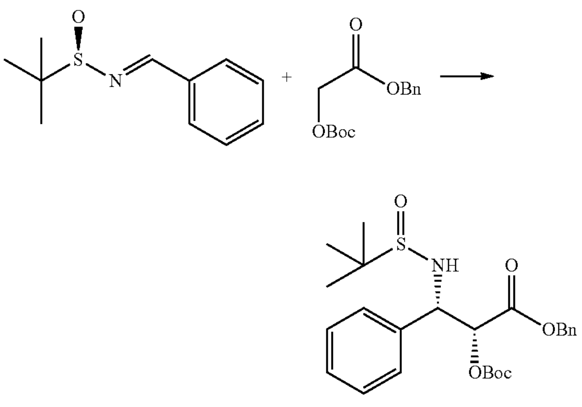

Boc-protected benzyl glycolate (32.5 g, 0.12 mol) was dissolved in 15 ml of tetrahydrofuran and LHMDS (120 ml, 0.12 mol) was slowly added dropwise into the reaction liquid at −70° C. After that, the reaction liquid was stirred for 0.5 h, followed by slowly adding N-t-butyl sulfinyl benzylenamine in THF solution (5.02 g, a solution of 0.024 mol in 8 ml of THF) dropwise and 4 hours later, the reaction was finished. The reaction liquid was poured into 50 ml of saturated ammonium chloride solution and extracted with ethyl acetate for 3 times (30 ml×3). The combined organic phases were dried, concentrated by rotary evaporation and purified by column chromatography (petroleum ether/ethyl acetate=10:1) to obtain a white solid (5.25 g, 46%).

e. Preparation of benzyl 2R-hydroxy-3S-aminophenyl propionate

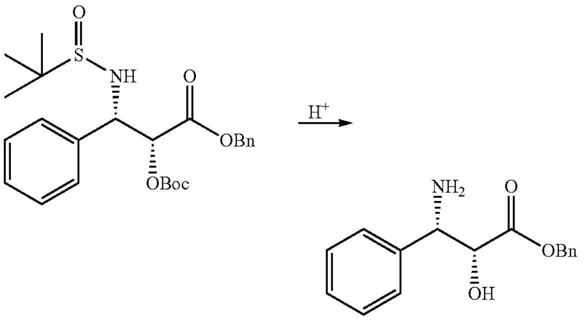

The product obtained in the previous step (5.25 g, 0.011 mol) was dissolved in 20 ml of 2N HCl/EtOAc solution and reacted at room temperature for 10 hours. After the completion of the reaction, the reaction liquid was concentrated and the obtained concentrate was extracted with dichloromethane/water (50 ml/100 ml). The aqueous phase was collected, extracted with dichloromethane and the pH value thereof was adjusted with 28% aqueous ammonia to 9-10. Finally, the aqueous phase was extracted with dichloromethane for 3 times (20 ml×3). The combined organic phase was dried, filtered and concentrated to give a white solid (2.85 g, 95.7%).

f. Preparation of benzyl (4S,5R)-2-(4-methoxyphenyl)-4-phenyl-5-oxazolidine carboxylate

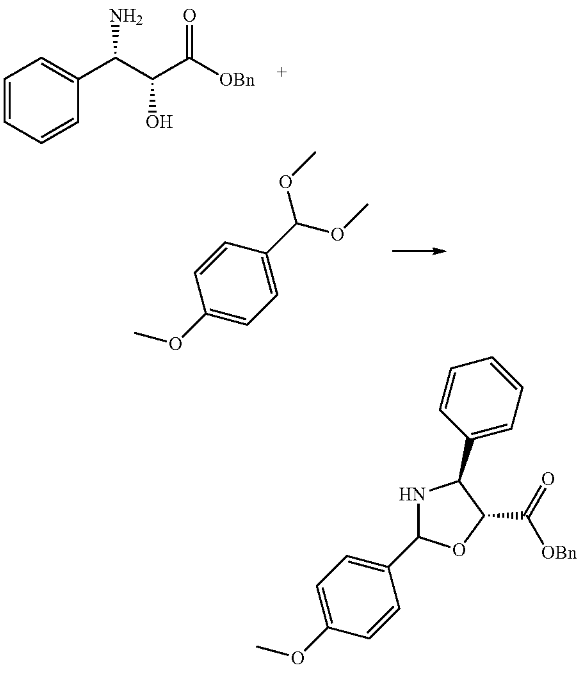

Benzyl 2R-hydroxy-3S-amino-phenyl propionate (2.66 g, 9.84 mmol) and the catalyst PPTS (0.24 g, 0.93 mmol) were dissolved in 10 ml of toluene and 1,1-dimethoxymethyl-4-methoxybenzene (2.15 g, 11.79 mmol) was slowly added dropwise into the reaction liquid at 100° C. After that, the reaction was maintained at a temperature of 90-100° C. for 2 hours, which was continued to be supplemented with 2.4 g of 1-dimethoxymethyl-4-methoxybenzene and then reacted for about 2 hours before finishing the reaction. The obtained reaction liquid was concentrated, separated and purified by column chromatography (petroleum ether/ethyl acetate=10:1), yielding a yellow oil (3.52 g, 92%). The yellow oil contained a small amount of p-methoxybenzaldehyde.

g. Preparation of benzyl (4S,5R)-3-t-butoxycarbonyl-2-(4-methoxyphenyl)-4-phenyl-5-oxazolidine carboxylate

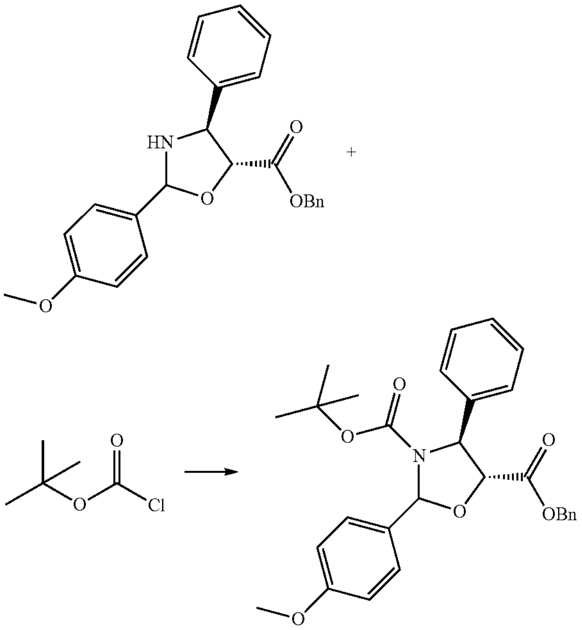

The oil obtained in the previous step (4.07 g, 10.47 mmol), t-butyloxy formyl chloride (1.56 g, 12.57 mmol) and triethylamine (2.64 g, 26.17 mol) were dissolved in 10 ml of dichloromethane and stirred overnight at room temperature. The reaction liquid was concentrated, separated and purified by column chromatography (petroleum ether/ethyl acetate=10:1) to give a yellow oil (4.83 g, 94.4%).

h. Preparation of (4S,5R)-3-t-butoxycarbonyl-2-(4-methoxyphenyl)-4-phenyl-5-oxazolidine carboxylic acid

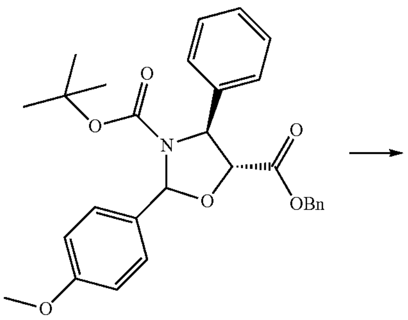

-continued

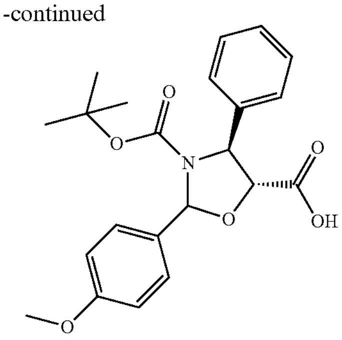

The product obtained in the previous step (4.83 g, 9.88 mmol) was dissolved in 10 ml of methanol, into which 1.0 g of palladium hydroxide was added. Hydrogen was introduced (20 psi) at room temperature and reacted for about 1 h, the completion of the reaction was monitored by TLC. The reaction liquid was filtered, concentrated, separated and purified by column chromatography (petroleum ether/ethyl acetate=5:1), to give the final product as a white solid (2.68 g, 67.9%).

2) Preparation of 7,10-dimethoxyl-1,14-carbonate baccatin III

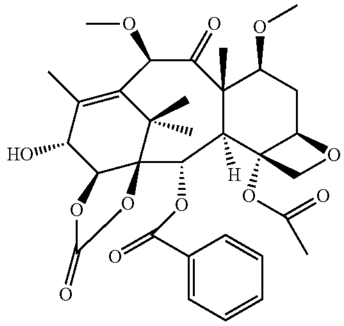

10-DAB (1 eq.) was used as raw material, dissolved in dichloromethane which was used as the solvent and added with 3 equivalents of pyridine at 0° C. Then the obtained reaction liquid was added dropwise with 3 equivalents of p-toluenesulfonyl chloride to react for 4 hours. By post-treatment of purification by column chromatography, the compound 1 was given in a yield of 85-90%.

The compound 1 (1 eq.) was dissolved in anhydrous tetrahydrofuran to react with methyl magnesium bromide (2.5 eq.) for 3 hours at room temperature under the protection of nitrogen. After post-treatment, the crude compound 2 was obtained after dried.

The compound 2 (1 eq.) was dissolved in acetone solution, into which 10 equivalents of manganese dioxide was added at room temperature to react for 4 hours. By post-treatment of purification by column chromatography, the compound 3 was given in a yield of 85%.

The compound 3 (1 eq.) was dissolved in dry THF/DMPU (4:1) solution, into which 1.2 equivalents of potassium t-butoxide was added at −70° C. to react for 20 min. The obtained reaction liquid was slowly added dropwise with 2 equivalents of N-(sulfonyl) oxaziridine to react for 2 hours. By post-treatment of purification by column chromatography, the compound 4 was given in a yield of 75%.

The compound 4 (1 eq.) was reacted with 2 equivalents of N,N'-carbonyldiimidazole (CDI) in dry tetrahydrofuran, to give the compound 5 in a yield of 95%.

The compound 5 (1 eq.) was dissolved in dry tetrahydrofuran, into which 0.2 equivalents of (R)-2-methyl oxazaborodine was added as the catalyst, followed by adding 5 equivalents of borane/THF solution to react for 8 hours at room temperature. After completion of reaction, by post-treatment of purification by column chromatography, the compound 6 of 7,10-dimethoxyl-1,14-carbonate baccatin III was obtained as the final product in a yield of 86%.

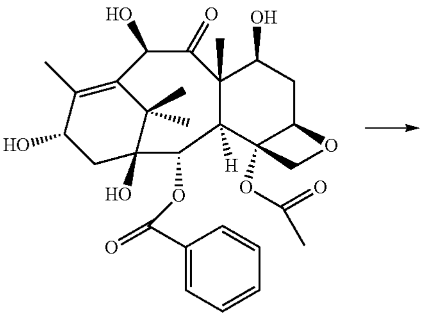

10-DAB

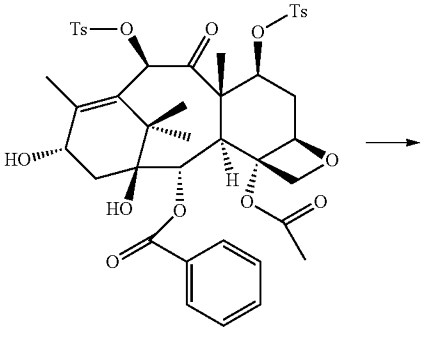

1

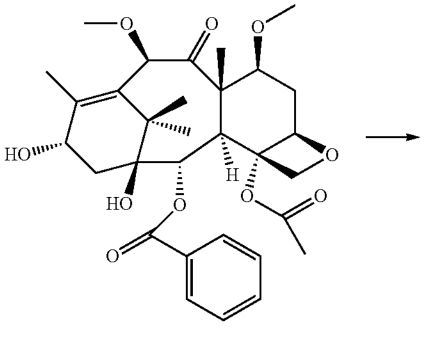

2

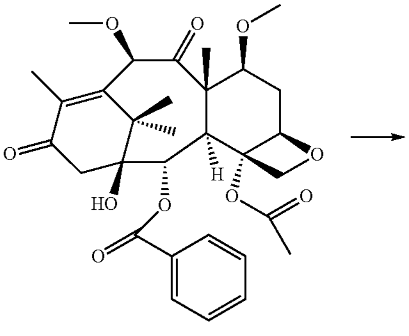

3

-continued

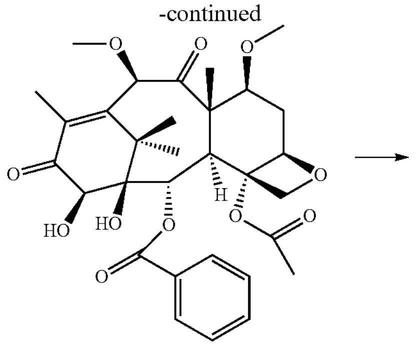

4

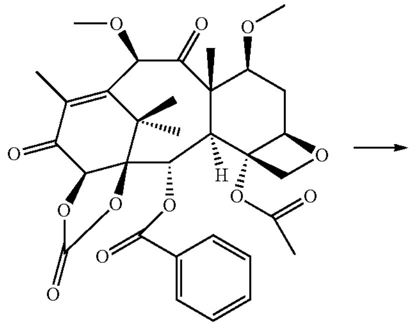

5

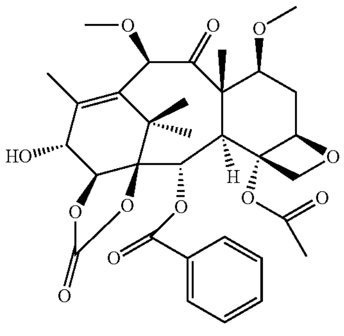

6

3) Preparation of PCMI-01

7,10-Dimethoxyl-1,14-carbonate baccatin III (1 eq.) and (4S,5R)-3-t-butoxycarbonyl-2-(4-methoxyphenyl)-4-phenyl-5-oxazolidine carboxylic acid (4 eq.) were dissolved in dichloromethane which was used as the solvent, into which 0.5 equivalents of DMAP and 2.0 equivalents of DCC were added successively to react overnight at room temperature. The obtained product was reacted in 2 equivalents of acetyl chloride/methanol solution to give the taxane derivative PCMI-01 as the final product. The overall yield of two steps was 71% and the purity of the final product was 95% or higher.

PCMI-01: mp: 242-243° C.;

MS (m/z) ESI: 900.4 $(M+Na)^+$;

$^1$H NMR (400 MHz, $CDCl_3$) δ 8.03 (d, J=7.3 Hz, 2H), 7.63 (t, J=7.4 Hz, 1H), 7.50 (t, J=7.7 Hz, 2H), 7.47-7.33 (m, 5H), 6.47 (d, J=5.7 Hz, 1H), 6.09 (d, J=7.5 Hz, 1H), 5.50 (d, J=9.0 Hz, 1H), 5.34 (s, 1H), 4.96 (d, J=8.0 Hz, 1H), 4.78 (d, J=6.8 Hz, 1H), 4.74 (s, 1H), 4.72 (s, 1H), 4.30 (d, J=8.5 Hz, 1H), 4.25 (d, J=8.5 Hz, 1H), 3.86 (dd, J=10.8, 6.3 Hz, 1H), 3.71 (d, J=7.5 Hz, 1H), 3.49 (s, 3H), 3.32 (s, 3H), 2.75-2.67 (m, 1H), 2.45 (s, 3H), 1.93 (s, 3H), 1.87-1.78 (m, 1H), 1.77 (s, 3H), 1.41 (s, 9H), 1.33 (s, 3H), 1.31 (s, 3H).

$^{13}$C NMR (101 MHz, $CDCl_3$) δ 203.51, 171.19, 164.63, 151.96, 135.97, 134.09, 129.92, 128.95, 128.12, 126.67, 88.08, 83.97, 82.17, 81.17, 80.51, 79.69, 75.99, 74.94, 74.42, 69.18, 57.88, 57.08, 46.76, 41.90, 31.83, 29.69, 28.25, 26.06, 22.61, 22.14, 14.56, 10.39.

Example 2 Preparation of PCMI-02

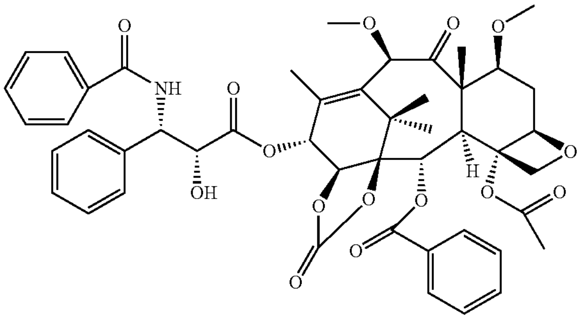

1) Preparation of (4S,5R)-3-benzoyl-2-(4-methoxyphenyl)-4-phenyl-5-oxazolidine carboxylic acid

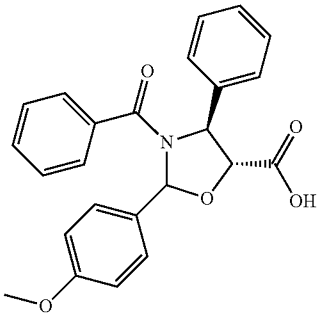 [SMILES: COc1ccc(C2O[C@@H](C(=O)O)[C@H](c3ccccc3)N2C(=O)c2ccccc2)cc1]

(4S,5R)-3-benzoyl-2-(4-methoxyphenyl)-4-phenyl-5-oxazolidine carboxylic acid was prepared with the substantially same method as shown in Example 1, except for Step g. Other steps could be seen in the reactions of Example 1.

g. Preparation of benzyl (4S,5R)-3-benzoyl-2-(4-methoxyphenyl)-4-phenyl-5-oxazolidine carboxylate

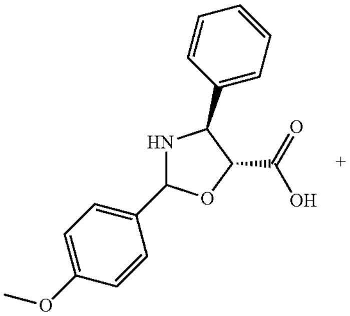

-continued

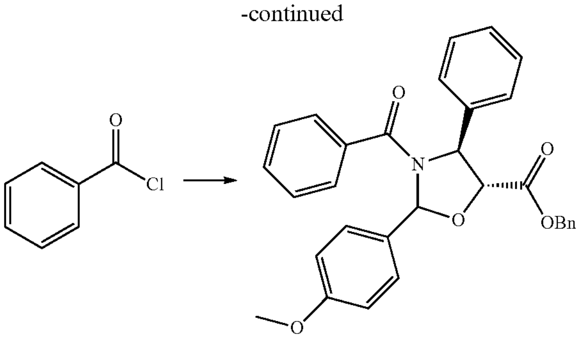

Benzyl (4S,5R)-2-(4-methoxyphenyl)-4-phenyl-5-oxazolidine carboxylate (1 eq.) was dissolved in dry tetrahydrofuran, into which 1.5 equivalents of LHMDS was added at −40° C. After 1 hour of reaction, the reaction liquid was added dropwise with 2 equivalents of benzoyl chloride, reacted for 3 hours and finished the reaction. After post-treatment of purification by column chromatography, the product was obtained in a yield of 85%.

The preparation of 7,10-dimethoxyl-1,14-carbonate baccatin III in Step 2) and PCMI-02 in Step 3) had the same procedures as those in Step 2) and Step 3) in Example 1. The procedures could be seen particularly in Step 2) and Step 3) in Example 1 and the purity of the final product was 95% or higher.

PCMI-02: mp: 234-235° C.;

MS (m/z) ESI: 904.3 $(M+Na)^+$;

$^1H$ NMR (400 MHz, $CDCl_3$) δ 8.14 (d, J=8.0 Hz, 2H), 7.80 (d, J=7.9 Hz, 2H), 7.62 (t, J=7.1 Hz, 1H), 7.53-7.44 (m, 7H), 7.38 (t, J=7.4 Hz, 3H), 7.20 (d, J=8.9 Hz, 1H), 6.49 (d, J=6.6 Hz, 1H), 6.08 (d, J=7.6 Hz, 1H), 5.95 (dd, J=8.8, 3.0 Hz, 1H), 4.97 (d, J=8.8 Hz, 1H), 4.92-4.88 (m, 2H, H-2'), 4.71 (s, 1H), 4.29 (q, J=8.5 Hz, 2H), 3.98 (d, J=5.1 Hz, 1H), 3.86 (m, 1H), 3.73 (d, J=7.5 Hz, 1H), 3.48 (s, 3H), 3.31 (s, 3H), 2.78-2.65 (m, 1H), 2.56 (s, 3H), 1.88 (s, 3H), 1.85-1.74 (m, 4H), 1.31 (s, 3H), 1.28 (s, 3H).

$^{13}C$ NMR (101 MHz, $CDCl_3$) δ 203.54, 172.05, 171.20, 167.55, 164.79, 151.88, 137.66, 136.28, 135.77, 134.10, 133.55, 131.98, 130.12, 129.03, 128.61, 128.30, 128.05, 127.33, 126.86, 88.25, 84.07, 82.08, 81.10, 80.39, 79.82, 76.07, 74.88, 73.97, 69.25, 57.92, 57.08, 55.02, 46.81, 41.86, 31.79, 29.70, 25.98, 24.89, 22.70, 22.28, 14.49, 10.46.

Example 3 Preparation of PCMI-03

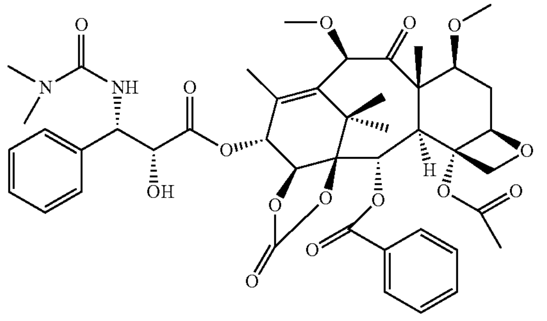

1) Preparation of (4S,5R)-3-dimethylcarbamoyl-2-(4-methoxyphenyl)-4-phenyl-5-oxazolidine carboxylic acid

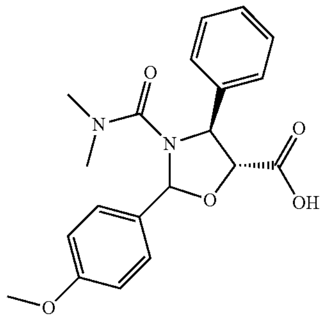 [SMILES: COc1ccc(C2O[C@@H](C(=O)O)[C@H](c3ccccc3)N2C(=O)N(C)C)cc1]

(4S,5R)-3-dimethylcarbamoyl-2-(4-methoxyphenyl)-4-phenyl-5-oxazolidine carboxylic acid was prepared with the substantially same method as shown in Example 1, except for Step g. Other steps could be seen in the reactions of Example 1.

g. Preparation of benzyl (4S,5R)-3-dimethylcarbamoyl-2-(4-methoxyphenyl)-4-phenyl-5-oxazolidine carboxylate

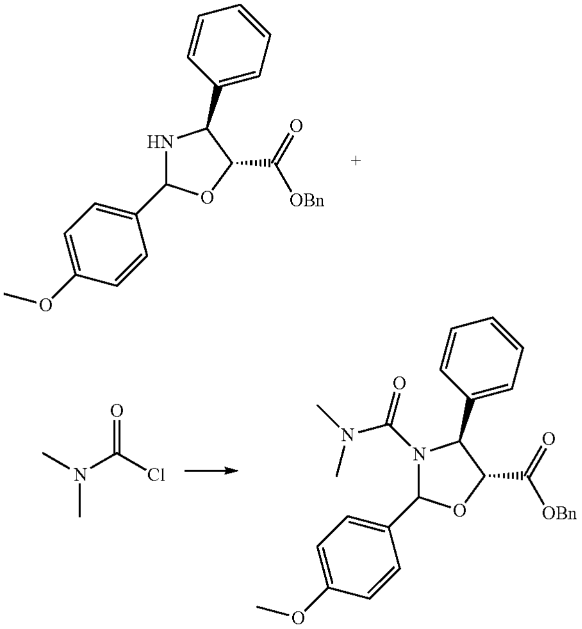

Benzyl (4S,5R)-2-(4-methoxyphenyl)-4-phenyl-5-oxazolidine carboxylate (1 eq.) was dissolved in dry tetrahydrofuran, into which 1.5 equivalents of LHMDS was added at −40° C. After 1 hour of reaction, the reaction liquid was added dropwise with 2 equivalents of dimethylcarbamoyl chloride, reacted for 3 hours and finished the reaction. After post-treatment of purification by column chromatography, the product was obtained in a yield of 80%.

The preparation of 7,10-dimethoxyl-1,14-carbonate baccatin III in Step 2) and PCMI-03 in Step 3) had the same procedures as those in Step 2) and Step 3) in Example 1. The procedures could be seen particularly in Step 2) and Step 3) in Example 1 and the purity of the final product was 95% or higher.

PCMI-03: mp: 205-206° C.;

MS (m/z) ESI: 871.5 $(M+Na)^+$;

$^1$H NMR (400 MHz, $CDCl_3$) δ 8.10 (d, J=7.2 Hz, 2H), 7.63 (t, J=7.4 Hz, 1H), 7.49 (t, J=7.7 Hz, 2H), 7.43 (d, J=7.2 Hz, 2H), 7.38 (t, J=7.4 Hz, 2H), 7.35-7.29 (m, 1H), 6.11 (t, J=8.1 Hz, 1H), 5.97-5.88 (m, 1H), 5.80 (d, J=6.1 Hz, 1H), 5.67 (d, J=9.7 Hz, 1H), 5.30 (d, J=9.3 Hz, 1H), 4.93 (d, J=8.7 Hz, 1H), 4.63 (s, 1H), 4.29 (d, J=8.3 Hz, 1H), 4.17 (d, J=8.3 Hz, 1H), 3.97 (t, J=11.1 Hz, 1H), 3.01 (d, J=6.0 Hz, 1H), 2.64-2.52 (m, 1H), 2.38 (dd, J=15.3, 10.0 Hz, 1H), 2.28 (d, J=11.0 Hz, 5H), 2.16-2.10 (m, 1H), 2.11 (s, 3H), 1.88-1.82 (m, 1H) 1.73 (s, 6H), 1.42 (s, 12H), 1.25 (s, 3H).

$^{13}$C NMR (101 MHz, $CDCl_3$) δ 171.64, 171.21, 170.78, 170.62, 167.10, 155.18, 138.80, 137.60, 136.85, 133.72, 130.09, 129.20, 128.65, 128.58, 127.82, 127.04, 84.73, 82.82, 79.96, 78.61, 76.58, 73.96, 72.18, 70.96, 69.23, 60.42, 55.89, 44.99, 42.98, 42.33, 37.36, 36.66, 35.66, 29.70, 28.30, 22.60, 21.81, 21.40, 16.71, 14.94.

Example 4 Preparation of PCMI-04

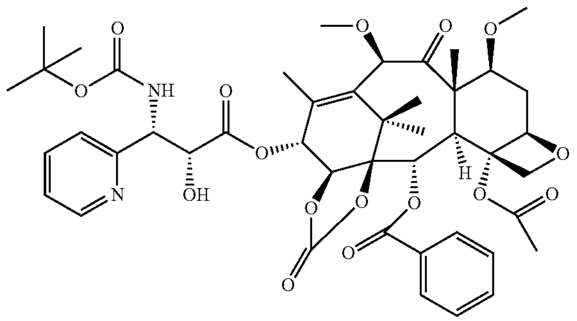

1) Preparation of (4S,5R)-3-t-butyloxycarbonyl-2-(4-methoxyphenyl)-4-(2-pyridyl)-5-oxazolidine carboxylic acid

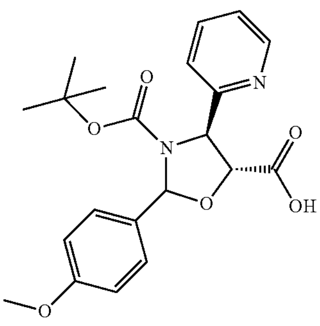 [SMILES: COc1ccc(C2O[C@@H](C(=O)O)[C@H](c3ccccn3)N2C(=O)OC(C)(C)C)cc1]

(4S,5R)-3-t-butyloxycarbonyl-2-(4-methoxyphenyl)-4-(2-pyridyl)-5-oxazolidine-carboxylic acid was prepared with the substantially same method as shown in Example 1, except for Step c. Other steps could be seen in the reaction of Example 1.

c. Preparation of N-t-butyl sulfinyl-2-pyridinyl carboxaenamine

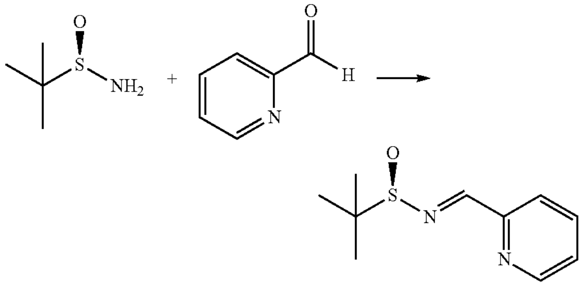

($S_R$)-t-butyl sulfinamide (5.22 g, 0.043 mol) and 2-pyridine carboxaldehyde (4.47 g, 0.052 mol) were dissolved in 20 ml of dichloromethane, into which magnesium sulfate (25.90 g, 0.22 mol) and PPTS (0.54 g, 2.20 mmol) were added. The reaction liquid was stirred at room temperature for 24 hours, filtered and the filter cake was rinsed with dichloromethane for 3 times (20 ml×3) and concentrated to give the crude product. The crude product was purified by column chromatography (petroleum ether/ethyl acetate=15:1) to give a colorless oil (7.13 g, 80.2%).

The preparation of 7,10-dimethoxyl-1,14-carbonate baccatin III in Step 2) and PCMI-04 in Step 3) had the same procedures as those in Step 2) and Step 3) in Example 1. The procedures could be seen particularly in Step 2) and Step 3) in Example 1 and the purity of the final product was 95% or higher.

PCMI-04: mp: 244-245° C.;

MS (m/z) ESI: 901.3 $(M+Na)^+$;

$^1$H NMR (400 MHz, $CDCl_3$) δ 8.46 (d, J=4.5 Hz, 1H), 8.06-7.99 (m, 2H), 7.83-7.75 (m, 1H), 7.62 (t, J=7.5 Hz, 1H), 7.49 (t, J=7.8 Hz, 3H), 7.29 (m, 1H), 6.39 (dd, J=6.7, 1.4 Hz, 1H), 6.08 (d, J=7.4 Hz, 1H), 5.81 (d, J=10.0 Hz, 1H), 5.49-5.39 (m, 1H), 4.99 (d, J=8.2 Hz, 1H), 4.82 (d, J=6.7 Hz, 1H), 4.78 (s, 1H), 4.73 (s, 1H), 4.30 (d, J=8.3 Hz, 1H), 4.22 (d, J=8.2 Hz, 1H), 3.89 (dd, J=10.8, 6.3 Hz, 1H), 3.72 (d, J=3.7 Hz, 1H), 3.45 (s, 3H), 3.31 (s, 3H), 2.77-2.67 (m, 1H, H-6), 2.52 (s, 3H), 1.92 (d, J=1.0 Hz, 3H), 1.82-1.77 (dd, J=19.3, 7.9 Hz, 1H), 1.76 (s, 3H), 1.48 (s, 9H), 1.30 (s, 3H), 1.24 (s, J=8.0 Hz, 3H).

$^{13}$C NMR (101 MHz, $CDCl_3$) δ 203.62, 171.02, 164.65, 159.41, 152.08, 148.04, 137.91, 136.46, 136.21, 134.12, 129.86, 128.90, 123.04, 122.28, 88.26, 83.97, 82.23, 80.91, 80.40, 80.05, 75.93, 73.92, 69.37, 57.87, 57.10, 57.03, 46.82, 41.85, 31.82, 29.68, 28.34, 26.00, 22.07, 14.55, 10.37.

Example 5 Preparation of PCMI-05

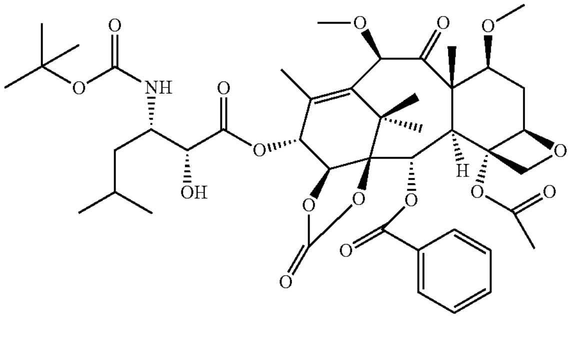

1) Preparation of (4S,5R)-3-t-butyloxycarbonyl-2-(4-methoxyphenyl)-4-isobutyl-5-oxazolidine carboxylic acid

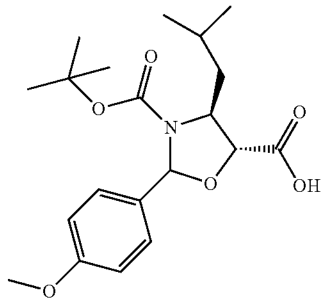 [SMILES: COc1ccc(C2O[C@@H](C(=O)O)[C@H](CC(C)C)N2C(=O)OC(C)(C)C)cc1]

(4S,5R)-3-t-butyloxycarbonyl-2-(4-methoxyphenyl)-4-isobutyl-5-oxazolidine carboxylic acid was prepared with the substantially same method as shown in Example 1, except for Step c. Other steps could be seen in the reaction of Example 1.

c. Preparation of N-t-butyl sulfinyl isobutyl carboxaenamine

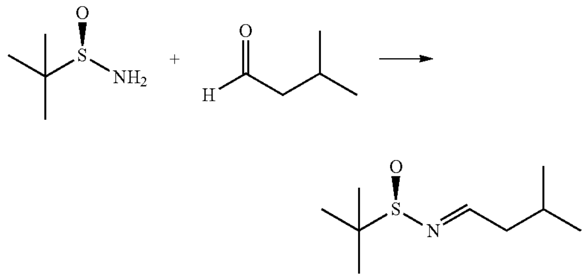

($S_R$)-t-butyl sulfinamide (5.22 g, 0.043 mol) and isovaleraldehyde (5.51 g, 0.052 mol) were dissolved in 20 ml of dichloromethane, into which magnesium sulfate (25.90 g, 0.22 mol) and PPTS (0.54 g, 2.20 mmol) were added. The reaction liquid was stirred for 24 hours at room temperature, filtered and the filter cake was rinsed with dichloromethane for 3 times (20 ml×3) and concentrated to give the crude product. The crude product was purified by column chromatography (petroleum ether/ethyl acetate=15:1) to give a colorlss oil (7.26 g, 89.3%).

The preparation of 7,10-dimethoxyl-1,14-carbonate baccatin III in Step 2) and PCMI-05 in Step 3) had the same procedures as those in Step 2) and Step 3) in Example 1. The procedures could be seen particularly in Step 2) and Step 3) in Example 1 and the purity of the final product was 95% or higher.

PCMI-05: mp: 237-238° C.;

MS (m/z) ESI: 880.4 $(M+Na)^+$;

$^1$H NMR (400 MHz, $CDCl_3$) δ 8.03 (d, J=7.5 Hz, 2H), 7.61 (t, J=7.4 Hz, 1H), 7.48 (t, J=7.7 Hz, 2H), 6.46 (d, J=6.2 Hz, 1H), 6.08 (d, J=7.5 Hz, 1H), 4.97 (d, J=7.9 Hz, 1H), 4.84 (d, J=6.8 Hz, 1H), 4.80 (d, J=9.1 Hz, 1H), 4.74 (s, 1H), 4.33 (dd, J=6.2, 3.2 Hz, 1H), 4.29 (d, J=8.4 Hz, 1H), 4.23 (d, J=8.4 Hz, 1H), 4.17-4.07 (m, 1H), 4.03 (d, J=6.2 Hz, 1H), 3.86 (dd, J=10.7, 6.4 Hz, 1H), 3.71 (d, J=7.4 Hz, 1H), 3.47 (s, 3H), 3.30 (s, 3H), 2.70 (ddd, J=14.3, 9.8, 6.3 Hz, 1H), 2.49 (s, 3H), 1.96 (d, J=1.2 Hz, 3H), 1.86-1.77 (m, 1H), 1.76 (s, 3H), 1.73-1.67 (m, 2H) 1.521.42 (m, 1H), 1.39 (s, 9H), 1.31 (d, J=5.9 Hz, 6H), 0.99 (t, J=6.5 Hz, 6H).

$^{13}$C NMR (101 MHz, $CDCl_3$) δ 203.58, 172.84, 170.75, 164.68, 156.23, 152.06, 136.25, 134.08, 129.92, 128.93, 128.06, 88.16, 83.98, 82.17, 81.03, 80.36, 79.73, 75.95, 74.73, 73.81, 69.22, 57.85, 57.09, 57.07, 46.74, 41.92, 31.80, 29.69, 28.24, 26.04, 24.86, 23.25, 22.55, 22.16, 14.66, 10.41.

Example 6 Preparation of PCMI-06

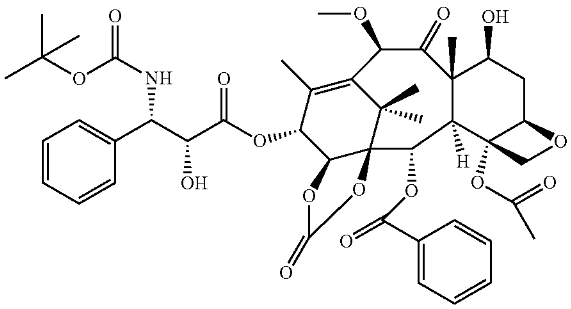

1) Preparation of (4S,5R)-3-t-butyloxycarbonyl-2-(4-methoxyphenyl)-4-phenyl-5-oxazolidine carboxylic acid The specific method was seen in Example 1.

2) Preparation of 10-methoxyl-7-triethylsilicane-1,14-carbonate baccatin III

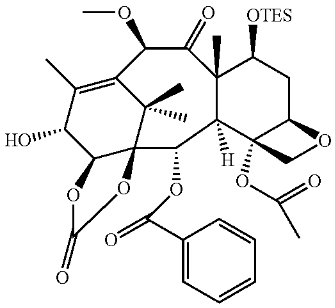

10-DAB (1 eq.) was used as raw material, dissolved in DMF and added successively with 2.5 equivalents of imidazole and 2.5 equivalents of triethyl chlorosilane. By post-treatment, the crude compound 7 was given.

The compound 7 was dissolved in dichloromethane which was used as the solvent, into which 2 equivalents of pyridine was added at 0° C. Successively, the reaction liquid was added dropwise with 2 equivalents of p-toluenesulfonyl chloride to react for 4 hours. By post-treatment of purification by column chromatography, the compound 8 was given in a yield of 85-90%.

The compound 8 (1 eq.) was dissolved in anhydrous tetrahydrofuran to react with methyl magnesium bromide (2 eq.) at room temperature for 3 hours under the protection of nitrogen. After post-treatment, the crude compound 9 was obtained after dried.

The compound 9 (1 eq.) was dissolved in acetone solution, into which 10 equivalents of manganese dioxide was added to react for 4 hours at room temperature. By post-treatment of purification by column chromatography, the compound 10 was given in a yield of 75%.

The compound 10 (1 eq.) was dissolved in dry THF/DMPU (4:1) solution, into which 1.2 equivalents of potassium t-butoxide was added at −70° C. to react for 20 min. The obtained reaction liquid was slowly added dropwise with 2 equivalents of N-(sulfonyl)oxaziridine to react for 2 hours. By post-treatment of purification by column chromatography, the compound 11 was given in a yield of 75%.

The compound 11 (1 eq.) was reacted with 2 equivalents of N,N'-carbonyldiimidazole (CDI) in dry tetrahydrofuran to give the compound 12 in a yield of 95%.

The compound 12 (1 eq.) was dissolved in dry tetrahydrofuran, into which 0.2 equivalents of (R)-2-methyl oxazaborodine was added at room temperature as a catalyst, followed by addition of 5 equivalents of borane/THF solution to react for 8 hours. After completion of reaction, by post-treatment of purification by column chromatography, the compound 13 of 10-methoxyl-1,14-carbonate baccatin III was obtained as the final product in a yield of 80%.

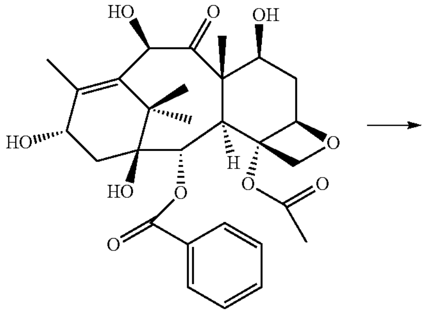

10-DAB

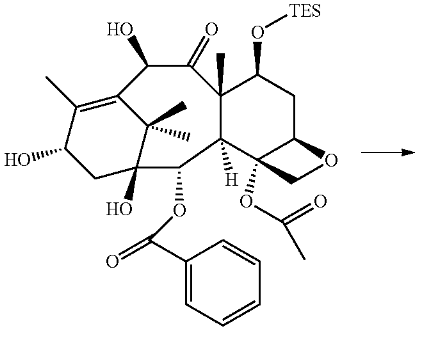

7

-continued

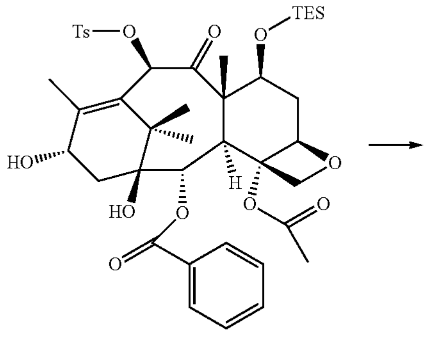

8

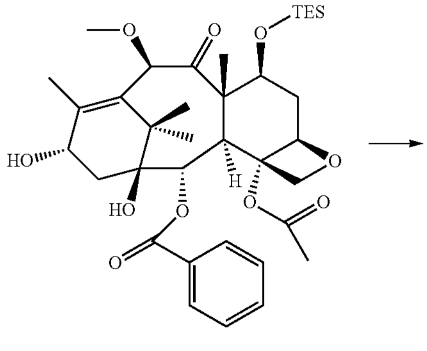

9

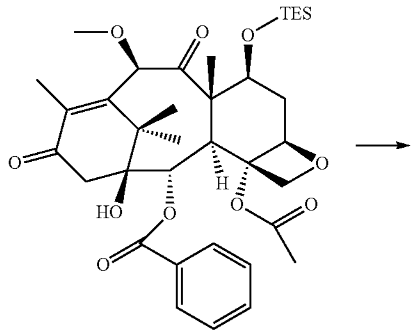

10

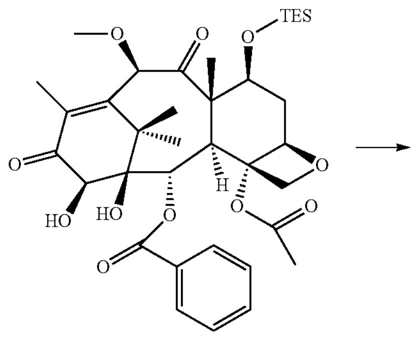

11

-continued

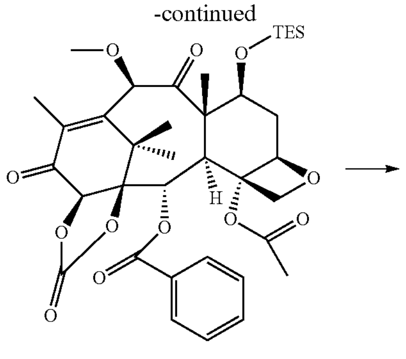

12

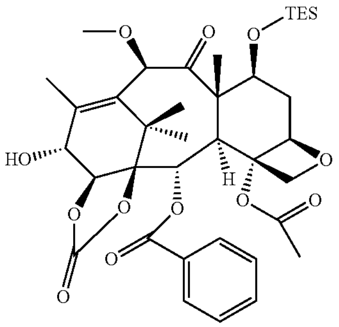

13

3) Preparation of PCMI-06

The specific method was seen in Step 3) in Example 1 and the purity of the final product was 95% or higher.

PCMI-06: mp: 233-235° C.;

MS (m/z) ESI: 886.3 $(M+Na)^+$;

$^1H$ NMR (400 MHz, $CDCl_3$) δ 8.02 (d, J=7.5 Hz, 2H), 7.62 (t, J=7.4 Hz, 1H), 7.49 (t, J=7.7 Hz, 2H), 7.46-7.37 (m, 4H), 7.37-7.30 (m, 1H), 6.46 (d, J=6.2 Hz, 1H), 6.10 (d, J=7.6 Hz, 1H), 5.51 (d, J=7.4 Hz, 1H), 5.33 (s, 1H), 4.92 (d, J=7.9 Hz, 1H), 4.87 (s, 1H), 4.78 (d, J=6.8 Hz, 1H), 4.71 (s, 1H), 4.28 (d, J=8.5 Hz, 1H), 4.22 (t, J=6.8 Hz, 2H), 3.73 (d, J=7.4 Hz, 1H), 3.44 (s, 3H), 2.55 (ddd, J=15.8, 9.6, 6.5 Hz, 1H), 2.43 (s, 3H), 1.91-1.79 (m, 4H), 1.73 (s, 3H), 1.38 (s, 9H), 1.30 (d, J=2.5 Hz, 6H).

$^{13}C$ NMR (101 MHz, $CDCl_3$) δ 205.25, 170.66, 164.75, 151.96, 136.44, 135.77, 134.17, 129.95, 128.98, 128.17, 127.99, 126.66, 88.11, 84.13, 82.19, 80.74, 79.63, 76.07, 74.41, 71.66, 69.34, 60.46, 58.02, 57.36, 46.23, 41.77, 36.79, 28.25, 25.73, 22.54, 22.22, 14.51, 9.83.

Example 7 Preparation of PCMI-07

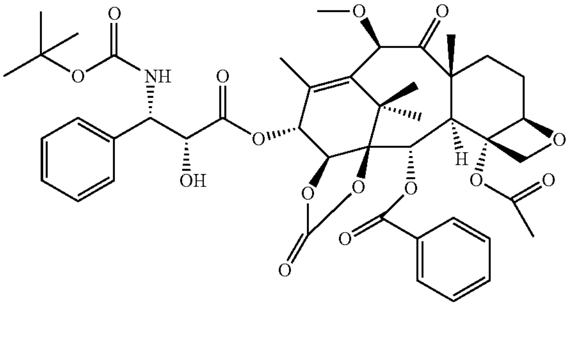

1) Preparation of (4S,5R)-3-t-butyloxycarbonyl-2-(4-methoxyphenyl)-4-phenyl-5-oxazolidine carboxylic acid The specific method was seen in Example 1.

2) Preparation of 10-methoxyl-7-dihydro-1,14-carbonate baccatin III

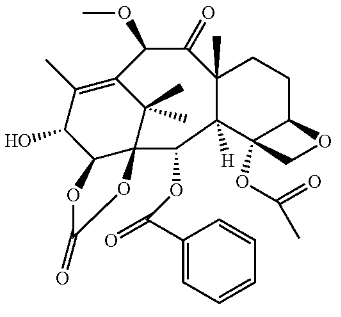

10-DAB (1 eq.) was used as raw material, dissolved in DMF and added successively with 2.5 equivalents of imidazole and 2.5 equivalents of triethyl chlorosilane. By post-treatment, the crude compound 7 was given.

The compound 7 was dissolved in dichloromethane which was used as the solvent, into which 2 equivalents of pyridine was added at 0° C. Successively, the reaction liquid was added dropwise with 2 equivalents of p-toluenesulfonyl chloride to react for 4 hours. By post-treatment of purification by column chromatography, the compound 8 was given in a yield of 85-90%.

The compound 8 (1 eq.) was dissolved in anhydrous tetrahydrofuran to react with methyl magnesium bromide (2 eq.) at room temperature for 3 hours under the protection of nitrogen. After post-treatment, the crude compound 9 was obtained after dried.

The compound 9 (1 eq.) was dissolved in dry THF, into which 1.5 equivalents of tetrabutylammonium fluoride (which is in the form of a solution in THF) was added at room temperature. After 1 hour of reaction, the reaction was completed. By post-treatment of purification by column chromatography, the compound 14 was given in a yield of 92%.

The compound 14 (1 eq.) was dissolved in dry THF, into which 8 equivalents of N,N'-carbonyldiimidazole (CDI) was added at room temperature. After 2 hour of reaction, the reaction was completed. By post-treatment of purification by column chromatography, the compound 15 was obtained in a yield of 78%.

The compound 15 (1 eq.) was dissolved in the solution of dioxane/tetrahydrofuran (10:1). 0.2 Equivalents of azobisisobutyronitrile was added at 100° C. as a catalyst to induce free radicals reaction. Afterward, the reaction liquid was added with 4 equivalents of n-butyl tin hydride ($Bu_3SnH$) to react for 1 hour, cooled at room temperature overnight. By purification by column chromatography, the compound 16 was given in a yield of 52%.

The compound 16 (1 eq.) was dissolved in acetone solution, into which 10 equivalents of manganese dioxide was added at room temperature to react for 4 hours. By post-treatment of purification by column chromatography, the compound 17 was given in a yield of 75%.

The compound 17 (1 eq.) was dissolved in dry THF/DMPU (4:1) solution, into which 1.2 equivalents of potassium t-butoxide was added at −70° C. to react for 20 min. The obtained reaction liquid was slowly added dropwise with 2 equivalents of N-(sulfonyl)oxaziridine to react for 2 hours. By post-treatment of purification by column chromatography, the compound 18 was given in a yield of 75%.

The compound 18 (1 eq.) was reacted with 2 equivalents of N,N'-carbonyldiimidazole (CDI) in dry tetrahydrofuran to give the compound 19 in a yield of 95%.

The compound 19 (1 eq.) was dissolved in dry tetrahydrofuran, into which 0.2 equivalents of (R)-2-methyl oxazaborodine was added at room temperature as a catalyst, followed by addition of 5 equivalents of borane/THF solution to react for 8 hours. After completion of reaction, by post-treatment of purification by column chromatography, the compound 20 of 10-methoxyl-7-dihydro-1,14-carbonate baccatin III was obtained as the final product in a yield of 80%.

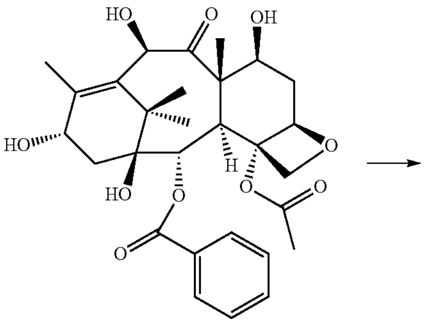

10-DAB

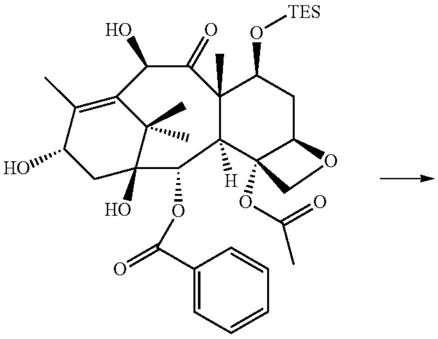

7

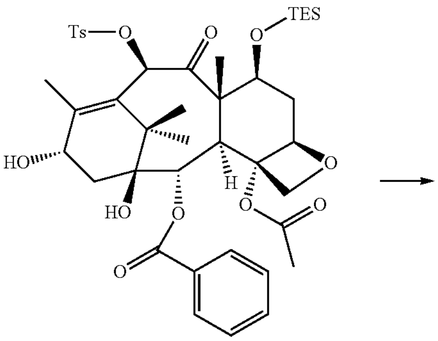

8

-continued

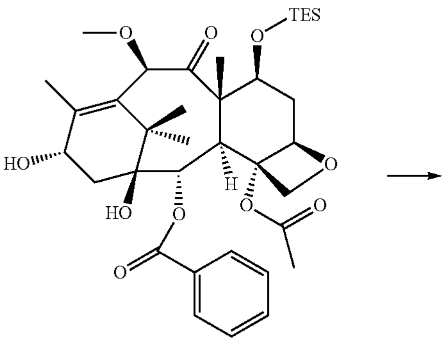

9

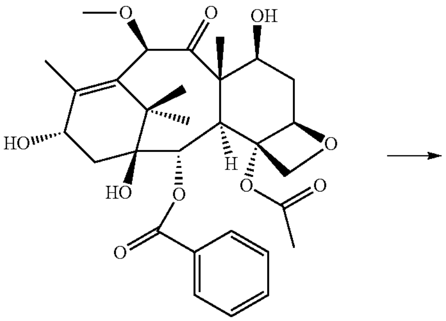

14

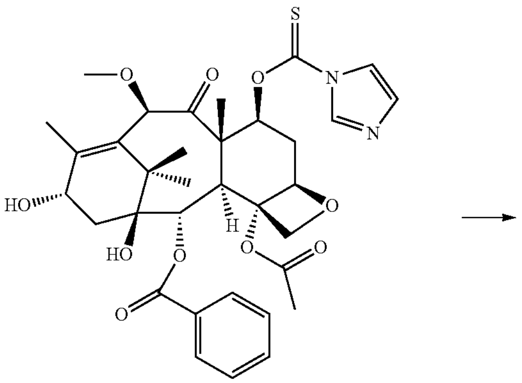

15

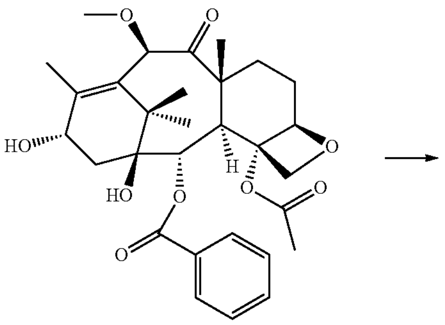

16

-continued

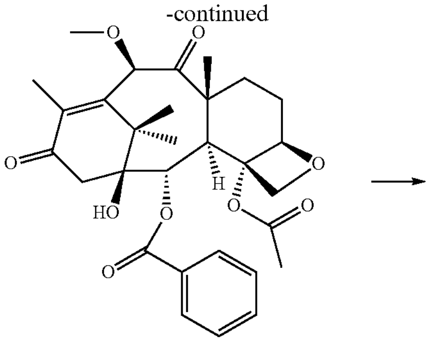

17

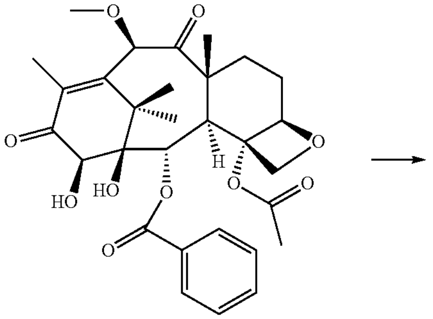

18

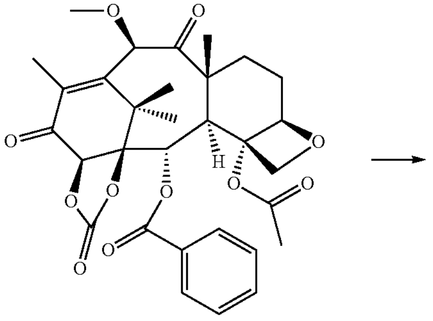

19

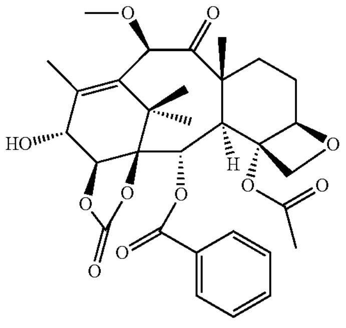

20

3) Preparation of PCMI-07

The specific method was seen in Step 3) in Example 1 and the purity of the final product was 95% or higher.

PCMI-07: mp: 226-227° C.;

MS (m/z) ESI: 870.3 $(M+Na)^+$;

$^1H$ NMR (400 MHz, $CDCl_3$) δ 8.05 (d, J=7.4 Hz, 2H), 7.61 (t, J=7.4 Hz, 1H), 7.50 (t, J=7.7 Hz, 3H), 7.47-7.31 (m, 5H), 6.46 (d, J=6.3 Hz, 1H), 6.09 (d, J=7.8 Hz, 1H), 5.43 (d, J=9.0 Hz, 1H,), 5.35 (s, 1H), 4.90 (d, J=8.0 Hz, 1H), 4.86 (s, 1H), 4.82 (d, J=7.0 Hz, 1H), 4.70 (s, 1H), 4.28 (s, 2H), 3.66 (d, J=7.7 Hz, 1H), 3.58 (s, 1H), 3.46 (s, 3H), 2.43 (s, 3H), 2.23 (dd, J=15.0, 6.1 Hz, 1H), 2.04-1.93 (m, 2H), 1.89 (d, J=1.1 Hz, 3H), 1.80 (s, 3H), 1.59 (dd, J=11.9, 5.7 Hz, 1H), 1.38 (s, 9H), 1.30 (s, 3H), 1.26 (s, 3H).

$^{13}C$ NMR (101 MHz, $CDCl_3$) δ 207.81, 171.18, 164.83, 151.95, 136.00, 134.05, 129.97, 129.01, 128.94, 128.19, 128.16, 126.59, 88.25, 84.31, 81.75, 81.02, 80.67, 79.59, 76.20, 74.43, 70.08, 57.20, 53.30, 41.52, 35.53, 31.93, 29.70, 28.23, 27.02, 25.35, 22.70, 22.10, 14.93, 14.31.

Example 8 Preparation of PCMI-08

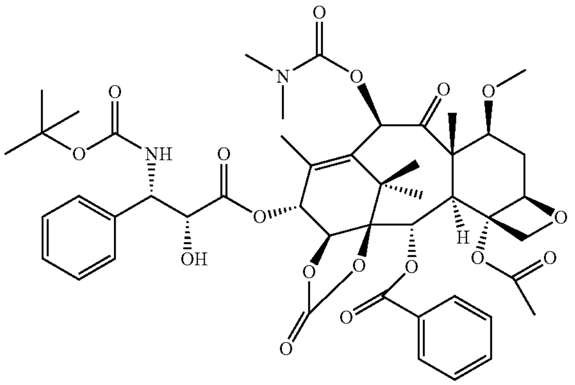

1) Preparation of (4S,5R)-3-t-butyloxycarbonyl-2-(4-methoxyphenyl)-4-phenyl-5-oxazolidine carboxylic acid The specific method was seen in Step 1) in Example 1.

2) Preparation of 10-dimethylcarbamoyl-7-methoxyl-1,14-carbonate baccatin III

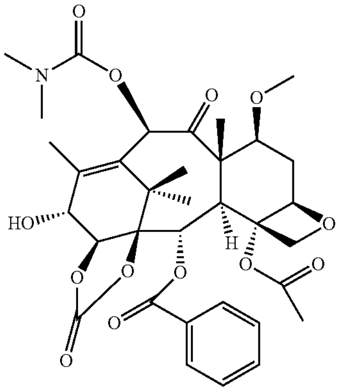

10-DAB (1 eq.) was used as raw material, dissolved in DMF and added successively with 2.5 equivalents of imidazole and 2.5 equivalents of triethyl chlorosilane. By post-treatment, the crude compound 7 was given.

The compound 7 (1 eq.) was dissolved in dry THF which was used as the solvent, into which 1.5 equivalents LHMDS was added at 0° C. After 1 hour of reaction, 2 equivalents of dimethylcarbamoyl chloride was slowly added dropwise to the reaction liquid and reacted for 2 hours. By post-treatment of purification by column chromatography, the compound 21 was given in a yield of 87%.

The compound 21 (1 eq.) was dissolved in acetone solution, into which 10 equivalents of manganese dioxide was added at room temperature to react for 4 hours. By post-treatment of purification by column chromatography, the compound 22 was given in a yield of 75%.

The compound 22 (1 eq.) was dissolved in dry THF, into which 1.5 equivalents of tetrabutylammonium fluoride (which is in the form of a solution in THF) was added at room temperature. After 1 hour of reaction, the reaction was completed. By post-treatment of purification by column chromatography, the compound 23 was given in a yield of 90%.

The compound 23 was reacted with p-toluenesulfonyl chloride to give the compound 24.

The compound 24 (1 eq.) was dissolved in anhydrous tetrahydrofuran to react with methyl magnesium bromide (2 eq.) at room temperature for 3 hours under the protection of nitrogen. After post-treatment, the crude compound 25 was obtained after dried.

The compound 25 (1 eq.) was dissolved in dry THF/DMPU (4:1) solution, into which 1.2 equivalents of potassium t-butoxide was added at −70° C. to react for 20 min. The obtained reaction liquid was slowly added dropwise with 2 equivalents of N-(sulfonyl)oxaziridine to react for 2 hours. By post-treatment of purification by column chromatography, the compound 26 was given in a yield of 75%.

The compound 26 (1 eq.) was reacted with 2 equivalents of N,N'-carbonyldiimidazole (CDI) in dry tetrahydrofuran to give the compound 27 in a yield of 95%.

The compound 27 (1 eq.) was dissolved in dry tetrahydrofuran, into which 0.2 equivalents of (R)-2-methyl oxazaborodine was added at room temperature as a catalyst, followed by addition of 5 equivalents of borane/THF solution to react for 8 hours. After completion of reaction, by post-treatment of purification by column chromatography, the compound 28 of 10-dimethylcarbamoyl-7-methoxy-1,14-carbonate baccatin III was obtained as the final product in a yield of 80%.

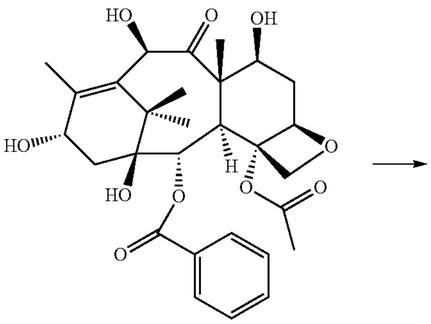

10-DAB

-continued

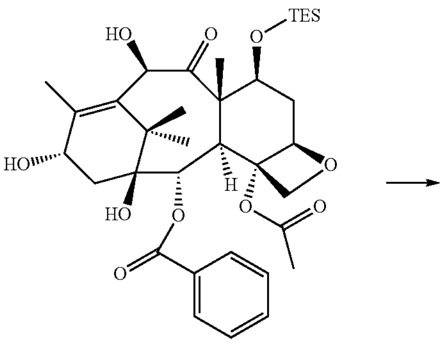

7

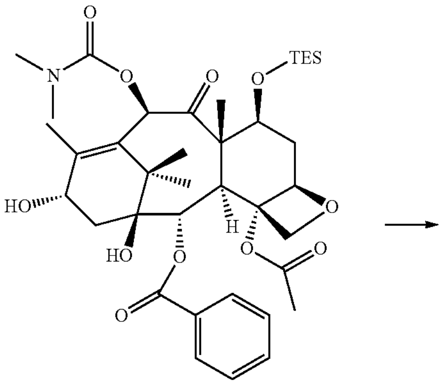

21

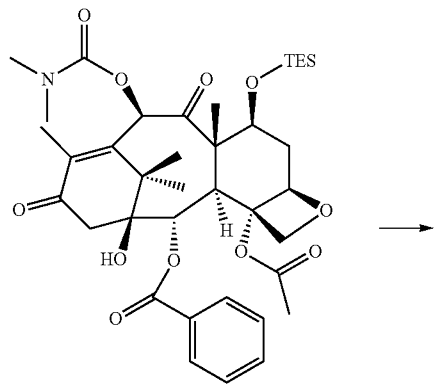

22

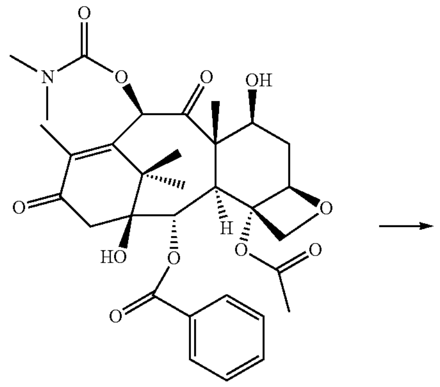

23

-continued

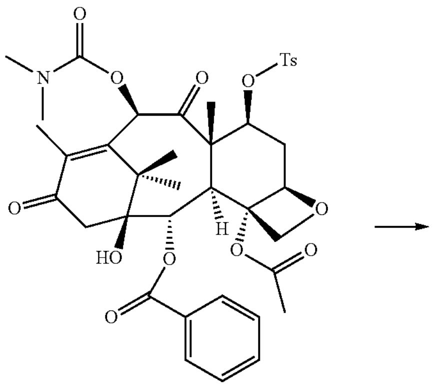

24

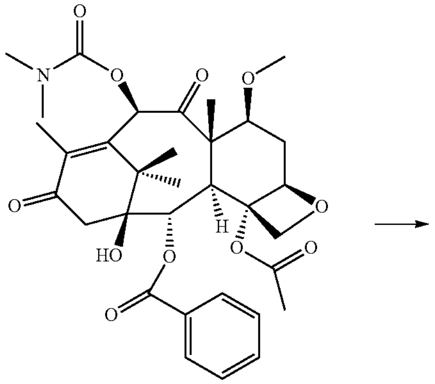

25

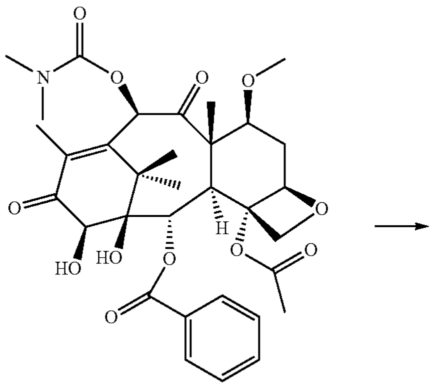

26

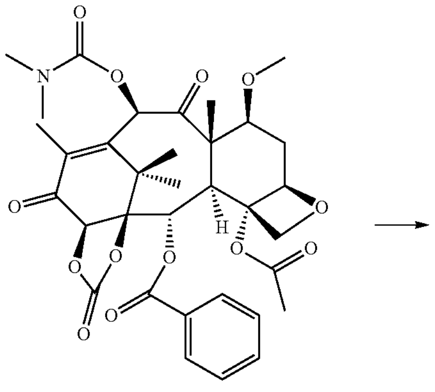

27

-continued

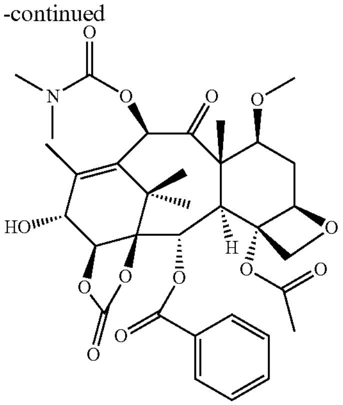

28

3) Preparation of PCMI-08

The specific method was seen in Step 3) in Example 1 and the purity of the final product was 95% or higher.

PCMI-08: mp: 246-247° C.;

MS (m/z) ESI: 957.5 $(M+Na)^+$;

$^1H$ NMR (400 MHz, $CDCl_3$) δ 8.04 (d, J=7.5 Hz, 2H), 7.63 (t, J=7.4 Hz, 1H), 7.50 (t, J=7.7 Hz, 2H), 7.45-7.31 (m, 5H), 6.45 (d, J=6.0 Hz, 1H), 6.39 (s, 1H), 6.11 (d, J=7.4 Hz, 1H), 5.55 (d, J=8.7 Hz, 1H), 5.35 (s, 1H), 4.96 (d, J=8.2 Hz, 1H), 4.82 (d, J=6.6 Hz, 1H), 4.71 (s, 1H), 4.29 (d, J=8.5 Hz, 1H), 4.22 (d, J=8.4 Hz, 1H), 3.86 (dd, J=10.6, 6.5 Hz, 1H), 3.78 (d, J=7.8 Hz, 1H), 3.35 (s, 3H), 3.07 (s, 3H), 2.98 (s, 3H), 2.72 (ddd, J=14.6, 9.7, 6.5 Hz, 1H), 2.46 (s, 3H), 1.98 (d, J=0.9 Hz, 3H), 1.85-1.74 (m, 4H), 1.40 (s, 9H), 1.36 (s, 3H), 1.32 (s, 3H).

$^{13}C$ NMR (101 MHz, $CDCl_3$) δ 202.12, 171.91, 171.24, 170.81, 164.68, 155.71, 154.81, 151.92, 138.16, 137.39, 134.64, 134.15, 129.93, 128.95, 128.12, 128.01, 126.63, 88.01, 84.02, 81.04, 80.60, 80.16, 79.68, 75.91, 75.00, 74.74, 74.34, 69.12, 57.81, 57.36, 46.68, 41.83, 36.81, 36.21, 32.12, 28.26, 25.87, 22.75, 22.62, 14.55, 10.39.

Example 9 Preparation of PCMI-09

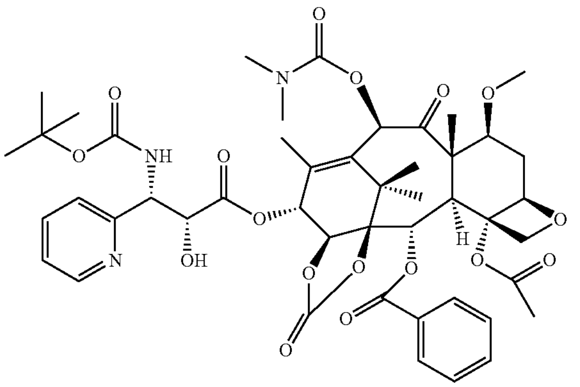

1) Preparation of (4S,5R)-3-t-butyloxycarbonyl-2-(4-methoxyphenyl)-4-(2-pyridyl)-5-oxazolidine carboxylic acid The specific method was seen in Step 1) in Example 4.

2) Preparation of 10-dimethylcarbamoyl-7-methoxyl-1,14-carbonate baccatin III

The specific method was seen in Step 2) in Example 8.

3) Preparation of PCMI-09

The specific method was seen in Step 3) in Example 1 and the purity of the final product was 95% or higher.

PCMI-09: mp: 241-242° C.;

MS (m/z) ESI: 958.3 $(M+Na)^+$;

$^1H$ NMR (400 MHz, $CDCl_3$) δ 8.06 (d, J=7.6 Hz, 2H), 7.63 (t, J=7.4 Hz, 1H), 7.50 (t, J=7.7 Hz, 2H), 6.48 (d, J=6.3 Hz, 1H), 6.42 (s, 1H), 6.14 (d, J=7.4 Hz, 1H), 4.95 (d, J=8.3 Hz, 1H), 4.89 (d, J=6.9 Hz, 1H), 4.77 (d, J=9.0 Hz, 1H), 4.33 (dd, J=8.9, 5.8 Hz, 2H), 4.27 (d, J=8.4 Hz, 1H), 4.22-4.09 (m, 1H), 3.93-3.83 (m, 2H, H-7), 3.77 (d, J=7.3 Hz, 1H), 3.41 (s, 3H), 2.88 (s, 6H), 2.60-2.41 (m, 4H), 2.02 (s, 3H), 1.96 (dd, J=19.7, 7.7 Hz, 1H), 1.85 (s, 3H), 1.75-1.69 (m, 1H), 1.52-1.37 (m, 11H), 1.30 (s, 3H), 1.27 (s, 3H), 1.01 (t, J=6.3 Hz, 6H).

$^{13}C$ NMR (101 MHz, $CDCl_3$) δ 205.08, 172.96, 170.35, 164.81, 154.97, 152.01, 136.39, 134.05, 129.95, 128.94, 128.11, 88.09, 84.03, 80.96, 80.39, 80.16, 79.69, 75.89, 75.02, 74.64, 73.84, 69.17, 57.29, 57.07, 51.49, 45.88, 41.76, 40.57, 36.54, 35.86, 33.76, 29.67, 28.24, 25.57, 24.85, 23.24, 22.46, 22.08, 14.42, 10.90.

Example 10 Preparation of PCMI-10

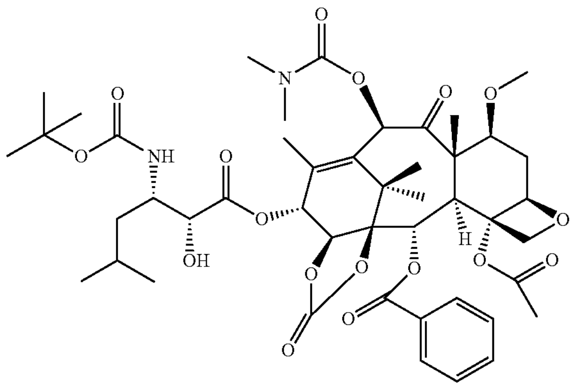

1) Preparation of (4S,5R)-3-t-butyloxycarbonyl-2-(4-methoxyphenyl)-4-isobutyl-5-oxazolidine carboxylic acid The specific method was seen in Step 1) in Example 5.

2) Preparation of 10-dimethylcarbamoyl-7-methoxyl-1,14-carbonate baccatin III

The specific method was seen in Step 2) in Example 8.

3) Preparation of PCMI-10

The specific method was seen in Step 3) in Example 1 and the purity of the final product was 95% or higher.

PCMI-10: mp: 236-237° C.;

MS (m/z) ESI: 937.4 $(M+Na)^+$;

$^1H$ NMR (400 MHz, $CDCl_3$) δ 8.05 (d, J=7.4 Hz, 2H), 7.63 (t, J=7.4 Hz, 1H), 7.50 (t, J=7.7 Hz, 2H), 6.47 (d, J=6.3 Hz, 1H), 6.41 (s, 1H), 6.13 (d, J=7.4 Hz, 1H), 4.98 (d, J=8.0 Hz, 1H), 4.89 (d, J=6.8 Hz, 1H), 4.77 (d, J=9.0 Hz, 1H), 4.37-4.32 (m, 1H), 4.30 (d, J=8.5 Hz, 1H), 4.24 (d, J=8.5 Hz, 1H), 4.17-4.06 (m, 1H), 4.04 (d, J=6.2 Hz, 1H), 3.88 (dd, J=10.6, 6.5 Hz, 1H), 3.77 (d, J=7.3 Hz, 1H), 3.36 (s, 3H), 3.08 (s, 3H), 2.99 (s, 3H), 2.74 (ddd, J=14.5, 9.7, 6.4 Hz, 1H), 2.52 (s, 3H), 2.04 (d, J=1.2 Hz, 3H), 1.88-1.77 (m, 5H), 1.77-1.66 (m, 3H), 1.41 (s, 11H), 1.37 (s, 3H), 1.34 (s, 3H), 1.01 (t, J=6.7 Hz, 6H).

$^{13}C$ NMR (101 MHz, $CDCl_3$) δ 202.17, 172.86, 170.75, 164.73, 156.27, 154.81, 151.99, 137.55, 134.58, 134.12, 129.94, 128.96, 128.03, 88.09, 84.03, 80.96, 80.39, 80.16, 79.69, 75.89, 75.02, 74.64, 73.84, 69.17, 57.83, 57.35, 51.68, 46.68, 41.86, 40.30, 36.81, 36.21, 32.10, 29.70, 28.24, 25.87, 24.87, 23.23, 22.56, 22.20, 14.65, 10.41.

Example 11 Preparation of PCMI-11

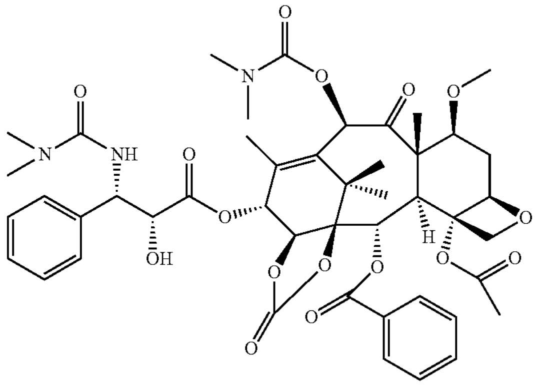

1) Preparation of (4S,5R)-3-dimethylcarbamoyl-2-(4-methoxyphenyl)-4-phenyl-5-oxazolidine carboxylic acid The specific method was seen in Step 1) in Example 3.

2) Preparation of 10-dimethylcarbamoyl-7-methoxyl-1,14-carbonate baccatin III

The specific method was seen in Step 2) in Example 8.

3) Preparation of PCMI-11

The specific method was seen in Step 3) in Example 1 and the purity of the final product was 95% or higher.

PCMI-11: mp: 241-242° C.;

MS (m/z) ESI: 928.5 $(M+Na)^+$;

$^1H$ NMR (400 MHz, $CDCl_3$) δ 8.03 (d, J=7.3 Hz, 2H), 7.62 (t, J=7.4 Hz, 1H), 7.49 (t, J=7.7 Hz, 2H), 6.08 (d, J=7.2 Hz, 1H), 5.49 (dd, J=10.7, 7.2 Hz, 1H), 5.23 (s, 1H), 5.04 (t, 1H), 4.97 (d, J=8.3 Hz, 1H), 4.80 (d, J=5.8 Hz, 1H), 4.32 (d, J=8.4 Hz, 1H), 4.22 (d, J=8.4 Hz, 1H), 3.87 (d, J=7.2 Hz, 1H), 3.67 (d, J=5.3 Hz, 1H), 3.40 (s, 3H), 2.87 (s, 6H), 2.54 (m, J=14.5, 9.5, 7.3 Hz, 1H), 2.31 (s, 3H), 2.17 (s, 3H), 1.92 (ddd, J=14.2, 8.1, 2.6 Hz, 1H), 1.81 (s, 3H), 1.24 (s, 3H), 1.14 (s, 3H).

$^{13}C$ NMR (101 MHz, $CDCl_3$) δ 205.73, 171.28, 170.21, 164.84, 155.01, 152.98, 141.50, 134.17, 133.99, 129.83, 128.91, 128.14, 88.54, 84.21, 83.86, 82.88, 80.06, 75.99, 72.28, 71.79, 69.45, 57.11, 57.00, 46.25, 41.32, 36.53, 35.89, 33.73, 25.62, 22.21, 21.33, 14.91, 10.85.

Example 12 Preparation of PCMI-12

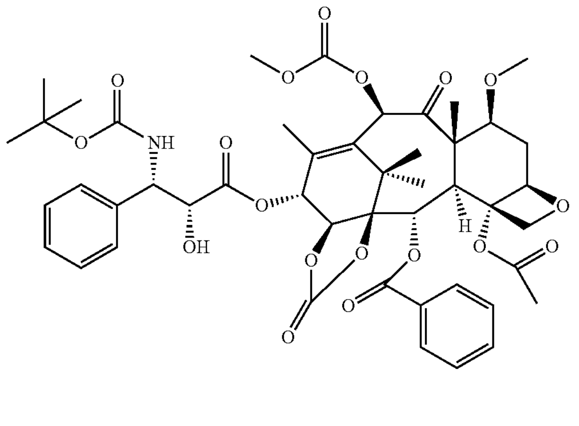

1) Preparation of (4S,5R)-3-t-butyloxycarbonyl-2-(4-methoxyphenyl)-4-phenyl-5-oxazolidine carboxylic acid The specific method was seen in Step 1) in Example 1.

2) Preparation of 10-methoxyl formyl-7-methoxyl-1,14-carbonate baccatin III

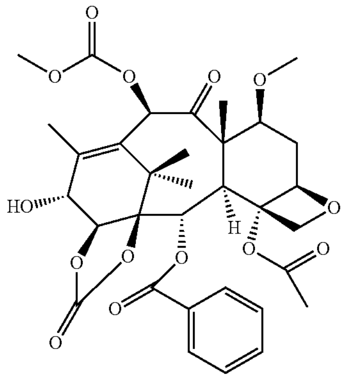

10-DAB (1 eq.) was used as raw material, dissolved in DMF and added successively with 2.5 equivalents of imidazole and 2.5 equivalents of triethyl chlorosilane. By post-treatment, the crude compound 7 was given.

The compound 7 (1 eq.) was dissolved in dry THF which was used as the solvent, into which 1.5 equivalents LHMDS was added at 0° C. After 1 hour of reaction, 2 equivalents of methoxyl formyl chloride was slowly added dropwise to the reaction liquid and reacted for 2 hours. By post-treatment of purification by column chromatography, the compound 29 was given in a yield of 62%.

The compound 29 (1 eq.) was dissolved in acetone solution, into which 10 equivalents of manganese dioxide was added at room temperature to react for 4 hours. By post-treatment of purification by column chromatography, the compound 30 was given in a yield of 75%.

The compound 30 (1 eq.) was dissolved in dry THF, into which 1.5 equivalents of tetrabutylammonium fluoride (which is in the form of a solution in THF) was added at room temperature. After 1 hour of reaction, the reaction was completed. By post-treatment of purification by column chromatography, the compound 31 was given in a yield of 90%.

The compound 31 was reacted with p-toluenesulfonyl chloride to give the compound 32.

The compound 32 (1 eq.) was dissolved in anhydrous tetrahydrofuran to react with methyl magnesium bromide (2 eq.) at room temperature for 3 hours under the protection of nitrogen. After post-treatment, the crude compound 33 was obtained after dried.

The compound 33 (1 eq.) was dissolved in dry THF/DMPU (4:1) solution, into which 1.2 equivalents of potassium t-butoxide was added at −70° C. to react for 20 min. The obtained reaction liquid was slowly added dropwise with 2 equivalents of N-(sulfonyl)oxaziridine to react for 2 hours. By post-treatment of purification by column chromatography, the compound 34 was given in a yield of 75%.

The compound 34 (1 eq.) was reacted with 2 equivalents of N,N'-carbonyldiimidazole (CDI) in dry tetrahydrofuran to give the compound 35 in a yield of 95%.

The compound 35 (1 eq.) was dissolved in dry tetrahydrofuran, into which 0.2 equivalents of (R)-2-methyl oxazaborodine was added at room temperature as a catalyst, followed by addition of 5 equivalents of borane/THF solution to react for 8 hours. After completion of reaction, by post-treatment of purification by column chromatography, the compound 36 of 10-methoxyl formyl-7-methoxy-1,14-carbonate baccatin III was obtained as the final product in a yield of 80%.

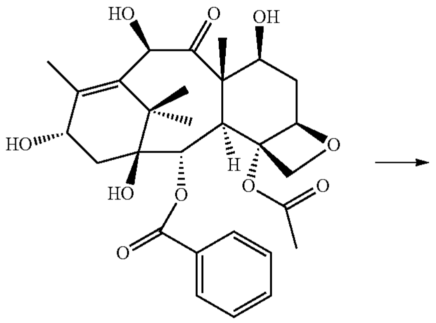

10-DAB

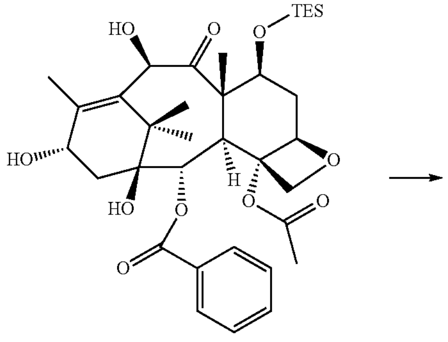

7

-continued
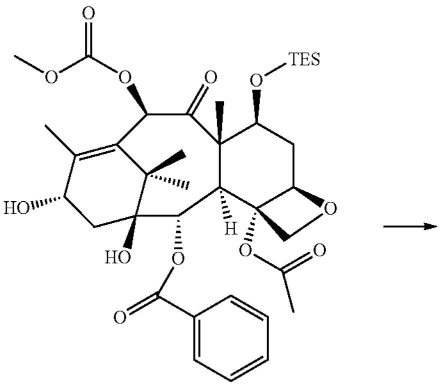
29
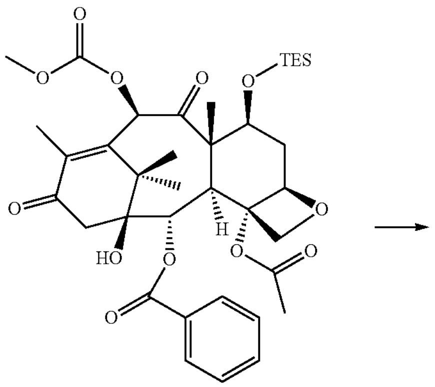
30
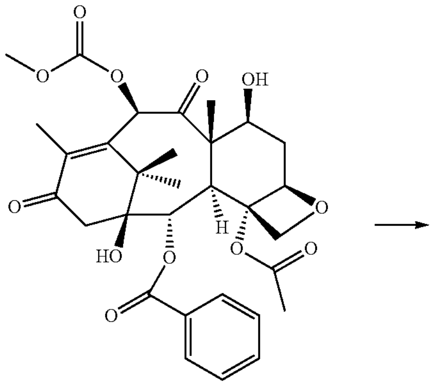
31
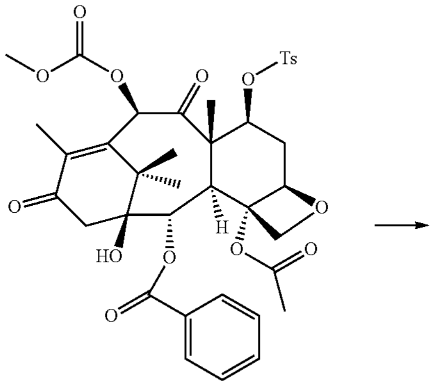
32
-continued
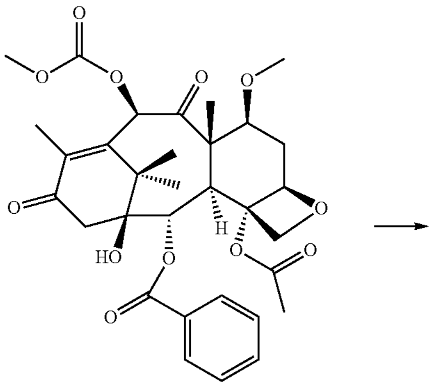
33
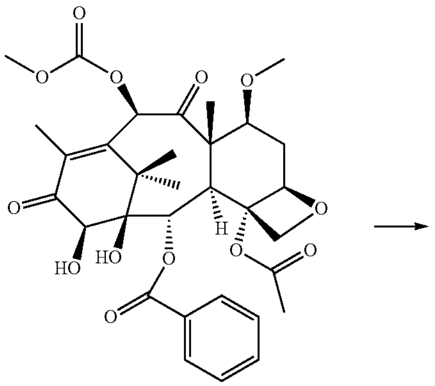
34
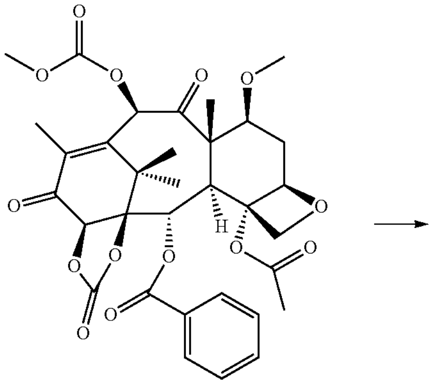
35
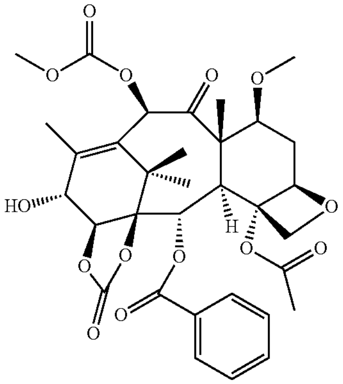
36

3) Preparation of PCMI-12

The specific method was seen in Step 3) in Example 1 and the purity of the final product was 95% or higher.

PCMI-12: mp: 231-232° C.;

MS (m/z) ESI: 944.4 $(M+Na)^+$;

$^1H$ NMR (400 MHz, $CDCl_3$) δ 8.02 (d, J=7.3 Hz, 2H), 7.61 (t, J=7.4 Hz, 1H), 7.48 (t, J=7.7 Hz, 2H), 7.45-7.30 (m, 5H), 6.44 (d, J=6.1 Hz, 1H, H-13), 6.15 (s, 1H, H-10), 6.09 (d, J=7.5 Hz, 1H, H-2), 5.47 (d, J=9.0 Hz, 1H, NH-3'), 5.33 (s, 1H, H-3'), 4.94 (d, J=7.9 Hz, 1H, H-5), 4.78 (d, J=6.7 Hz, 1H, H-14), 4.71 (s, 1H, H-2'), 4.28 (d, J=8.4 Hz, 1H, H-20), 4.21 (d, J=8.3 Hz, 1H, H-20), 3.92-3.80 (m, 4H, OH-2'), 3.70 (d, J=7.4 Hz, 1H, H-3), 3.35 (s, 3H), 2.72 (ddd, J=14.5, 9.8, 6.4 Hz, 1H, H-6), 2.44 (s, 3H), 1.94 (d, J=1.1 Hz, 3H), 1.86-1.73 (m, 4H, H-6), 1.40 (s, 9H), 1.32 (s, 6H).

$^{13}C$ NMR (101 MHz, $CDCl_3$) δ 200.44, 171.89, 170.88, 164.62, 154.60, 151.81, 138.29, 134.17, 133.84, 129.94, 129.03, 128.95, 128.23, 127.97, 126.65, 87.92, 83.94, 81.04, 80.72, 80.10, 79.56, 75.91, 74.74, 74.40, 69.00, 57.67, 57.38, 55.41, 46.62, 41.79, 32.06, 29.70, 28.25, 25.74, 22.62, 22.35, 14.71, 10.40.

Example 13 Preparation of PCMI-13

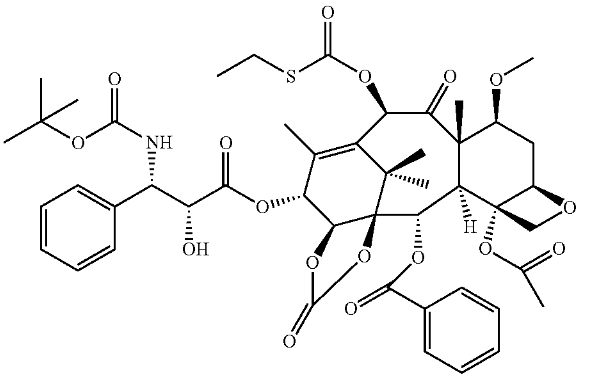

1) Preparation of (4S,5R)-3-t-butyloxycarbonyl-2-(4-methoxyphenyl)-4-phenyl-5-oxazolidine carboxylic acid The specific method was seen in Step 1) in Example 1.

2) Preparation of 10-ethylthioformyl-7-methoxyl-1,14-carbonate baccatin III

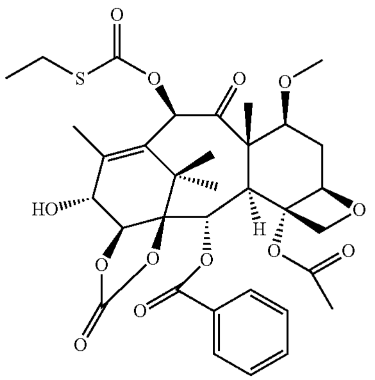

10-DAB (1 eq.) was used as raw material, dissolved in DMF and added successively with 2.5 equivalents of imidazole and 2.5 equivalents of triethyl chlorosilane. By post-treatment, the crude compound 7 was given.

The compound 7 (1 eq.) was dissolved in dry THF which was used as the solvent and firstly reacted with 2 equivalents of N,N'-carbonyldiimidazole at room temperature for 2 hours. Then the reaction liquid was added with 2 equivalents of ethanethiol. After 4 hours of reaction, by post-treatment of purification by column chromatography, the compound 37 was given in a yield of 72%.

The compound 37 (1 eq.) was dissolved in acetone solution, into which 10 equivalents of manganese dioxide was added at room temperature to react for 4 hours. By post-treatment of purification by column chromatography, the compound 38 was given in a yield of 86%.

The compound 38 (1 eq.) was dissolved in dry THF, into which 1.5 equivalents of tetrabutylammonium fluoride (which is in the form of a solution in THF) was added at room temperature. After 1 hour of reaction, the reaction was completed. By post-treatment of purification by column chromatography, the compound 39 was given in a yield of 90%.

The compound 39 was reacted with p-toluenesulfonyl chloride to give the compound 40.

The compound 40 (1 eq.) was dissolved in anhydrous tetrahydrofuran to react with methyl magnesium bromide (2 eq.) at room temperature for 3 hours under the protection of nitrogen. After post-treatment, the crude compound 41 was obtained after dried.

The compound 41 (1 eq.) was dissolved in dry THF/DMPU (4:1) solution, into which 1.2 equivalents of potassium t-butoxide was added at −70° C. to react for 20 min. The obtained reaction liquid was slowly added dropwise with 2 equivalents of N-(sulfonyl)oxaziridine to react for 2 hours. By post-treatment of purification by column chromatography, the compound 42 was given in a yield of 75%.

The compound 42 (1 eq.) was reacted with 2 equivalents of N,N'-carbonyldiimidazole (CDI) in dry tetrahydrofuran to give the compound 43 in a yield of 95%.

The compound 43 (1 eq.) was dissolved in dry tetrahydrofuran, into which 0.2 equivalents of (R)-2-methyl oxazaborodine was added at room temperature as a catalyst, followed by addition of 5 equivalents of borane/THF solution to react for 8 hours. After completion of reaction, by post-treatment of purification by column chromatography, the compound 44 of 10-ethylthioformyl-7-methoxy-1,14-carbonate baccatin III was obtained as the final product in a yield of 80%.

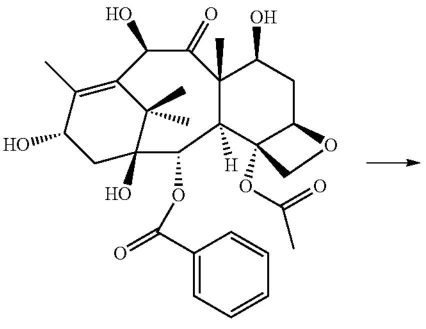

10-DAB

-continued
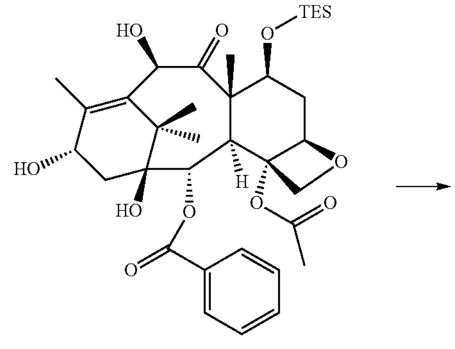
7
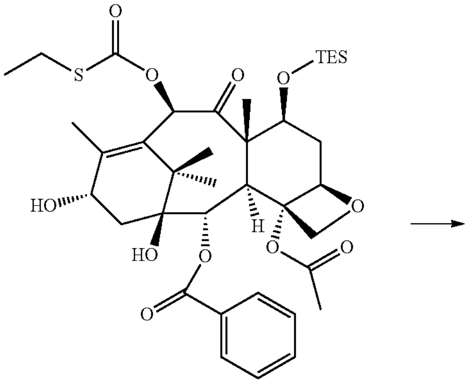
37
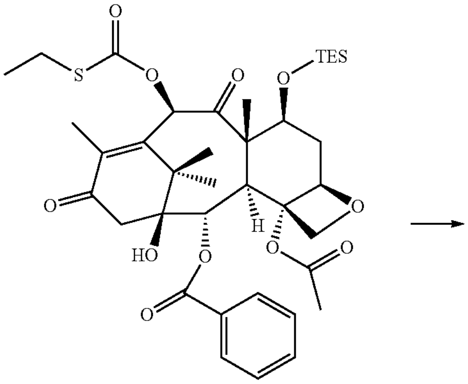
38
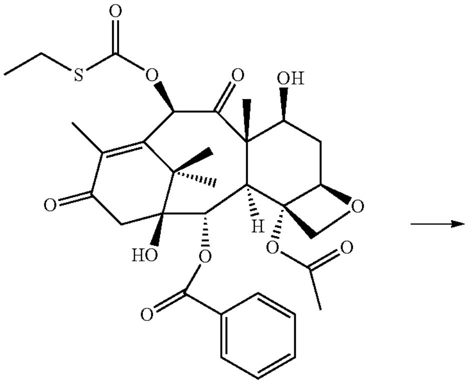
39
-continued
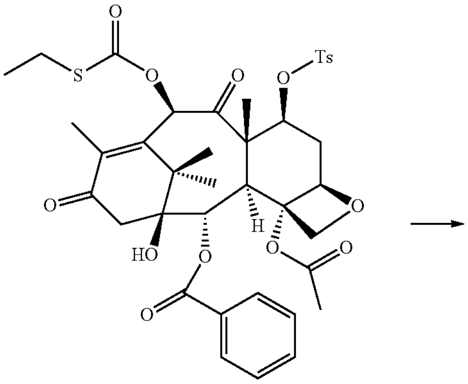
40
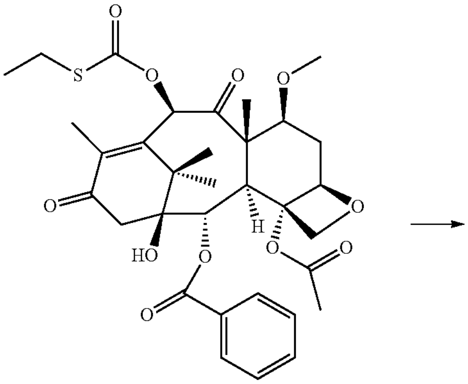
41
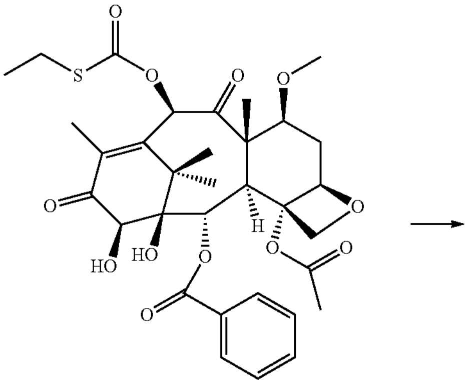
42
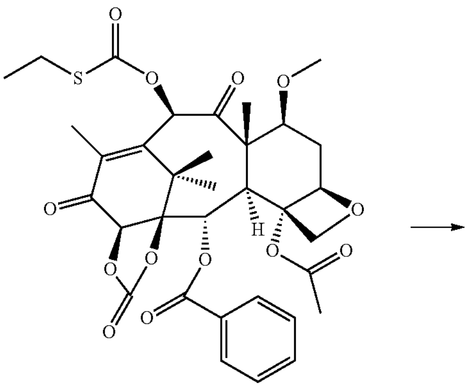
43

-continued

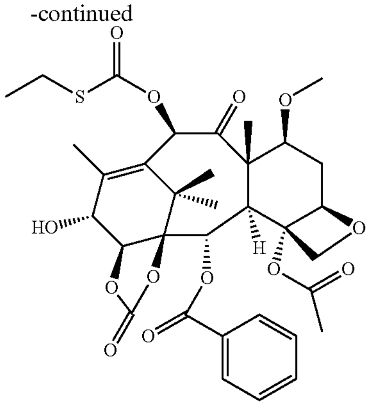

44

3) Preparation of PCMI-13

The specific method was seen in Step 3) in Example 1 and the purity of the final product was 95% or higher.

PCMI-13: mp: 215-216° C.;

MS (m/z) ESI: 974.4 $(M+Na)^+$;

$^1$H NMR (400 MHz, MeOD) δ 8.14 (d, J=7.6 Hz, 2H), 7.69 (t, J=7.4 Hz, 1H), 7.58 (t, J=7.7 Hz, 2H), 7.44-7.36 (m, 4H), 7.34-7.27 (m, 1H), 6.39 (d, J=10.7 Hz, 1H), 6.15 (t, J=8.9 Hz, 1H), 5.87 (d, J=6.3 Hz, 1H), 5.23 (d, J=10.7 Hz, 1H), 5.15 (s, 1H), 4.99 (d, J=9.0 Hz, 1H), 4.89 (m, 1H), 4.56 (d, J=2.3 Hz, 1H), 4.25 (d, J=8.3 Hz, 1H), 4.19 (d, J=8.3 Hz, 1H), 3.33 (s, 1H), 3.24 (d, J=6.1 Hz, 1H), 2.77-2.62 (m, 1H), 2.34 (s, 3H), 2.22 (t, J=9.2 Hz, 2H), 2.14 (s, 3H), 1.99-1.88 (m, 4H), 1.78 (s, 3H), 1.66 (s, 3H), 1.39 (s, 9H), 1.27 (s, 3H).

$^{13}$C NMR (101 MHz, MeOD) δ 173.20, 171.57, 170.61, 170.09, 166.07, 156.40, 146.86, 141.17, 139.00, 133.34, 129.90, 129.68, 128.29, 127.40, 126.90, 84.25, 83.21, 80.84, 79.21, 79.01, 77.19, 75.68, 73.67, 73.54, 71.10, 70.96, 60.15, 56.99, 45.14, 42.88, 38.23, 34.89, 33.87, 33.37, 27.33, 26.98, 25.37, 24.68, 22.31, 21.85, 19.53, 13.59, 13.12, 12.31.

Example 14 Preparation of PCMI-14

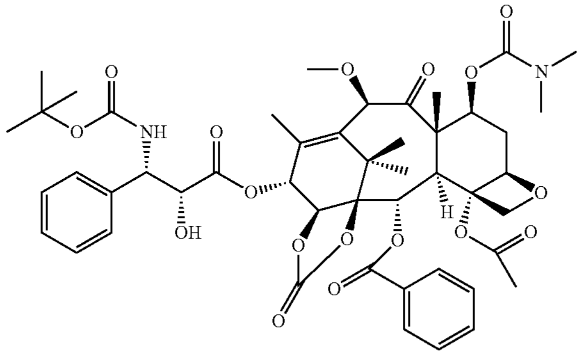

1) Preparation of (4S,5R)-3-t-butyloxycarbonyl-2-(4-methoxyphenyl)-4-phenyl-5-oxazolidine carboxylic acid The specific method was seen in Step 1) in Example 1.

2) Preparation of 7-dimethylcarbamoyl-10-methoxyl-1,14-carbonate baccatin III

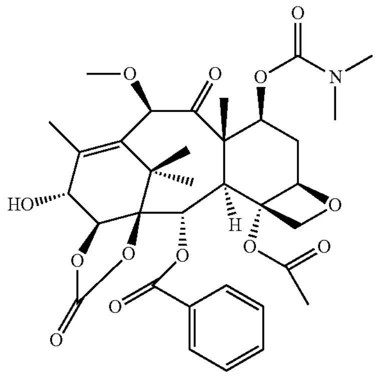

10-DAB (1 eq.) was used as raw material, dissolved in DMF and added successively with 2.5 equivalents of imidazole and 2.5 equivalents of triethyl chlorosilane. By post-treatment, the crude compound 7 was given.

The compound 7 was dissolved in dichloromethane which was used as the solvent, into which 2 equivalents of pyridine was added at 0° C. Successively, the reaction liquid was added dropwise with 2 equivalents of p-toluenesulfonyl chloride. After 4 hours of reaction, by post-treatment of purification by column chromatography, the compound 8 was given in a yield of 85-90%.

The compound 8 (1 eq.) was dissolved in anhydrous tetrahydrofuran to react with methyl magnesium bromide (2 eq.) at room temperature for 3 hours under the protection of nitrogen. After post-treatment, the crude compound 9 was obtained after dried.

The compound 9 (1 eq.) was dissolved in acetone solution, into which 10 equivalents of manganese dioxide was added at room temperature to react for 4 hours. By post-treatment of purification by column chromatography, the compound 10 was given in a yield of 75%.

The compound 10 (1 eq.) was dissolved in dry THF, into which 1.5 equivalents of tetrabutylammonium fluoride (which is in the form of a solution in THF) was added at room temperature. After 1 hour of reaction, the reaction was completed. By post-treatment of purification by column chromatography, the compound 45 was given in a yield of 90%.

The compound 45 (1 eq.) was dissolved in dry THF which was used as the solvent, into which 1.5 equivalents LHMDS was added at 0° C. After 1 hour of reaction, 2 equivalents of dimethylcarbamoyl chloride was slowly added dropwise to the reaction liquid and reacted for 2 hours. By post-treatment of purification by column chromatography, the compound 46 was given in a yield of 87%.

The compound 46 (1 eq.) was dissolved in dry THF/DMPU (4:1) solution, into which 1.2 equivalents of potassium t-butoxide was added at −70° C. to react for 20 min. The obtained reaction liquid was slowly added dropwise with 2 equivalents of N-(sulfonyl)oxaziridine to react for 2 hours. By post-treatment of purification by column chromatography, the compound 47 was given in a yield of 75%.

The compound 47 (1 eq.) was reacted with 2 equivalents of N,N'-carbonyldiimidazole (CDI) in dry tetrahydrofuran to give the compound 48 in a yield of 95%.

The compound 48 (1 eq.) was dissolved in dry tetrahydrofuran, into which 0.2 equivalents of (R)-2-methyl oxazaborodine was added at room temperature as a catalyst, followed by addition of 5 equivalents of borane/THF solution to react for 8 hours. After completion of reaction, by post-treatment of purification by column chromatography, the compound 49 of 7-dimethylcarbamoyl-10-methoxyl-1,14-carbonate baccatin III was obtained as the final product in a yield of 80%.

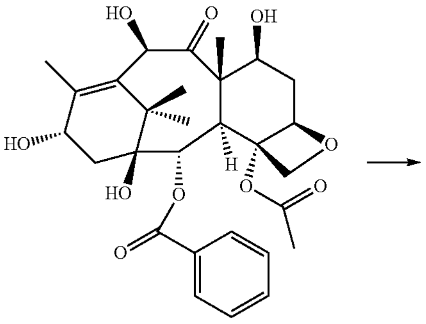

10-DAB

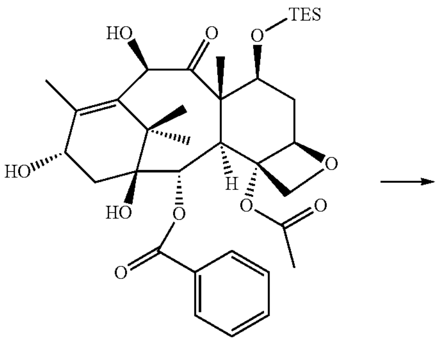

7

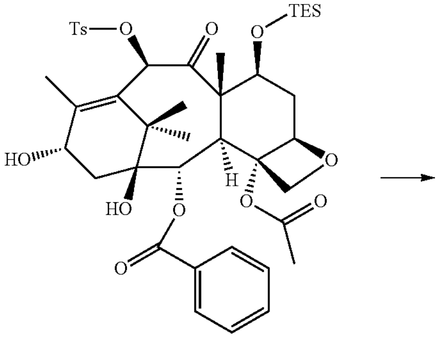

8

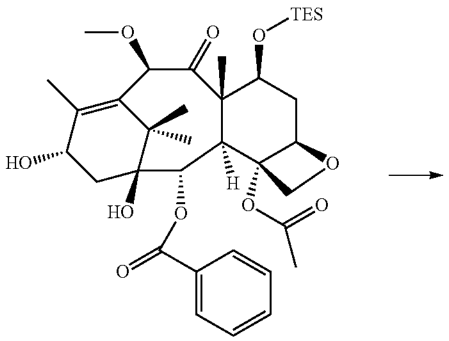

9

-continued

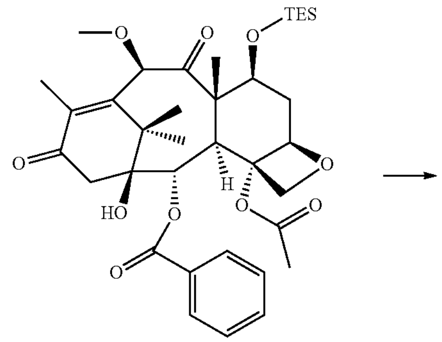

10

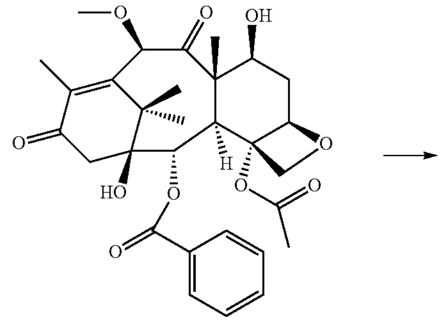

45

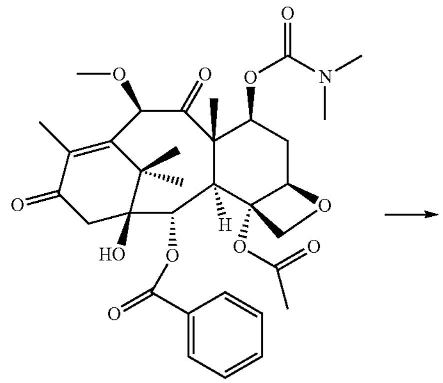

46

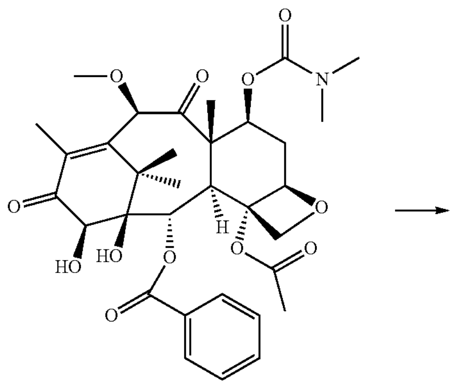

47

-continued

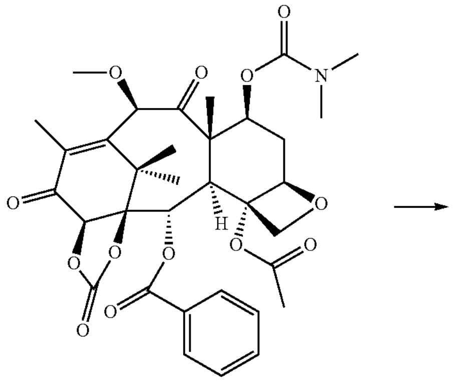

48

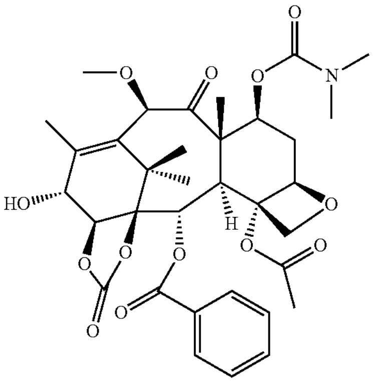

49

3) Preparation of PCMI-14

The specific method was seen in Step 3) in Example 1 and the purity of the final product was 95% or higher.

PCMI-14: mp: 236-237° C.;

MS (m/z) ESI: 957.3 $(M+Na)^+$;

$^1$H NMR (400 MHz, $CDCl_3$) δ 8.05 (d, J=7.3 Hz, 2H), 7.63 (t, J=7.4 Hz, 1H), 7.51 (t, J=7.7 Hz, 2H), 7.47-7.31 (m, 5H), 6.48 (d, J=6.1 Hz, 1H, H-13), 6.12 (d, J=7.4 Hz, 1H, H-2), 5.54 (d, J=9.1 Hz, 1H, NH-3'), 5.46 (dd, J=10.7, 7.2 Hz, 1H, H-7), 5.38 (s, 1H, H-3'), 5.23 (s, 1H, H-10), 4.93 (d, J=8.0 Hz, 1H, H-5), 4.82 (d, J=6.8 Hz, 1H, H-14), 4.73 (d, J=4.1 Hz, 1H, H-2'), 4.31 (d, J=8.4 Hz, 1H, H-20), 4.26 (d, J=8.5 Hz, 1H, H-20), 3.85 (d, J=7.4 Hz, 1H, H-3), 3.68 (s, 1H, OH-2'), 3.40 (s, 3H), 2.88 (s, 6H), 2.59-2.49 (m, 1H, H-6), 2.00-1.94 (m, 4H, H-6), 1.84 (s, 3H), 1.40 (s, 9H), 1.30 (d, J=3.2 Hz, 6H).

$^{13}$C NMR (101 MHz, $CDCl_3$) δ 205.07, 172.08, 170.45, 164.78, 154.96, 151.98, 136.29, 135.82, 134.15, 129.96, 128.97, 128.12, 128.02, 126.64, 88.12, 83.89, 82.34, 80.59, 80.41, 79.67, 76.06, 74.87, 74.27, 71.99, 69.33, 57.30, 57.07, 45.85, 41.72, 36.57, 35.89, 33.90, 33.76, 29.70, 28.25, 25.60, 25.55, 24.94, 22.56, 22.04, 14.38, 10.91.

Example 15 Preparation of PCMI-15

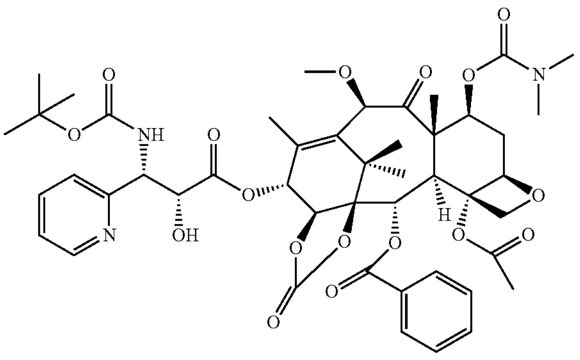

1) Preparation of (4S,5R)-3-t-butyloxycarbonyl-2-(4-methoxyphenyl)-4-(2-pyridyl)-5-oxazolidine carboxylic acid The specific method was seen in Step 1) in Example 4.

2) Preparation of 7-dimethylcarbamoyl-10-methoxyl-1,14-carbonate baccatin III The specific method was seen in Step 2) in Example 14.

3) Preparation of PCMI-15

The specific method was seen in Step 3) in Example 1 and the purity of the final product was 95% or higher.

PCMI-15: mp: 231-232° C.;

MS (m/z) ESI: 958.3 $(M+Na)^+$;

$^1$H NMR (400 MHz, $CDCl_3$) δ 8.50 (d, J=4.6 Hz, 1H), 8.10-8.01 (m, 2H), 7.80 (td, J=7.8, 1.6 Hz, 1H), 7.65 (t, J=7.4 Hz, 1H), 7.51 (dd, J=16.2, 8.2 Hz, 3H), 7.30 (d, J=9.9 Hz, 1H), 6.40 (d, J=6.2 Hz, 1H), 6.13 (d, J=7.4 Hz, 1H), 5.85 (d, J=10.0 Hz, 1H), 5.55-5.42 (m, 2H, H-7), 5.24 (s, 1H), 4.98 (d, J=8.2 Hz, 1H), 4.88 (d, J=6.9 Hz, 1H), 4.80 (s, 1H), 4.34 (d, J=8.3 Hz, 1H), 4.26 (d, J=8.4 Hz, 1H), 3.87 (d, J=7.5 Hz, 1H), 3.38 (s, 3H), 2.88 (t, J=3.5 Hz, 6H), 2.61-2.51 (m, 4H), 2.01-1.91 (m, 4H), 1.85 (s, 3H), 1.51 (s, 9H), 1.27 (s, 3H), 1.25 (s, 3H).

$^{13}$C NMR (101 MHz, $CDCl_3$) δ 205.25, 172.80, 170.69, 164.80, 159.45, 154.99, 152.14, 148.17, 137.90, 136.87, 135.58, 134.23, 129.89, 128.97, 128.02, 123.07, 122.09, 88.33, 83.89, 82.38, 80.49, 80.10, 80.00, 76.01, 74.20, 72.05, 69.52, 57.24, 57.09, 55.40, 45.87, 41.64, 36.57, 35.92, 33.79, 31.93, 29.70, 28.34, 25.47, 22.70, 22.00, 21.93, 14.36, 14.13, 10.89.

Example 16 Preparation of PCMI-16

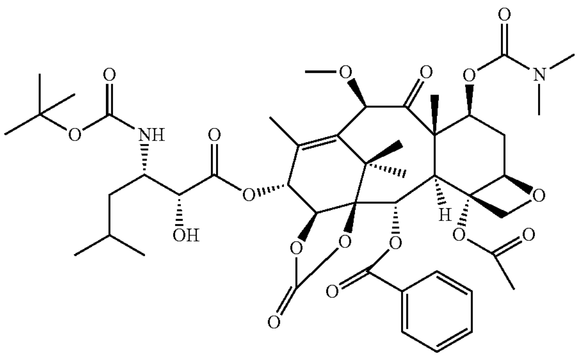

1) Preparation of (4S,5R)-3-t-butyloxycarbonyl-2-(4-methoxyphenyl)-4-isobutyl-5-oxazolidine carboxylic acid The specific method was seen in Step 1) in Example 5.

2) Preparation of 7-dimethylcarbamoyl-10-methoxyl-1,14-carbonate baccatin III

The specific method was seen in Step 2) in Example 14.

3) Preparation of PCMI-16

The specific method was seen in Step 3) in Example 1 and the purity of the final product was 95% or higher.

PCMI-16: mp: 227-228° C.;

MS (m/z) ESI: 937.2 $(M+Na)^+$;

$^1H$ NMR (400 MHz, $CDCl_3$) δ 8.06 (d, J=7.6 Hz, 2H), 7.63 (t, J=7.4 Hz, 1H), 7.50 (t, J=7.7 Hz, 2H), 6.48 (d, J=6.3 Hz, 1H), 6.13 (d, J=7.4 Hz, 1H), 5.48 (dd, J=10.6, 7.2 Hz, 1H), 5.25 (s, 1H), 4.95 (d, J=8.3 Hz, 1H), 4.89 (d, J=6.9 Hz, 1H), 4.77 (d, J=9.0 Hz, 1H), 4.33 (dd, J=8.9, 5.8 Hz, 2H), 4.27 (d, J=8.4 Hz, 1H), 4.22-4.09 (m, 1H), 3.93-3.83 (m, 2H, H-3), 3.41 (s, 3H), 2.88 (s, 6H), 2.60-2.41 (m, 4H), 2.02 (s, 3H), 1.96 (dd, J=19.7, 7.7 Hz, 1H), 1.85 (s, 3H), 1.75-1.69 (m, 1H), 1.52-1.37 (m, 11H), 1.30 (s, 3H), 1.27 (s, 3H), 1.01 (t, J=6.3 Hz, 6H).

$^{13}C$ NMR (101 MHz, $CDCl_3$) δ 205.08, 172.96, 170.35, 164.81, 154.97, 152.01, 136.39, 134.05, 129.95, 128.94, 128.11, 88.19, 83.90, 82.39, 80.25, 79.67, 76.04, 74.74, 73.71, 71.99, 69.44, 57.29, 57.07, 54.34, 51.49, 45.88, 41.76, 40.57, 36.54, 35.86, 33.76, 29.67, 28.24), 25.57, 24.85, 23.24, 22.46, 22.08, 14.42, 10.90.

Example 17 Preparation of PCMI-17

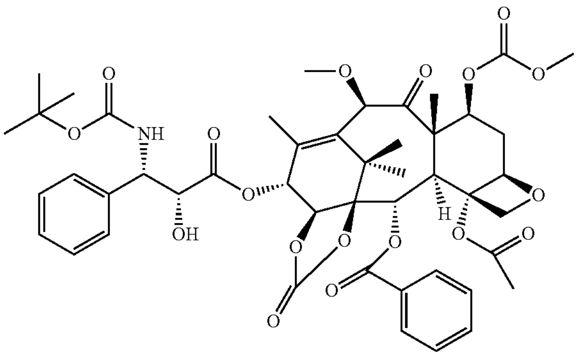

1) Preparation of (4S,5R)-3-t-butyloxycarbonyl-2-(4-methoxyphenyl)-4-phenyl-5-oxazolidine carboxylic acid The specific method was seen in Step 1) in Example 1.

2) Preparation of 7-methoxyformyl-10-methoxyl-1,14-carbonate baccatin III

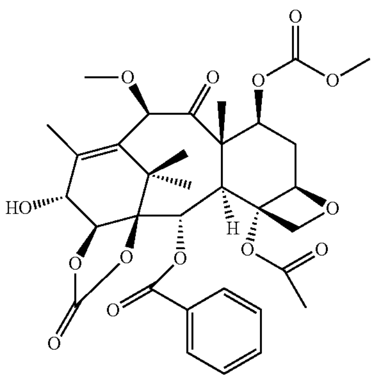

10-DAB (1 eq.) was used as raw material, dissolved in DMF and added successively with 2.5 equivalents of imidazole and 2.5 equivalents of triethyl chlorosilane. By post-treatment, the crude compound 7 was given.

The compound 7 was dissolved in dichloromethane which was used as the solvent, into which 2 equivalents of pyridine was added at 0° C. Successively, the reaction liquid was added dropwise with 2 equivalents of p-toluenesulfonyl chloride. After 4 hours of reaction, by post-treatment of purification by column chromatography, the compound 8 was given in a yield of 85-90%.

The compound 8 (1 eq.) was dissolved in anhydrous tetrahydrofuran to react with methyl magnesium bromide (2 eq.) at room temperature for 3 hours under the protection of nitrogen. After post-treatment, the crude compound 9 was obtained after dried.

The compound 9 (1 eq.) was dissolved in acetone solution, into which 10 equivalents of manganese dioxide was added at room temperature to react for 4 hours. By post-treatment of purification by column chromatography, the compound 10 was given in a yield of 75%.

The compound 10 (1 eq.) was dissolved in dry THF, into which 1.5 equivalents of tetrabutylammonium fluoride (which is in the form of a solution in THF) was added at room temperature. After 1 hour of reaction, the reaction was completed. By post-treatment of purification by column chromatography, the compound 45 was given in a yield of 90%.

The compound 45 (1 eq.) was dissolved in dry THF which was used as the solvent, into which 1.5 equivalents LHMDS was added at 0° C. After 1 hour of reaction, 2 equivalents of methoxyformyl chloride was slowly added dropwise to the reaction liquid and reacted for 2 hours. By post-treatment of purification by column chromatography, the compound 50 was given in a yield of 71%.

The compound 50 (1 eq.) was dissolved in dry THF/DMPU (4:1) solution, into which 1.2 equivalents of potassium t-butoxide was added at −70° C. to react for 20 min. The obtained reaction liquid was slowly added dropwise with 2 equivalents of N-(sulfonyl)oxaziridine to react for 2 hours. By post-treatment of purification by column chromatography, the compound 51 was given in a yield of 75%.

The compound 51 (1 eq.) was reacted with 2 equivalents of N,N'-carbonyldiimidazole (CDI) in dry tetrahydrofuran to give the compound 52 in a yield of 95%.

The compound 52 (1 eq.) was dissolved in dry tetrahydrofuran, into which 0.2 equivalents of (R)-2-methyl oxazaborodine was added at room temperature as a catalyst, followed by addition of 5 equivalents of borane/THF solution to react for 8 hours. After completion of reaction, by post-treatment of purification by column chromatography, the compound 53 of 7-methoxyformyl-10-methoxyl-1,14-carbonate baccatin III was obtained as the final product in a yield of 80%.

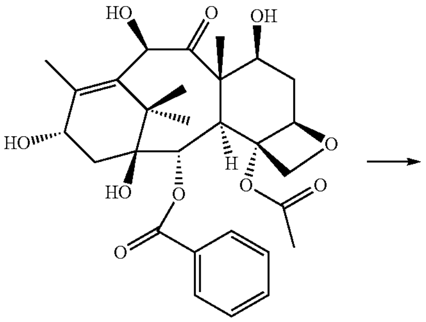

10-DAB

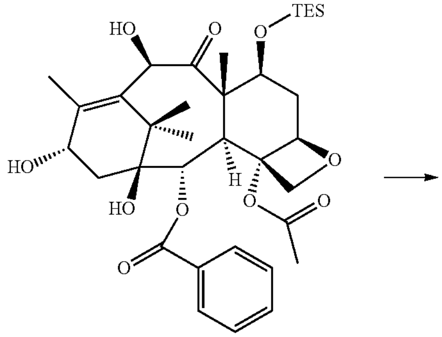

7

-continued

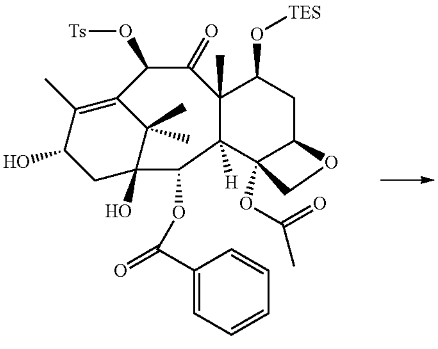

8

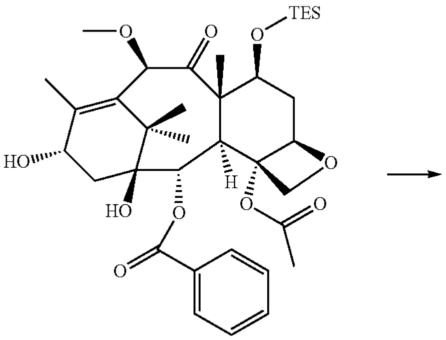

9

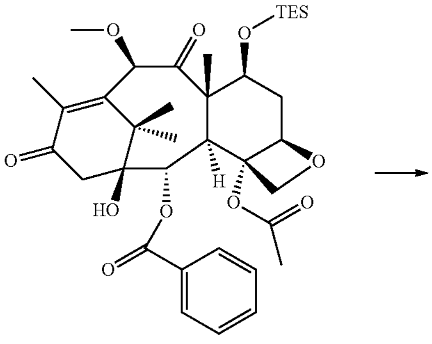

10

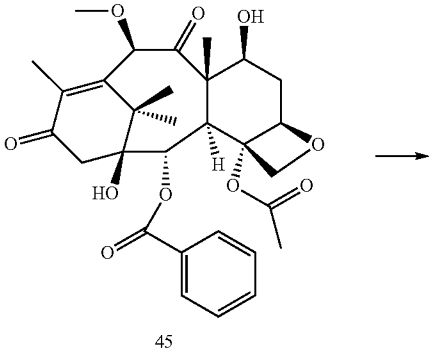

45

-continued

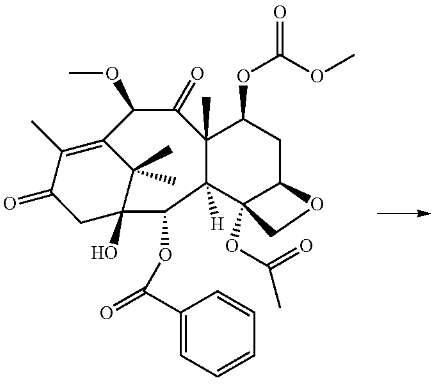

50

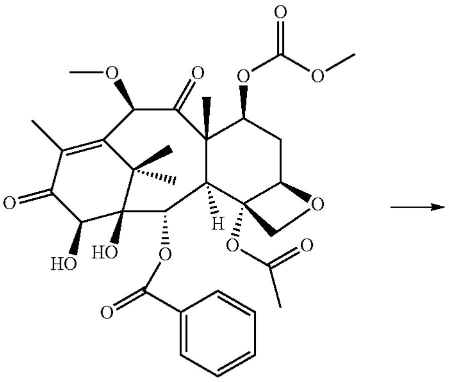

51

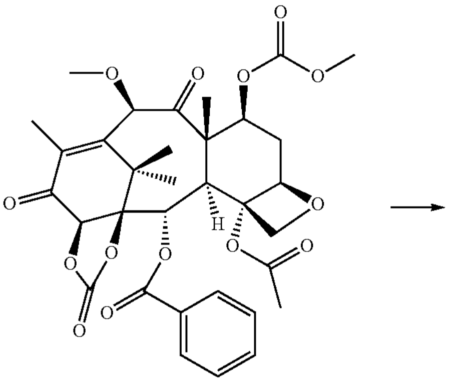

52

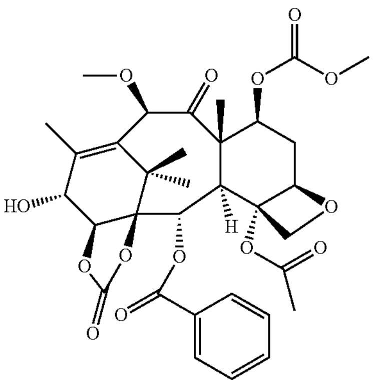

53

3) Preparation of PCMI-17

The specific method was seen in Step 3) in Example 1 and the purity of the final product was 95% or higher.

PCMI-17: mp: 233-234° C.;

MS (m/z) ESI: 944.4 $(M+Na)^+$;

IR: 3411, 2979, 2933, 1820, 1731, 1712, 1490, 1367, 1259, 1163, 1085, 713.

$^1H$ NMR (400 MHz, $CDCl_3$) δ 8.03 (d, J=7.4 Hz, 2H), 7.62 (t, J=7.4 Hz, 1H), 7.49 (t, J=7.7 Hz, 2H), 7.45-7.37 (m, 4H), 7.37-7.30 (m, 1H), 6.46 (d, J=6.1 Hz, 1H), 6.12 (d, J=7.4 Hz, 1H), 5.58 (d, J=8.6 Hz, 1H), 5.35 (dd, J=10.6, 7.2 Hz, 2H), 5.14 (s, 1H), 4.95-4.86 (m, 1H), 4.80 (d, J=6.8 Hz, 1H), 4.71 (s, 1H), 4.30 (d, J=8.4 Hz, 1H), 4.23 (d, J=8.5 Hz, 1H), 3.89-3.78 (m, 2H), 3.75 (s, 3H), 3.41 (s, 3H), 2.56 (ddd, J=14.6, 9.5, 7.3 Hz, 1H), 2.46 (s, 3H), 2.08-1.98 (m, 1H), 1.95 (d, J=1.1 Hz, 3H), 1.83 (s, 3H), 1.39 (s, 9H), 1.29 (s, 3H), 1.28 (s, 3H).

$^{13}C$ NMR (101 MHz, $CDCl_3$) δ 204.25, 172.06, 171.24, 170.73, 164.70, 155.73, 155.00, 151.92, 136.31, 135.79, 134.19, 129.95, 128.98, 128.94, 128.10, 127.93, 126.63, 88.09, 83.49, 82.19, 80.58, 80.25, 79.61, 76.01, 75.28, 74.71, 74.36, 69.24, 57.45, 56.89, 55.31, 49.22, 45.77, 41.63, 33.83, 33.25, 29.68, 28.24, 25.57, 25.51, 24.90, 22.48, 22.10, 14.33, 10.78.

Example 18 Preparation of PCMI-18

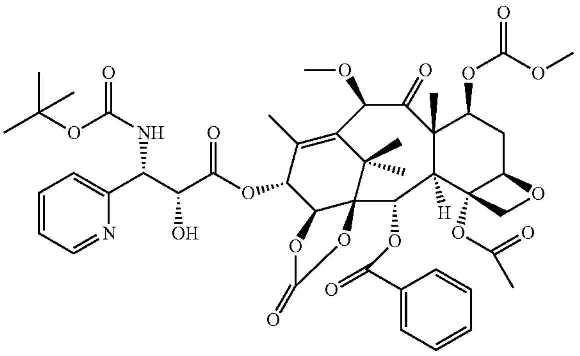

1) Preparation of (4S,5R)-3-t-butyloxycarbonyl-2-(4-methoxyphenyl)-4-(2-pyridyl)-5-oxazolidine carboxylic acid The specific method was seen in Step 1) in Example 4.

2) Preparation of 7-methoxyformyl-10-methoxyl-1,14-carbonate baccatin III

The specific method was seen in Step 2) in Example 17.

3) Preparation of PCMI-18

The specific method was seen in Step 3) in Example 1 and the purity of the final product was 95% or higher.

PCMI-18: mp: 235-236° C.;

MS (m/z) ESI: 923.4 $(M+H)^+$;

$^1H$ NMR (400 MHz, $CDCl_3$) δ 8.50 (d, J=4.6 Hz, 1H), 8.10-8.01 (m, 2H), 7.80 (td, J=7.8, 1.6 Hz, 1H), 7.65 (t, J=7.4 Hz, 1H), 7.51 (dd, J=16.2, 8.2 Hz, 3H), 7.30 (d, J=9.9

Hz, 1H), 6.46 (d, J=6.1 Hz, 1H), 6.12 (d, J=7.4 Hz, 1H), 5.58 (d, J=8.6 Hz, 1H), 5.35 (dd, J=10.6, 7.2 Hz, 2H), 5.14 (s, 1H), 4.95-4.86 (m, 1H), 4.80 (d, J=6.8 Hz, 1H), 4.71 (s, 1H), 4.30 (d, J=8.4 Hz, 1H), 4.23 (d, J=8.5 Hz, 1H), 3.89-3.78 (m, 2H, H-3), 3.75 (s, 3H), 3.41 (s, 3H), 2.56 (ddd, J=14.6, 9.5, 7.3 Hz, 1H), 2.46 (s, 3H), 2.08-1.98 (m, 1H), 1.95 (d, J=1.1 Hz, 3H), 1.83 (s, 3H), 1.39 (s, 9H), 1.29 (s, 3H), 1.28 (s, 3H).

$^{13}C$ NMR (101 MHz, $CDCl_3$) δ 205.25, 172.80, 170.69, 164.80, 159.45, 154.99, 152.14, 148.17, 137.90, 136.87, 135.58, 134.23, 129.89, 128.97, 128.02, 123.07, 122.09, 88.09, 83.49, 82.19, 80.58, 80.25, 79.61, 76.01, 75.28, 74.71, 74.36, 69.24, 57.45, 56.89, 55.31, 49.22, 45.77, 41.63, 33.83, 33.25, 29.68, 28.24, 25.57, 25.51, 24.90, 22.48, 22.10, 14.33, 10.78.

Example 19 Preparation of PCMI-19

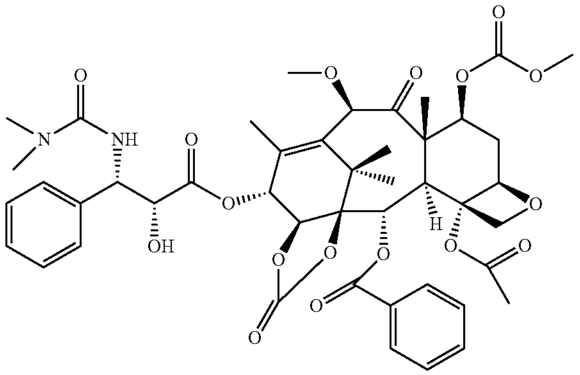

1) Preparation of (4S,5R)-3-dimethylcarbamoyl-2-(4-methoxyphenyl)-4-phenyl-5-oxazolidine carboxylic acid The specific method was seen in Step 1) in Example 3.

2) Preparation of 7-methoxyformyl-10-methoxyl-1,14-carbonate baccatin III

The specific method was seen in Step 2) in Example 17.

3) Preparation of PCMI-19

The specific method was seen in Step 3) in Example 1 and the purity of the final product was 95% or higher.

PCMI-19: mp: 213-214° C.;

MS (m/z) ESI: 894.3 $(M+H)^+$;

$^1H$ NMR (400 MHz, $CDCl_3$) δ 8.04 (d, J=7.5 Hz, 2H), 7.62 (t, J=7.4 Hz, 1H), 7.49 (t, J=7.7 Hz, 2H), 6.47 (d, J=6.1 Hz, 1H), 6.27 (s, 1H), 6.11 (d, J=7.5 Hz, 1H), 4.94 (d, J=7.9 Hz, 1H), 4.87 (d, J=6.9 Hz, 1H), 4.75 (d, J=8.9 Hz, 1H), 4.39 (dd, J=10.0, 5.2 Hz, 1H), 4.36-4.31 (m, 1H), 4.30 (d, J=8.6 Hz, 1H), 4.24 (d, J=8.4 Hz, 1H), 4.14-4.06 (m, 1H), 4.00 (d, J=6.0 Hz, 1H), 3.71 (d, J=7.4 Hz, 1H), 2.61-2.43 (m, 4H), 2.38 (d, J=3.7 Hz, 1H), 2.26 (s, 3H), 1.95-1.84 (m, 4H), 1.71 (d, J=12.4 Hz, 4H), 1.52-1.37 (m, 11H), 1.34 (s, 3H), 1.28 (s, 3H), 0.99 (t, J=6.8 Hz, 6H).

$^{13}C$ NMR (101 MHz, $CDCl_3$) δ 202.19, 172.97, 170.93, 170.65, 164.76, 156.27, 151.87, 139.79, 134.15, 133.52, 129.97, 129.00, 127.95, 88.19, 84.23, 80.46, 79.63, 75.94, 74.79, 74.59, 73.87, 71.73, 69.45, 58.71, 51.67, 45.05, 41.78, 40.42, 35.46, 29.70, 28.24, 25.98, 24.85, 23.23, 22.50, 22.15, 20.76, 15.01, 9.70.

Example 20 Preparation of PCMI-20

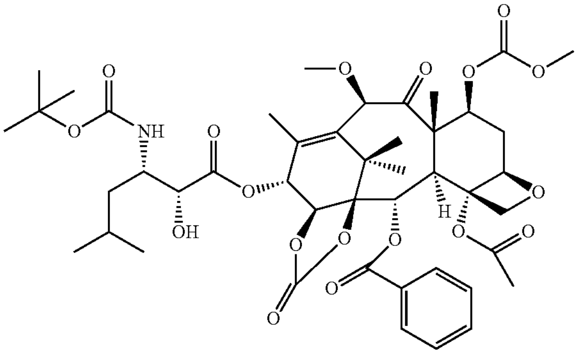

1) Preparation of (4S,5R)-3-t-butyloxycarbonyl-2-(4-methoxyphenyl)-4-isobutyl-5-oxazolidine carboxylic acid The specific method was seen in Step 1) in Example 5.

2) Preparation of 7-methoxyformyl-10-methoxyl-1,14-carbonate baccatin III

The specific method was seen in Step 2) in Example 17.

3) Preparation of PCMI-20

The specific method was seen in Step 3) in Example 1 and the purity of the final product was 95% or higher.

PCMI-20: mp: 229-230° C.;

MS (m/z) ESI: 924.4 $(M+Na)^+$;

$^1H$ NMR (400 MHz, $CDCl_3$) δ 8.04 (d, J=7.5 Hz, 2H), 7.62 (t, J=7.4 Hz, 1H), 7.49 (t, J=7.7 Hz, 2H), 6.47 (d, J=6.3 Hz, 1H), 6.13 (d, J=7.4 Hz, 1H), 5.36 (dd, J=10.6, 7.2 Hz, 1H), 5.15 (s, 1H), 4.93 (d, J=7.8 Hz, 1H), 4.88 (d, J=6.9 Hz, 1H), 4.80 (d, J=9.3 Hz, 1H), 4.39-4.28 (m, 2H), 4.25 (d, J=8.5 Hz, 1H), 4.13 (m, 1H), 4.01 (d, J=5.4 Hz, 1H), 3.84 (d, J=7.3 Hz, 1H), 3.75 (s, 3H), 3.41 (s, 3H), 2.62-2.47 (m, 4H), 2.10-2.03 (m, 1H), 1.99 (d, J=1.1 Hz, 3H), 1.83 (s, 3H), 1.71 (dd, J=11.2, 4.6 Hz, 1H), 1.44 (dd, J=10.1, 3.6 Hz, 2H), 1.41 (d, J=14.4 Hz, 9H), 1.30 (s, 3H), 1.29 (s, 3H), 0.99 (t, J=6.4 Hz, 6H).

$^{13}C$ NMR (101 MHz, $CDCl_3$) δ 204.27, 172.97, 171.21, 170.71, 164.75, 156.21, 155.00, 151.99, 136.46, 134.15, 129.96, 128.99, 127.95, 88.18, 83.51, 82.20, 80.34, 80.19, 79.63, 76.73, 76.01, 75.27, 74.61, 73.82, 69.29, 57.43, 56.89, 55.30, 51.61, 45.76, 41.66, 40.44, 33.25, 29.69, 28.24, 25.51, 24.85, 23.25, 22.44, 22.16, 14.41, 10.81.

Example 21 Preparation of PCMI-21

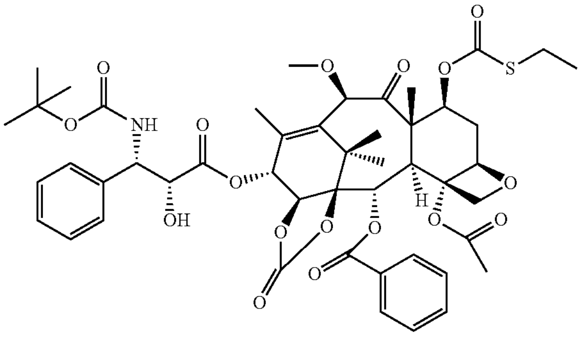

1) Preparation of (4S,5R)-3-t-butyloxycarbonyl-2-(4-methoxyphenyl)-4-phenyl-5-oxazolidine carboxylic acid The specific method was seen in Step 1) in Example 1.

2) Preparation of 7-ethylthioformyl-10-methoxy-1,14-carbonate baccatin III

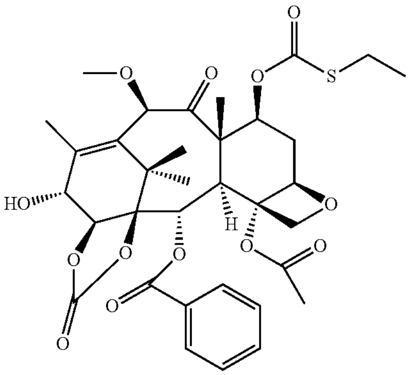

10-DAB (1 eq.) was used as raw material, dissolved in DMF and added successively with 2.5 equivalents of imidazole and 2.5 equivalents of triethyl chlorosilane. By post-treatment, the crude compound 7 was given.

The compound 7 was dissolved in dichloromethane which was used as the solvent, into which 2 equivalents of pyridine was added at 0° C. Successively, the reaction liquid was added dropwise with 2 equivalents of p-toluenesulfonyl chloride. After 4 hours of reaction, by post-treatment of purification by column chromatography, the compound 8 was given in a yield of 90%.

The compound 8 (1 eq.) was dissolved in anhydrous tetrahydrofuran to react with methyl magnesium bromide (2 eq.) at room temperature for 3 hours under the protection of nitrogen. After post-treatment, the crude compound 9 was obtained after dried.

The compound 9 (1 eq.) was dissolved in acetone solution, into which 10 equivalents of manganese dioxide was added at room temperature to react for 4 hours. By post-treatment of purification by column chromatography, the compound 10 was given in a yield of 75%.

The compound 10 (1 eq.) was dissolved in dry THF, into which 1.5 equivalents of tetrabutylammonium fluoride (which is in the form of a solution in THF) was added at room temperature. After 1 hour of reaction, the reaction was completed. By post-treatment of purification by column chromatography, the compound 45 was given in a yield of 90%.

The compound 45 (1 eq.) was dissolved in dry THF which was used as the solvent and firstly reacted with 2 equivalents of N,N'-carbonyldiimidazole at room temperature for 2 hours. Then the reaction liquid was added with 2 equivalents of ethanethiol. After 4 hours of reaction, by post-treatment of purification by column chromatography, the compound 54 was given in a yield of 78%.

The compound 54 (1 eq.) was dissolved in dry THF/DMPU (4:1) solution, into which 1.2 equivalents of potassium t-butoxide was added at −70° C. to react for 20 min. The obtained reaction liquid was slowly added dropwise with 2 equivalents of N-(sulfonyl)oxaziridine to react for 2 hours. By post-treatment of purification by column chromatography, the compound 55 was given in a yield of 75%.

The compound 55 (1 eq.) was reacted with 2 equivalents of N,N'-carbonyldiimidazole (CDI) in dry tetrahydrofuran to give the compound 56 in a yield of 95%.

The compound 56 (1 eq.) was dissolved in dry tetrahydrofuran, into which 0.2 equivalents of (R)-2-methyl oxazaborodine was added at room temperature as a catalyst, followed by addition of 5 equivalents of borane/THF solution to react for 8 hours. After completion of reaction, by post-treatment of purification by column chromatography, the compound 57 of 7-ethylthioformyl-10-methoxy-1,14-carbonate baccatin III was obtained as the final product in a yield of 80%.

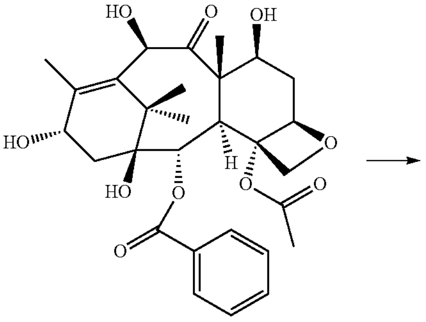

10-DAB

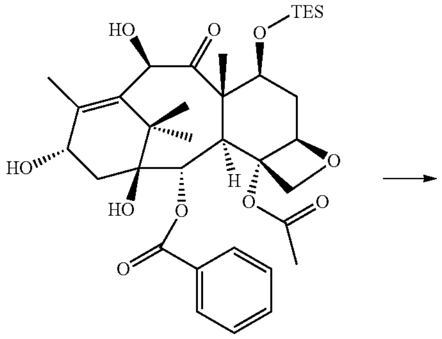

7

-continued
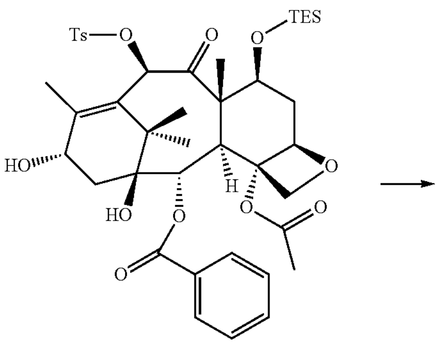
8
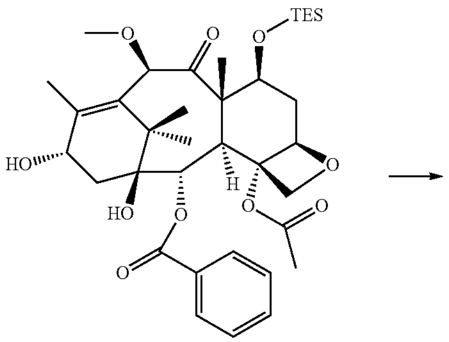
9
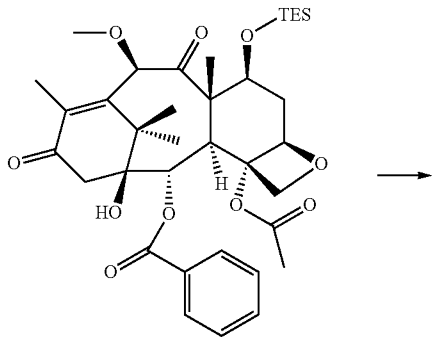
10
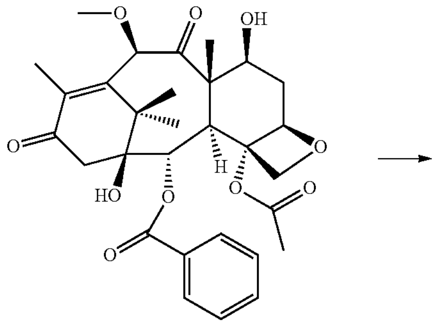
45
-continued
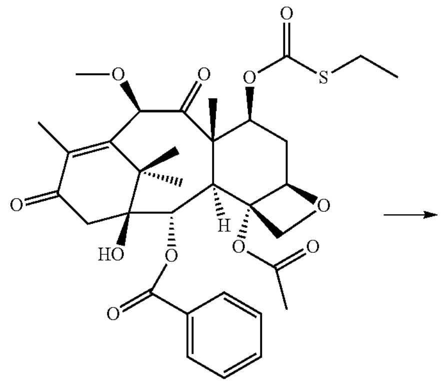
54
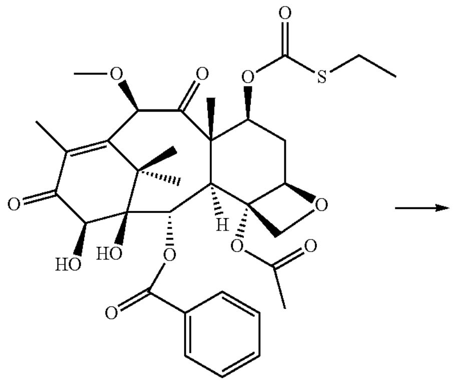
55
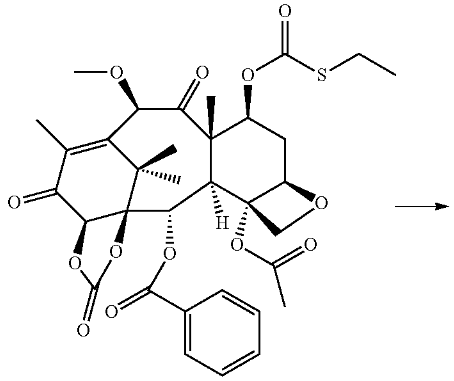
56
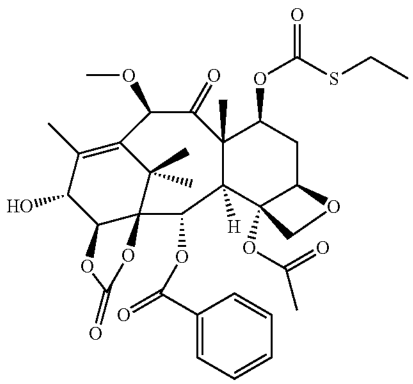
57

3) Preparation of PCMI-21

The specific method was seen in Step 3) in Example 1 and the purity of the final product was 95% or higher.

PCMI-21: mp: 238-239° C.;

MS (m/z) ESI: 974.4 $(M+Na)^+$;

$^1H$ NMR (400 MHz, $CDCl_3$) δ 8.03 (d, J=7.4 Hz, 2H), 7.62 (t, J=7.4 Hz, 1H), 7.49 (t, J=7.7 Hz, 2H), 7.45-7.37 (m, 4H), 7.37-7.30 (m, 1H), 6.46 (d, J=6.1 Hz, 1H), 6.12 (d, J=7.4 Hz, 1H), 5.58 (d, J=8.6 Hz, 1H), 5.35 (dd, J=10.6, 7.2 Hz, 2H), 5.14 (s, 1H), 4.95-4.86 (m, 1H), 4.80 (d, J=6.8 Hz, 1H), 4.71 (s, 1H), 4.30 (d, J=8.4 Hz, 1H), 4.23 (d, J=8.5 Hz, 1H), 3.89-3.78 (m, 2H), 3.75 (s, 3H), 3.41 (s, 3H), 2.56 (ddd, J=14.6, 9.5, 7.3 Hz, 1H), 2.46 (s, 3H), 2.08-1.98 (m, 1H), 1.95 (d, J=1.1 Hz, 3H), 1.83 (s, 3H), 1.39 (s, 9H), 1.29 (s, 3H), 1.28 (s, 3H).

$^{13}C$ NMR (101 MHz, $CDCl_3$) δ 204.25, 172.06, 171.24, 170.73, 164.70, 155.73, 155.00, 151.92, 136.31, 135.79, 134.19, 129.95, 128.98, 128.94, 128.10, 127.93, 126.63, 88.09, 83.49, 82.19, 80.58, 80.25, 79.61, 76.01, 75.28, 74.71, 74.36, 69.24, 57.45, 56.89, 55.31, 49.22, 45.77, 41.63, 33.83, 33.25, 29.68, 28.24, 25.57, 25.51, 24.90, 22.48, 22.10, 14.33, 10.78.

What is claimed is:

1. Taxanes compounds having the structure represented by general formula I:

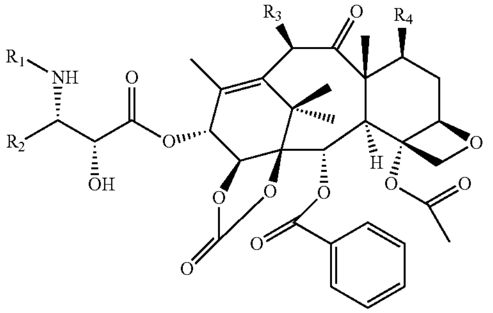

I wherein:

$R_1$ is benzoyl, t-butyloxycarbonyl, or N,N'-dimethylcarbamoyl;

$R_2$ is phenyl,

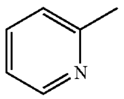
, or
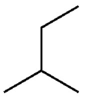
;

$R_3$ is —OMe, —$OCOOCH_3$, —$OCON(CH_3)_2$, or —$OCOSC_2H_5$;

$R_4$ is —OMe, —$OCOOCH_3$, —$OCON(CH_3)_2$, —$OCOSC_2H_5$, H, or OH

Provided that when $R_1$ is t-butyloxycarbonyl, then $R_2$ is not

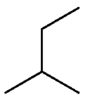

(isobutyl), $R_3$ is not —$OCON(CH_3)_2$, and $R_4$ is not OH.

2. The taxanes compounds according to claim 1, wherein the compounds are selected from the compound having the following structure:

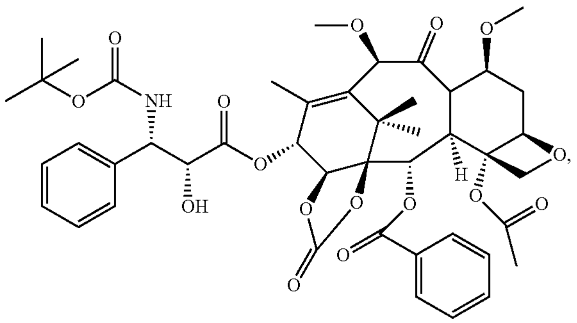

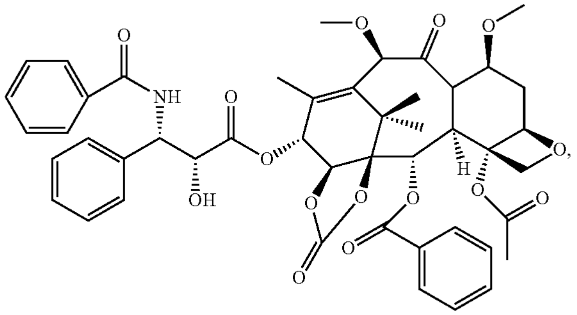

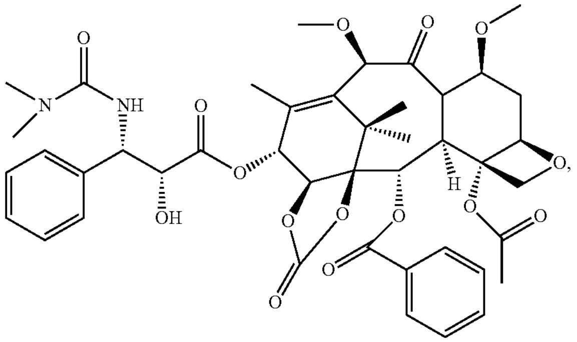

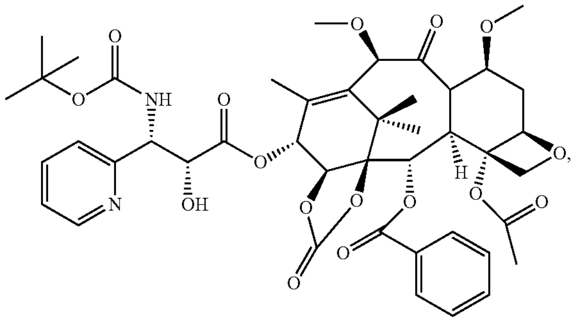

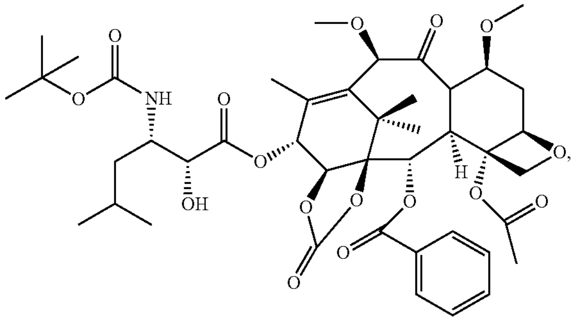

-continued
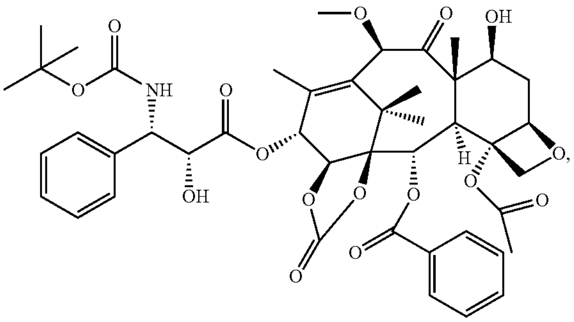,
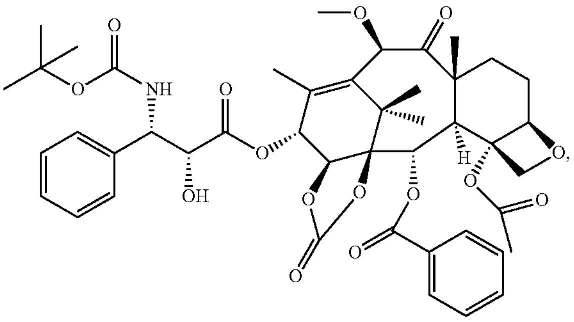,
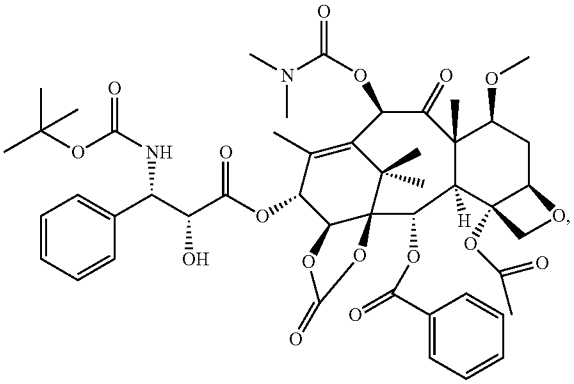,
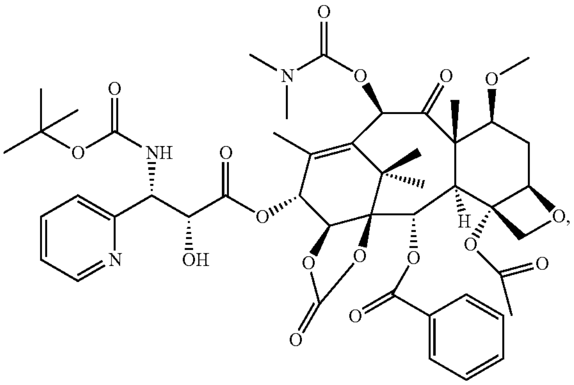,
-continued
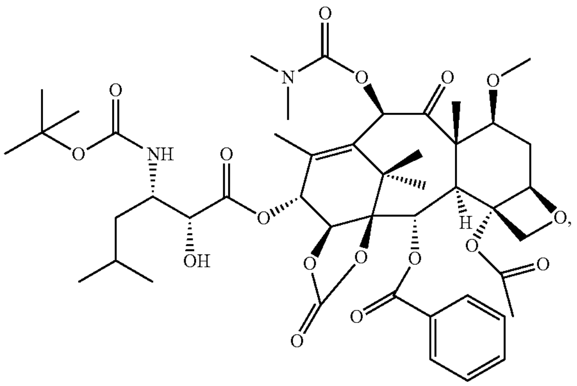,
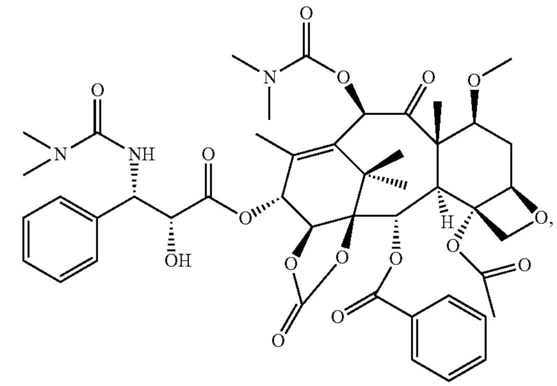,
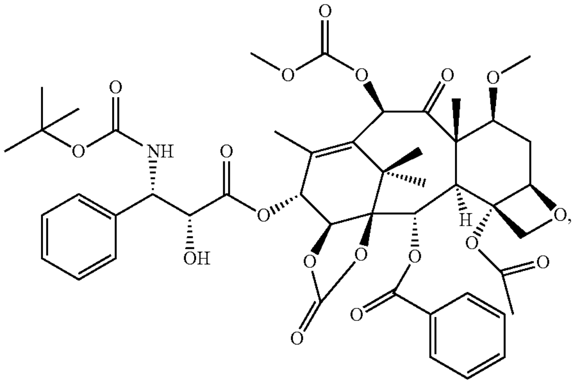,
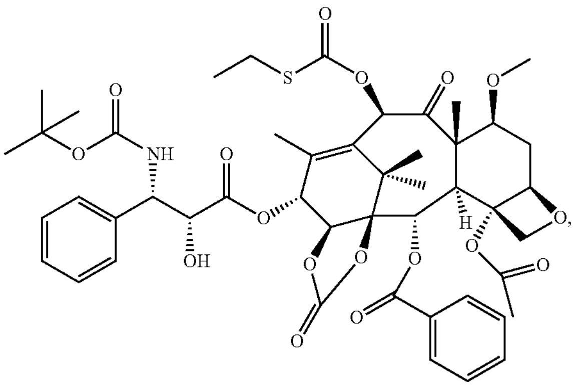, -continued

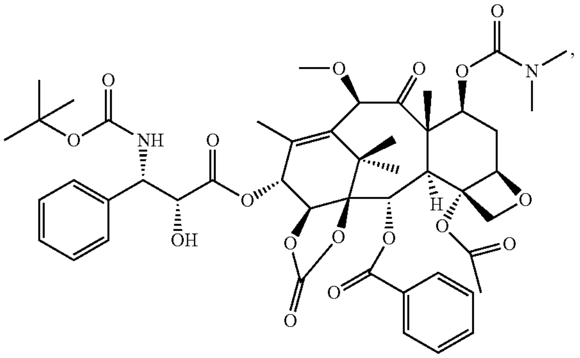

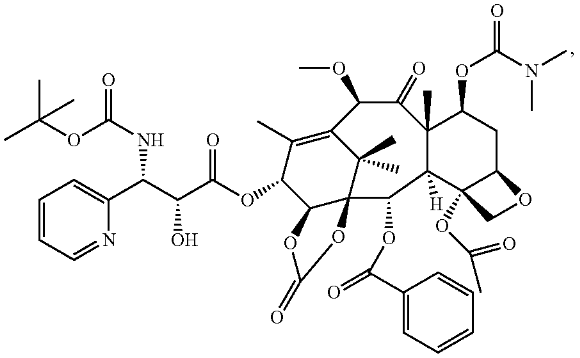

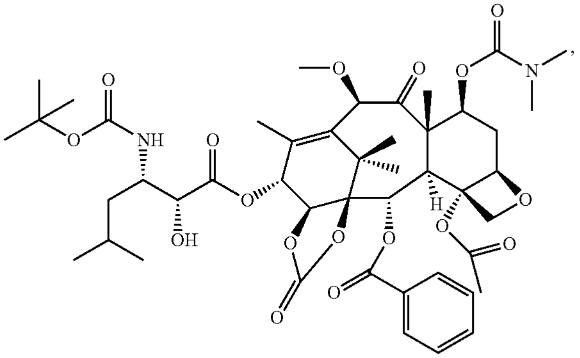

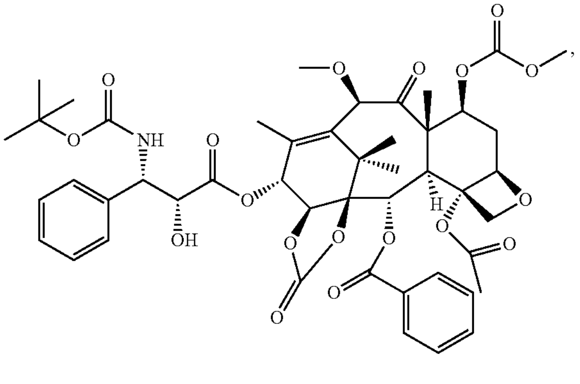

-continued

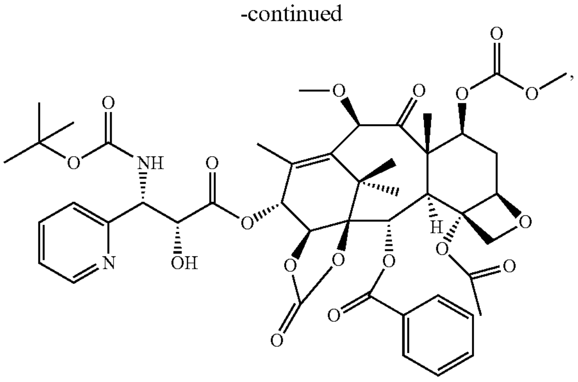

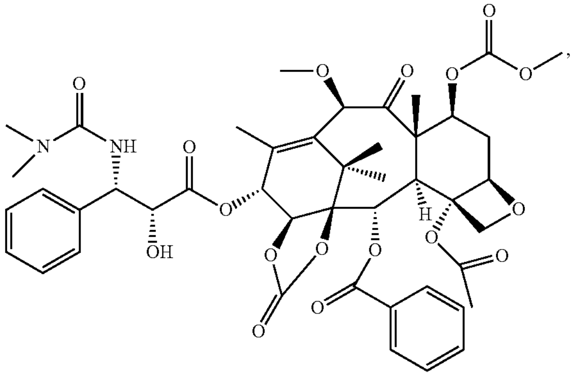

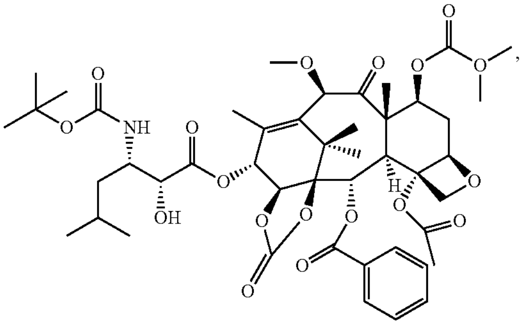

and

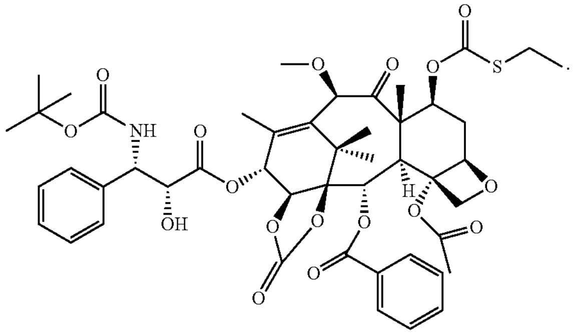

3. The taxanes compounds according to claim 1, wherein said taxanes compounds further include all isomers of these compounds and mixtures of the isomers.

4. The taxanes compounds according to claim 1, wherein said taxanes compounds are formed into pharmaceutically acceptable non-toxic salts.

5. The taxanes compounds according to claim 1, wherein said taxanes compounds exist in a form of solvates.

6. An antitumor pharmaceutical composition, wherein the composition contains the taxanes compounds with formula I according to claim 1, pharmaceutically acceptable salts or solvates thereof as active ingredients.

7. The composition according to claim 6, wherein the pharmaceutical composition contains the taxanes compounds with formula I, pharmaceutically acceptable salts or solvates thereof in a weight ratio of 0.01% to 99.99% with the balance of pharmaceutically acceptable carriers.

8. A preparation method of the taxanes compounds according to claim 1, characterized in that, the method comprises the following steps:

Step 1 synthesis of taxanes mother nucleus part: by using 10-deacetyl baccatin III (10-DAB) as raw material, firstly, the hydroxyl groups at C7 and C10 positions of the mother nucleus part are selectively protected with substitutents, then the C13 hydroxy group is oxidized into keto-carbonyl group, followed by highly stereoselectively introducing a hydroxyl group with β configuration at C14 by using N-(sulfonyl)oxaziridine, to form 1,14-carbonate structure under the action of CDI, and finally the C13 keto-carbonyl group is highly stereoselectively reduced into hydroxyl group with α configuration by CBS reduction method to give the taxanes mother nucleus part;

Step 2 synthesis of a precursor of five-member ring oxazolidine acid side chain: glycolic acid, used as raw material, is protected successively by benzyl group and butyloxycarbonyl group (Boc group) to generate the Boc-protected benzyl glycolate; different substituted aldehydes are condensed with ($S_R$)-t-butyl sulfinamide to form the corresponding enamine compounds; the Boc-protected benzyl glycolate and the enamine compound are reacted via an addition reaction in the presence of lithium salt, and then a chiral intermediate is given after acid hydrolysis, and the obtained intermediate is reacted with 1,1'-(dimethoxymethyl)p-methoxybenzene via an aldol condensation reaction, catalyzed by pyridinium p-toluenesulfonate (PPTS) to obtain a condensation compound; the amino group of the condensation compound is substituted with different substituents, and the precursor of five-member ring oxazolidine acid side chain is finally given after catalytic hydrogenation;

Step 3 synthesis of taxanes derivatives: the precursor of five-member ring oxazolidine acid side chain is linked with the taxanes mother nucleus part by esterification, and a series of taxanes derivatives are generated after removal of the protective group by acid hydrolysis.

9. The preparation method of the taxanes compounds according to claim 8, characterized in that, In Step 1, the C7- and C10-hydroxyl groups are protected with substituents:

(1) When $R_3$ and $R_4$ are —OMe, the reaction involved is: firstly, the hydroxyl group is reacted with p-toluenesulfonyl chloride (TsCl) at room temperature to 0° C. in tetrahydrofuran or dichloromethane as the solvent and pyridine (Py) as the alkali to give p-toluenesulfonate, which is further reacted with a Grignard reagent to give the corresponding ether —OMe;

(2) When $R_3$ and $R_4$ are —OCOOMe or —OCON$(CH_3)_2$, the reaction involved is: under alkaline conditions, the hydroxyl group is reacted with the corresponding acyl chloride in tetrahydrofuran as the solvent at room temperature to −70° C.;

(3) When $R_3$ and $R_4$ are $OCOSC_2H_5$, the reaction involved is: the hydroxyl group is reacted with N,N'-carbonyldiimidazole (CDI) in tetrahydrofuran as the solvent at room temperature, and the obtained product is further reacted with mercaptan via substitution reaction;

In Step 1, the stereoselective reduction on the C13 keto-carbonyl group by CBS reduction method includes the following specific steps: C13-oxo is stereoselectively reduced into C13-α-OH by using anhydrous tetrahydrofuran, dry dichloromethane or alcohols as the solvent, (R)-2-methyl oxazaborodine as the catalyst and boranes as the reducing agent at room temperature to −70° C.;

In Step 2, said different substituted aldehydes include C1-C6 hydrocarbyl aldehydes, C1-C6 substituted hydrocarbyl aldehydes, aromatic aldehydes, substituted aromatic aldehydes and heteroaromatic aldehydes; the reaction involved in the substitution of the amino group of the condensation compound is carried out by using tetrahydrofuran, dichloromethane or dioxane as the solvent, to react with the corresponding acyl chlorides under alkaline conditions at room temperature to −70° C.; in the catalytic hydrogenation reaction, palladium-charcoal or palladium hydroxide is used as the catalyst, hydrogen is introduced at normal pressure or pressurized conditions, and the reaction is carried out in alcohols, tetrahydrofuran or dichloromethane as the solvent.

10. The preparation method of the taxanes compounds according to claim 9, characterized in that, In Step 1, the C7- and C10-hydroxyl groups are protected by substitutents:

(1) When $R_3$ and $R_4$ are —OMe, dichloromethane is used as the solvent, the temperature is at 0° C. and the Grignard reagent includes $CH_3MgBr$;

(2) When $R_3$ and $R_4$ are —OCOOOMe or —OCON$(CH_3)_2$, lithium hexamethyldisilazide is used as the alkali and the temperature is at −40° C.; the acyl chloride includes $CH_3OCOCl$ and $(CH_3)_2NCOCl$;

(3) When $R_3$ and $R_4$ are $OCOSC_2H_5$ the mercaptan includes $C_2H_5SH$;

In Step 1, the stereoselective reduction on the C13 keto-carbonyl group by CBS reduction method is carried out at room temperature by using anhydrous tetrahydrofuran as the solvent;

In Step 2, in the reaction involved in the substitution of the amino group on the condensation compound, lithium hexamethyldisilazide is used as the alkali and tetrahydrofuran is used as the solvent; the temperature is at −40° C., the acyl chloride includes PhCOCl, $C(CH_3)_3$—O—COCl and $(CH_3)_2NCOCl$; in the catalytic hydrogenation reaction, palladium hydroxide is used as the catalyst, hydrogen is introduced at 20 psi and the reaction is carried out in an alcoholic solution.

11. A method for antitumor in a subject, comprising: administering to a subject in need thereof a pharmaceutical composition comprising an effective amount of the taxanes compounds according to claim 1, pharmaceutically acceptable salts or solvates thereof.

* * * * *